(12) United States Patent
Ameriks et al.

(10) Patent No.: US 10,047,092 B2
(45) Date of Patent: *Aug. 14, 2018

(54) SUBSTITUTED [1,2,4]TRIAZOLO[4,3-A]PYRAZINES AS P2X7 MODULATORS

(71) Applicant: Janssen Pharmaceutica NV, Beerse (BE)

(72) Inventors: Michael K. Ameriks, San Diego, CA (US); Jason C. Rech, San Diego, CA (US); Brad M. Savall, San Diego, CA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 14/692,430

(22) Filed: Apr. 21, 2015

(65) Prior Publication Data
US 2015/0290190 A1    Oct. 15, 2015

Related U.S. Application Data

(63) Continuation of application No. 14/212,306, filed on Mar. 14, 2014, now Pat. No. 9,040,534.

(60) Provisional application No. 61/785,478, filed on Mar. 14, 2013.

(51) Int. Cl.
| C07D 487/04 | (2006.01) |
| C07D 487/14 | (2006.01) |
| A61K 31/4985 | (2006.01) |
| A61K 31/501 | (2006.01) |
| A61K 31/506 | (2006.01) |

(52) U.S. Cl.
CPC ........ *C07D 487/04* (2013.01); *A61K 31/4985* (2013.01); *A61K 31/501* (2013.01); *A61K 31/506* (2013.01); *C07D 487/14* (2013.01)

(58) Field of Classification Search
CPC .................................................. C07D 487/04
USPC ........................................................ 544/350
See application file for complete search history.

(56) References Cited

U.S. PATENT DOCUMENTS

| 4,812,462 | A  | 3/1989  | Blankley et al. |
| 4,816,463 | A  | 3/1989  | Blankley et al. |
| 5,338,744 | A  | 8/1994  | Dudley et al. |
| 8,431,704 | B2 | 4/2013  | Love et al. |
| 8,871,760 | B2 | 10/2014 | Brotherton-Pleiss et al. |
| 8,933,236 | B2 | 1/2015  | Chowdhury et al. |
| 8,987,249 | B2 | 3/2015  | Anderskewitz et al. |
| 9,156,824 | B2 | 10/2015 | Dally et al. |
| 9,181,271 | B2 | 11/2015 | Li et al. |
| 9,233,974 | B2 | 1/2016  | Link et al. |
| 9,242,969 | B2 | 1/2016  | Barsanti et al. |
| 9,273,047 | B2 | 3/2016  | Hunt et al. |
| 9,290,476 | B2 | 3/2016  | Leonard et al. |
| 9,375,418 | B2 | 6/2016  | Schmidt et al. |
| 9,434,715 | B2 | 9/2016  | Conza et al. |
| 9,447,045 | B2 | 9/2016  | Chen et al. |
| 9,532,992 | B2 | 1/2017  | Kuntz et al. |
| 9,561,228 | B2 | 2/2017  | Haq et al. |
| 9,617,272 | B2 | 4/2017  | Kumar et al. |
| 9,637,456 | B2 | 5/2017  | Amans et al. |
| 2005/0096345 | A1 | 5/2005  | Thompson et al. |
| 2006/0217448 | A1 | 9/2006  | Kelly et al. |
| 2006/0293337 | A1 | 12/2006 | Evans et al. |
| 2008/0275052 | A1 | 11/2008 | Dhar et al. |
| 2010/0144758 | A1 | 6/2010  | Dillon et al. |
| 2011/0252717 | A1 | 10/2011 | Garf Fernandez |
| 2011/0294790 | A1 | 12/2011 | Mantegani et al. |
| 2012/0190680 | A1 | 7/2012  | Bakthavatchalam et al. |
| 2014/0213554 | A1 | 7/2014  | Wu et al. |
| 2014/0251902 | A1 | 9/2014  | Solheim et al. |
| 2014/0275015 | A1 | 9/2014  | Alcazar Vaca et al. |
| 2014/0275056 | A1 | 9/2014  | Letavic et al. |
| 2014/0275096 | A1 | 9/2014  | Ameriks et al. |
| 2014/0275120 | A1 | 9/2014  | Alcazar Vaca et al. |
| 2016/0016962 | A1 | 1/2016  | Ameriks et al. |
| 2016/0024082 | A1 | 1/2016  | Alcazar Vaca et al. |
| 2016/0039809 | A1 | 2/2016  | Alcazar Vaca et al. |
| 2016/0039836 | A1 | 2/2016  | Letavic et al. |

(Continued)

FOREIGN PATENT DOCUMENTS

| CN | 101778850 | 7/2010 |
| JP | 2013-505220 | 2/2013 |
| WO | WO2004/014374 | 2/2004 |

(Continued)

OTHER PUBLICATIONS

PCT ISR dated Jul. 31, 2009 for International Application No. PCT/US2009/041249.
PCT ISR dated Oct. 15, 2015 for International Application No. PCT/US2015/046710.
U.S. Appl. No. 14/714,714, Non-Final Rejection Office Action, Dated Nov. 23, 2015.
U.S. Appl. No. 14/714,714, Notice of Allowance, Dated Mar. 30, 2016.
U.S. Appl. No. 14/714,714, Notice of Allowance, Dated Jul. 18, 2016.

(Continued)

*Primary Examiner* — Douglas M Willis
(74) *Attorney, Agent, or Firm* — Thomas J. Dodd

(57) ABSTRACT

The present invention is directed to a compound of Formula (I)

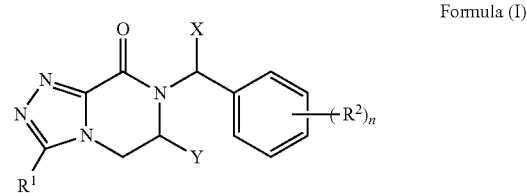

Formula (I)

and to pharmaceutical compositions comprising compounds of Formula (I). Methods of making and using the compounds of Formula (I) are also within the scope of the invention.

11 Claims, No Drawings

(56) References Cited

U.S. PATENT DOCUMENTS

| | | |
|---|---|---|
| 2016/0046596 A1 | 2/2016 | Banerjee et al. |
| 2017/0081342 A1 | 3/2017 | Cheung et al. |

FOREIGN PATENT DOCUMENTS

| | | |
|---|---|---|
| WO | WO 2006/023750 A2 | 3/2006 |
| WO | WO 2006023750 | 3/2006 |
| WO | WO 2006/080884 | 8/2006 |
| WO | WO 2006/110516 | 10/2006 |
| WO | WO 2009/002423 | 12/2008 |
| WO | WO 2009/002423 A2 | 12/2008 |
| WO | WO 2009/023623 | 2/2009 |
| WO | WO 2009/023623 A1 | 2/2009 |
| WO | WO 2010/125101 | 11/2010 |
| WO | WO 2010/125101 A1 | 11/2010 |
| WO | WO 2010/125102 | 11/2010 |
| WO | WO 2010/125102 A1 | 11/2010 |
| WO | WO2011/121137 | 10/2011 |
| WO | WO 2012/040048 | 3/2012 |
| WO | WO 2012/040048 A2 | 3/2012 |
| WO | WO2014/152589 | 9/2014 |
| WO | WO2014/152621 | 9/2014 |
| WO | WO2014/154897 | 10/2014 |
| WO | WO2016/039977 | 3/2016 |
| WO | WO2016/039983 | 3/2016 |

OTHER PUBLICATIONS

U.S. Appl. No. 14/775,436, Non-Final Rejection Office Action, Dated Jul. 27, 2016.
U.S. Appl. No. 14/775,436, Restriction Requirement Office Action, Dated Apr. 27, 2016.
U.S. Appl. No. 14/775,424, Non-Final Rejection Office Action, Dated Jul. 22, 2016.
U.S. Appl. No. 14/775,424, Non-Final Rejection Office Action, Dated Apr. 26, 2016.
Arulkumaran, N., et al. "A Potential Therapeutic Role for P2X7 Receptor (P2X7R) Antagonists in the Treatment of Inflammatory Diseases", Expert Opinion on Investigative Drugs, vol. 20(7), pp. 897-915 (2011).
Hudson, Derek, "Methodological Implications of Simultaneous Solid-Phase Peptide Synthesis. 1. Comparison of Different Coupling Procedures", J. Organic Chemistry, vol. 53, pp. 617-624 (1988).
Killeen, M. E., et al., "Signaling Through Purinergic Receptors for ATP Induces Human Cutaneous Innate and Adaptive Th17 Responses: Implications in the Pathogenesis of Psoriasis", J. Immunology, vol. 190(8), pp. 4324-4336 (2013).
Skaper, S., et al., "The $P2X_7$ Purinergic Receptor: From Physiology to Neurological Disorders", FASEB Journal, vol. 24, pp. 337-345 (2010).
Thiboutot, D., J. "Inflammasome Activation by *Propionibacterium acnes*: The Study of IL-1 in Acne Continues to Unfold", Investigative Dermatology, vol. 134, pp. 595-597 (2014).
Vergani, A., et al., "Long-Term Heart Transplant Survival by Targeting the Ionotropic Purinergic Receptor P2X7", Circulation, vol. 127, pp. 463-475 (2013).
Vergani, A., et al., "Effect of the Purinergic Inhibitor Oxidized ATP in a Model of Islet Allograft Rejection", Diabetes, vol. 62, pp. 1665-1675 (2013).
Thomas A. Godwin (Gastrointestinal Diseases) http://edcenter.med.cornell.edu/CUMC_PathNotes/Gastrointestinal/Gastrointestinal.html.
PCT International Search Report dated Jul. 1, 2014 for International Application No. PCT/US2014/027505.
PCT International Search Report dated Jul. 1, 2014 for International Application No. PCT/US2014/027522.
PCT International Search Report dated Jun. 17, 2014 for International Application No. PCT/US2014/027540.

Arbeloa et al "P2X7 Receptor Blockade Prevents Atp Excitotoxicity in Neurons and Reduces Brain Damage After Ischemia" Neurobiology of Disease, 2012, vol. 45, pp. 954-961.
Avignone et al "Status Epilepticus Induces a Particular Microglial Activation State Characterized by Enhanced Purinergic Signalling" The Journal of Neuroscience, 2008, vol. 28(37), pp. 9133-9144.
Bagshawe et al "Antibody-Directed Enzyme Prodrug Therapy: A Review" Drug Development Research, 1995, vol. 34, pp. 220-230.
Basso et al "Behavioral Profile of P2X7 Receptor Knockout Mice in Animal Models of Depression and Anxiety: Relevance of Neuropsychiatric Disorders" Behavioral Brain Research, 2009, vol. 198, pp. 83-90.
Berge et al "Pharmaceutical Salts" Journal of Pharmaceutical Sciences, 1977, vol. 66(1), pp. 1-19.
Bertolini et al "A New Rational Hypothesis for the Pharmacophore of the Active Metabolite of Leflunomide, A Potent Immunosuppresive Drug" J Med Chem, 1997, vol. 40, pp. 2011-2016.
Bodor et al "Novel Approaches to the Design of Safer Drugs: Soft Drugs and Site-Specific Chemical Delivery Systems" Advances in Drug Research, 1984, vol. 13, pp. 255-331.
Bourzac et al "Glucose Transporter 2 Expression Is Down Regulated Following P2X7 Activation in Enterocytes" J Cell Physiol, 2013, vol. 228, pp. 120-129.
Bundgaard "Design of Prodrugs—(Contents)", Elsevier Science Publishers B.V. (Biomedical Division), 1985, 4 Pgs.
Capouron et al "Immune System to Brain Signaling: Neuropsychopharmacological Implications" Pharmacology & Therapeutics, 2011, vol. 130, pp. 226-238.
Chessel et al "Disruption of the P2X7 Purinoreceptor Gene Abolishes Chronic Inflammatory and Neuropathic Pain", Pain, 2005, vol. 114, pp. 386-396.
Chu et al "Inhibitionof P2XY Receptor Ameliorates Transient Global Cerebral Ischemia/Reperfusion Injury Via Modulating Inflammatory Responses in the Rat Hippocampus" Journal of Neuroinflammation, 2012 9:69, pp. 1-10.
Van Nostrand's Encyclopedia of Chemistry, 2005, $51^{th}$ Ed. p. 261 Considine G D. Ed.
Dantzer et al "Cytokine, Sickness Behavior, and Depression" Immunol Allergy Clin N AM, 2009, vol. 29, pp. 247-264.
Delarasse et al "The Purinergic Receptor P2X7 Triggers α-Secretase-Dependent Processing of the Amyloid Precursor Protein" Journal of Biological Chemistry 2011 vol. 286(4) pp. 2596-2606.
Diaz-Hernandez et al "Altered P2X7-Receptor Level and Function in Mouse Models of Huntington's Disease and Therapeutic Efficacy of Antagonist Administration" FASEB J. 2009 vol. 23(6) pp. 1893-1906.
Diaz-Hernandez et al "In Vivo P2X7 Inhibition Reduces Amyloid Plaques in Alzheimer's Disease Through GXK3β and Secretases" Neurobiology of Aging 2012 vol. 33 pp. 1816-1828.
Donnelly-Roberts et al "[$^3$H]A-804598 ([$^3$H]2-Cyano-1-[(1S)-1-Phenylethyl]-3-Quinolin-5-Ylguanidine) Is a Novel, Potent, and Selective Antagonist Radioligand for P2X7 Receptors" Neuropharmacology 2009 vol. 56 pp. 223-229.
Duan et al "P2X7 Receptors: Properties and Relevance to CNX Function" GLIA 2006 vol. 54 pp. 738-746.
Engel et al "Seizure Suppression and Neuroprotection by Targeting the Purinergic P2X7 Receptor During Status Epilepticus in Mice" FASEB J 2012 vol. 26 pp. 1616-1628.
Ferrari et al "The P2X7 Receptor: A Key Player in IL-1 Processing and Release" J Immunol 2006 vol. 176 pp. 3877-3883.
Fleisher et al "Improved Oreal Drug Delivery: Solubility Limitations Overcome by the Use of Prodrugs" Advanced Drug Delivery Reviews 1996 vol. 19 pp. 115-130.
Friedle et al "Recent Patents on Novel P2X7 Receptor Antagonists and Their Potential for Reducing Central Nervous System Inflammation" Recent Patents on CNS Drug Discovery 2010 vol. 5 pp. 35-45.
Furlan-Freguia et al "P2X7 Receptor Signaling Contributes to Tissue Factor-Dependent Thrombosis in Mice" J Clin Invest 2011 vol. 121(7) pp. 2932-2944.

(56) References Cited

OTHER PUBLICATIONS

Grygorowicz et al "Temporal Expression of P2X7 Purinergic Receptor During the Course of Experimental Autoimmune Encephalomyelitis" Neurochemistry International 2010 vol. 57 pp. 823-829.
Guile et al., "Antagonists of the P2X7, Receptor. From Lead Identification to Drug Development", Journal of Medicinal Chemistry, May 28, 2009, vol. 52, No. 10, pp. 3123-3141.
Gunosewoyo and Kassiou, "PX2 Purinergic Receptor Ligands: Recently Patented Compounds", Brain and Mind Research Institute, 2010, pp. 625-646.
Keating et al "P2X7 Receptor-Dependent Intestinal Afferent Hypersensitity in a Mouse Model of Postinfectious Irritable Bowel Syndrome" The Journal of Immunology 2011 vol. 187 pp. 1467-1474.
Kim et al "Blockade of P2X7 Receptor Prevents Astroglial Death in the Dentate Gyrus Following Pilocarpine-Induced Status Epilepticus" Neurol Res 2009 vol. 31 pp. 982-988.
Larsen and Bundgaard "A Textbook of Drug Design and Development—(Index)", 1992, 18 Pgs., Harwood Academic Publishers.
Marcellino et al "On the Role of P2X7 Receptors in Dopamine Nerve Cell Degeneration in a Rat Model of Parkinson's Disease: Studies With the P2X7 Receptor Antagonist A-438079" J Neural Transm 2010 vol. 117 pp. 681-687.
Martins et al "The Role of P2X7 Purinergic Receptors in Inflammatory and Nociceptive Changes Accompanying Cyclophosphamde-Induced Haemorrhagic Cystitis in Mice" Br J Pharmacol 2012 vol. 165 pp. 183-196.
Muller et al "A Potential Role for P2X7R in Allergic Airway Inflammation in Mice and Humans" Am J Respir Cell Mol Biol 2011 vol. 44 pp. 456-464.
Oyanguren-Desez et al "Gain-Of-Function of P2X7 Receptor Gene Variants in Multiple Sclerosis" Cell Calcium 2011 vol. 50 pp. 468-472.
Parvathenani et al "P2X7 Mediates Superoxide Production in Primary Microglia and Is Up-Regulated in a Transgenic Mouse Model of Alzheimer's Disease" J Biol Chem 2003 vol. 278(15) pp. 13309-13317.
Paulekuhn et al "Trends in Active Pharmaceutical Ingredient Salt Selection Based on Analysis of Athe Orange Book Database" J Med Chem 2007 vol. 30 pp. 6665-6672.
Robinson et al "Discovery of the Hemifumarate and ($_{60}$ -L Alanyloxy)Methyl Ether As Prodrugs of an Antirheumatic Oxindole: Prodrugs for the Enolic Oh Group" J Med Chem 1996 vol. 39 pp. 10-18.
Romagnoli et al "The P2X7 Receptor As a Therapeutic Agent" Expert Opin Ther Targets 2008 vol. 12(5) pp. 647-661.
Sanz et al "Activation of Microglia by Amyloid β Requires P2X7 Receptor Expression" J Immunol 2009 vol. 182 pp. 4378-4385.
Shan et al "Prodrug Strategies Based on Intramolecular Cyclization Reactions" J Pharm Sci 1997 vol. 86(7) pp. 765-767.
Sharp et al "P2X7 Deficiency Suppresses Development of Experimental Autoimmune Encephalomyelitis" J Neuroinflammation 2008 vol. 5 :33.
Skaper et al "The P2X7 Purinergic Receptor: From Physiology to Neurological Disorders" FASEB J 2009 vol. 24 pp. 337-345.
Solini et al "Enhanced P2X7 Activity in Human Fibroblasts From Diabetic Patients—A Possible Pathogenic Mechanism for Vascular Damage in Diabetes" Artherioscler Thromb Vasc Biol 2004 vol. 24 pp. 1240-1245.
Stahl and Wermuth, "Handbook of Pharmaceutical Salts—(Index)", International Union of Pure and Applied Chemistry (IUPAC), 2002, 3 Pgs.
Surprenant et al "Signaling At Purinergic P2X Receptors" Annu Rev Physiol 2009 vol. 71 pp. 333-359.
Ji et al "P2X7 Deficiency Attenuates Hypertension and Renal Injury in Deoxycorticosterone Acetate-Salt Hypertension" Am J Physiol Renal Physiol 2012 vol. 303 pp. F1207-F1215.
PCT International Search Report Dated Aug. 12, 2014 for International Application No. PCT/US2014/027450.
*Handbook of Pharmaceutical Salts, Properties, Selection, and Use*, 2002, (Index), Stahl and Wermuth, Eds., Wiley-VCH and VHCA, Zurich.
Hackman and Redelmeier, "Translation of Research Evidence From Animals to Humans", JAMA, 2006, vol. 296, No. 14, 1731-1732.
Craig Jordan, "Tamoxifen: A Most Unlikely Pioneering Medicine", Nature Reviews, 2003, vol. 2, 205-213.
Dyatkin et al "Determination of the Absolute Configuration of a Key Tricyclic Component of a Novel Vasopressing Receptor Antagonist by Use of Vibrational Circular Dichroism" Chirality 2002 vol. 14 pp. 215-219.
Rudolph et al., "Novel Methyl Substituted 1-(5,6-Dihydro-[1,2,4]Triazolo[4,3-A]Pyrazine-7(8H)-Yl)Methanones Are P2X7 Antagonists", Bioorganic & Medicinal Chemistry Letters, vol. 25, No. 16, Aug. 1, 2015 (Aug. 1, 2015), pp. 3157-3162.
Database Chemcats Enamine Screening Library Database Accession 2035772210 Jan. 17, 2008.
Database Chemcats Ukrorgsynthesis Screeing Collection Accession 2033253463 Mar. 6, 2007.
Database Chemcats Ryan Scientific Screening Library Database Accession 2042676574 Jan. 25, 2008.
Database Chemcats Ambinter Stock Screeing Collection Database Accession 2046454718 Feb. 13, 2008.
Database Chemcats Ryan Scientific Screening Library Database Accession 2043876860 Jan. 25, 2008.
Database Chemcats Ryan Scientific Screening Library Database Accession 2042637020 Jan. 25, 2008.
Database Chemcats Ryan Scientific Screening Library Database Accession 2042634059 Jan. 25, 2008.
Database Chemcats Ambinter Stock Screening Collection Database Accession 2040548370 Feb. 13, 2008.
Database Chemcats Ambinter Stock Screening Collection Database Accession 2040381923 Feb. 13, 2008.
Database Chemcats Ambinter Stock Screening Collection Database Accession 2040033692 Feb. 13, 2008.
Database Chemcats Aurora Screening Library Database Accession 2037938546 Sep. 6, 2007.
Bennet, et al. (Editor), "Part XIV Oncology", Cecil Textbook of Medicine, vol. 1, 20th Edition: pp. 1004-1010 (1996).
Dermer, "Another Anniversary for the War on Cancer", Bio/Technology, vol. 12: pp. 320 (Mar. 1994).
Freshney, et al., Culture of Animal Cells, Manual of Basic Technique, 1933, pp. 1-6, Chapter 1.
Golub, et al., Molecular Classification of cancer: Class Discovery and class prediction by gene expression monitoring, Science, 1999, pp. 531-537, vol. 286.
Simone, Part XIV—Oncology, Textbook of Medicine, 1996, 20th edition, pp. 1004-1010, vol. 1.
Bartlett et al, "The P2X7 Receptor Channel: Recent Developments and the Use of P2X7 Antagonists in Models of Disease", Pharmacol Rev, vol. 66, pp. 838-675, 2014.

SUBSTITUTED [1,2,4]TRIAZOLO[4,3-A]PYRAZINES AS P2X7 MODULATORS

CROSS REFERENCE TO RELATED APPLICATIONS

This application is a continuation of U.S. application Ser. No. 14/212,306, filed Mar. 14, 2014, now U.S. Pat. No. 9,040,534, Issued on May 26, 2015, which claims priority to U.S. Provisional Application No. 61/785,478, filed Mar. 14, 2013, the entire disclosures of which are hereby incorporated in their entirety.

FIELD OF THE INVENTION

The present invention is related to compounds having P2X7 modulating properties, pharmaceutical compositions comprising these compounds, chemical processes for preparing these compounds and their use in the treatment of diseases associated with P2X7 receptor activity in animals, in particular humans. Compounds in this invention can also be used as radiotracers to assess P2X7 receptor occupancy in animals, in particular humans.

BACKGROUND OF THE INVENTION

The P2X7 receptor is a ligand-gated ion channel and is present on a variety of cell types, largely those known to be involved in the inflammatory and/or immune process, specifically, macrophages and monocytes in the periphery and predominantly in glial cells (microglia and astrocytes) of the CNS. (Duan and Neary, *Glia* 2006, 54, 738-746; Skaper et al., *FASEB J* 2009, 24, 337-345; Surprenant and North, *Annu. Rev. Physiol.* 2009, 71, 333-359). Activation of the P2X7 receptor by extracellular nucleotides, in particular adenosine triphosphate, leads to the release of proinflammatory cytokines IL-1β and IL-18 (Muller, et. al. *Am. J. Respir. Cell Mol. Biol.* 2011, 44, 456-464), giant cell formation (macrophages/microglial cells), degranulation (mast cells) and L-selectin shedding (lymphocytes) (Ferrari et al., *J. Immunol.* 2006, 176, 3877-3883; Surprenant and North, *Annu. Rev. Physiol.* 2009, 71, 333-359). P2X7 receptors are also located on antigen-presenting cells (keratinocytes, salivary acinar cells (parotid cells)), hepatocytes, erythrocytes, erythroleukaemic cells, monocytes, fibroblasts, bone marrow cells, neurones, and renal mesangial cells.

The importance of P2X7 in the nervous system arises primarily from experiments using P2X7 knock out mice. These mice demonstrate the role of P2X7 in the development and maintenance of pain as these mice were protected from the development of both adjuvant-induced inflammatory pain and partial nerve ligation induced neuropathic pain (Chessell et al., *Pain* 2005, 114, 386-396). In addition P2X7 knock out mice also exhibit an anti-depressant phenotype based on reduced immobility in forced swim and tail suspension tests (Basso et al., *Behav. Brain Res.* 2009, 198, 83-90.). Moreover, the P2X7 pathway is linked to the release of the pro-inflammatory cytokine, IL-1β, which has been linked to precipitation of mood disorders in humans (Dantzer, *Immunol. Allergy Clin. North Am.* 2009, 29, 247-264; Capuron and Miller, *Pharmacol. Ther.* 2011, 130, 226-238). In addition, in murine models of Alzheimer's disease, P2X7 was upregulated around amyloid plaques indicating a role of this target in such pathology as well (Parvathenani et al., *J. Biol. Chem.* 2003, 278, 13309-13317).

In view of the clinical importance of P2X7, the identification of compounds that modulate P2X7 receptor function represents an attractive avenue into the development of new therapeutic agents. Such compounds are provided herein.

SUMMARY OF THE INVENTION

The invention is directed to the general and preferred embodiments defined, respectively, by the independent and dependent claims appended hereto, which are incorporated by reference herein. One aspect of this invention concerns compounds of Formula (h wherein:

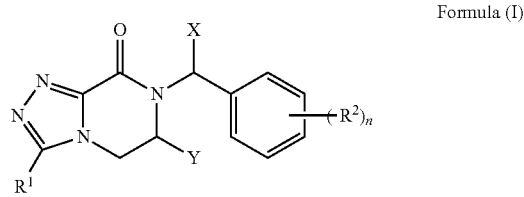

Formula (I)

$R^2$ is H, halo, $SO_2CH_3$, $C_{1-3}$ alkyl, $NO_2$, $NH_2$, perhaloalkyl or perhaloalkoxy; or two $R^2$ substituents are taken together to form:

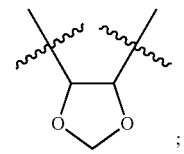 [SMILES: *C1OCOC1*]

n is 0-3;
X is H or $C_1$-$C_3$ alkyl;
Y is H, $C_1$-$C_3$ alkyl or $C_3$-$C_4$ cycloalkyl;
$R^1$ is selected from the group consisting of:

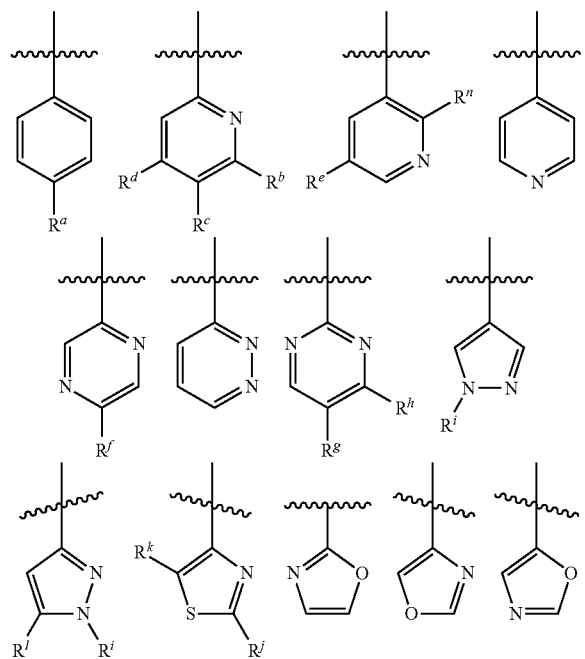

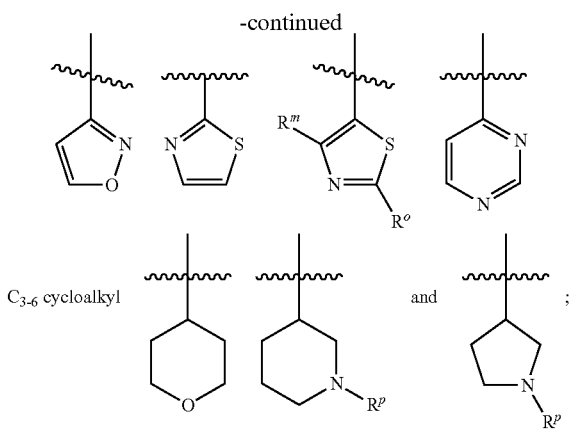

$R^a$, $R^c$ and $R^g$ are independently H or halo;
$R^d$ is H or alkoxy;
$R^e$ is H, $C_1$-$C_3$ alkyl or halo;
$R^b$, $R^f$, $R^h$, $R^i$, $R^j$, $R^k$, $R^l$, $R^m$, $R^n$, $R^o$ are independently H, $C_1$-$C_3$ alkyl or perhaloalkyl and;
$R^p$ is H or C(O)OtBu;
and pharmaceutically acceptable salts of compounds of Formula (I).

Further embodiments are provided by pharmaceutically acceptable salts of compounds of Formula (I), pharmaceutically acceptable prodrugs of compounds of Formula (I), and pharmaceutically active metabolites of compounds of Formula (I).

In certain embodiments, the compound of Formula (I) is a compound selected from those species described or exemplified in the detailed description below.

In a further aspect, the invention relates to pharmaceutical compositions for treating a disease, disorder, or medical condition mediated by P2X7 receptor activity, comprising an effective amount of at least one compound selected from compounds of Formula (I), pharmaceutically acceptable salts of compounds of Formula (I), pharmaceutically acceptable prodrugs of compounds of Formula (I), and pharmaceutically active metabolites of Formula (I).

Pharmaceutical compositions according to the invention may further comprise one or more pharmaceutically acceptable excipients.

In another aspect, the chemical embodiments of the present invention are useful as P2X7 receptor modulators. Thus, the invention is directed to a method for modulating P2X7 receptor activity, including when such receptor is in a subject, comprising exposing P2X7 receptor to an effective amount of at least one compound selected from compounds of Formula (I), pharmaceutically acceptable salts of compounds of Formula (I), pharmaceutically acceptable prodrugs of compounds of Formula (I), and pharmaceutically active metabolites of compounds of Formula (I).

In another aspect, the invention is directed to a method of treating a subject suffering from or diagnosed with a disease, disorder, or medical condition mediated by P2X7 receptor activity, comprising administering to the subject in need of such treatment an effective amount of at least one compound selected from compounds of Formula (I), pharmaceutically acceptable salts of compounds of Formula (I), pharmaceutically acceptable prodrugs of compounds of Formula (I), and pharmaceutically active metabolites of compounds of Formula (I).

Additional embodiments of methods of treatment are set forth in the detailed description.

In another aspect, method of studying isotopically labeled compounds in metabolic studies (preferably with $^{14}C$), reaction kinetic studies (with, for example $^2H$ or $^3H$), detection or imaging techniques [such as positron emission tomography (PET) or single-photon emission computed tomography (SPECT)] including drug or substrate tissue distribution assays, or in radioactive treatment of patients. For example, an $^{18}F$ or $^{11}C$ labeled compound may be particularly preferred for PET or SPECT studies.

An object of the present invention is to overcome or ameliorate at least one of the disadvantages of the conventional methodologies and/or prior art, or to provide a useful alternative thereto.

Additional embodiments, features, and advantages of the invention will be apparent from the following detailed description and through practice of the invention.

Additional embodiments of this invention include methods of making compounds of Formula (I), pharmaceutically acceptable salts of compounds of Formula (I), pharmaceutically acceptable prodrugs of compounds of Formula (I), and pharmaceutically active metabolites of Formula (I).

DETAILED DESCRIPTION OF THE INVENTION

A compound of Formula I wherein:

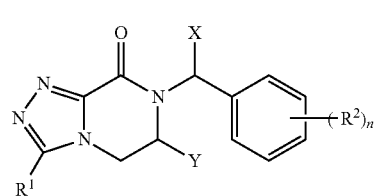

Formula (I)

$R^2$ is H, halo, $SO_2CH_3$, $C_{1-3}$ alkyl, $NO_2$, $NH_2$, perhaloalkyl or perhaloalkoxy; or two $R^2$ substituents are taken together to form:

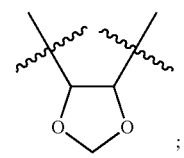 [SMILES: *C1OCOC1*]

n is 0-3;
X is H or $C_1$-$C_3$ alkyl;
Y is H, $C_1$-$C_3$ alkyl or $C_3$-$C_4$ cycloalkyl;
$R^1$ is selected from the group consisting of:

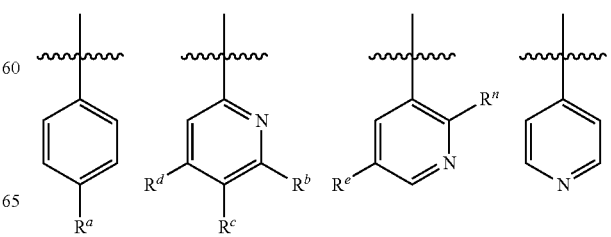

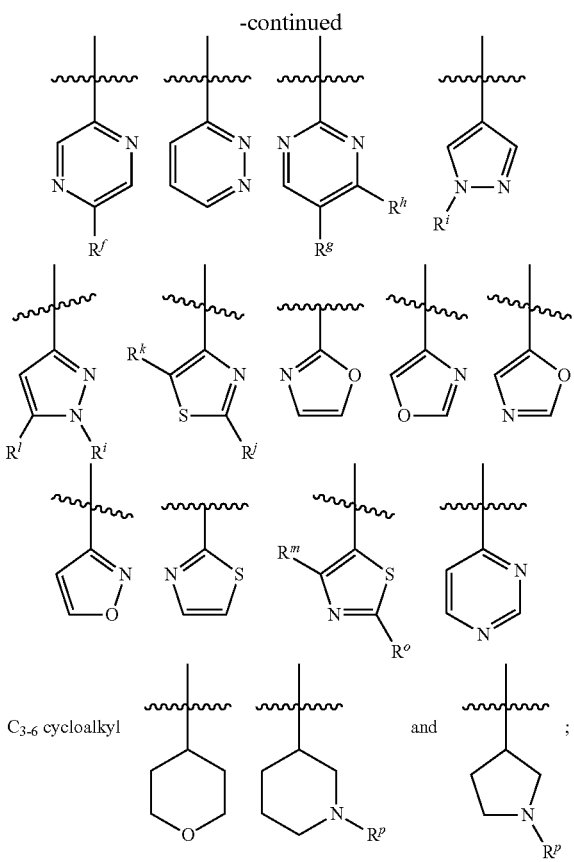

$R^a$, $R^c$ and $R^g$ are independently H or halo;
$R^d$ is H or alkoxy;
$R^e$ is H, $C_1$-$C_3$ alkyl or halo;
$R^b$, $R^f$, $R^h$, $R^i$, $R^j$, $R^k$, $R^l$, $R^m$, $R^n$, $R^o$ are independently H, $C_1$-$C_3$ alkyl or
perhaloalkyl;
$R^p$ is H or C(O)OtBu; and
pharmaceutically acceptable salts of compounds of Formula (I).

An additional embodiment of the invention is a compound of Formula (I), wherein $R^2$ is halo.

An additional embodiment of the invention is a compound of Formula (I), wherein $R^2$ is perfluoroalkyl.

An additional embodiment of the invention is a compound of Formula (I), wherein $R^2$ is halo and perfluoroalkyl.

An additional embodiment of the invention is a compound of Formula (I), wherein n is 0-2.

An additional embodiment of the invention is a compound of Formula (I), wherein n is 1-2.

An additional embodiment of the invention is a compound of Formula (I), wherein n is 2.

An additional embodiment of the invention is a compound of Formula (I), wherein at least one $R^2$ substituent is in the ortho position.

An additional embodiment of the invention is a compound of Formula (I), wherein at least one $R^2$ substituent is in the meta position.

An additional embodiment of the invention is a compound of Formula (I), wherein at least one $R^2$ substituent is in the ortho position and at least one $R^2$ substituent is in the meta position.

An additional embodiment of the invention is a compound of Formula (I), wherein $R^2$ is Cl or F.

An additional embodiment of the invention is a compound of Formula (I), wherein $R^2$ is $CF_3$.

An additional embodiment of the invention is a compound of Formula (I), wherein n is 2, $R^2$ is $CF_3$ and $R^2$ is Cl.

An additional embodiment of the invention is a compound of Formula (I), wherein n is 2, $R^2$ is Cl and is in the ortho position and $R^2$ is $CF_3$ and is in the meta position.

An additional embodiment of the invention is a compound of Formula (I), wherein Y is $C_1$-$C_3$ alkyl or $C_3$-$C_4$ cycloalkyl.

An additional embodiment of the invention is a compound of Formula (I), wherein Y is $C_1$-$C_3$ alkyl.

An additional embodiment of the invention is a compound of Formula (I), wherein Y is $CH_3$, $CH_3CH_2$, or cyclopropyl.

An additional embodiment of the invention is a compound of Formula (I), wherein Y is $CH_3$ or $CH_3CH_2$.

An additional embodiment of the invention is a compound of Formula (I), wherein X is H or $CH_3$.

An additional embodiment of the invention is a compound of Formula (I), wherein X is H.

An additional embodiment of the invention is a compound of Formula (I), wherein $R^1$ is selected from the group consisting of:

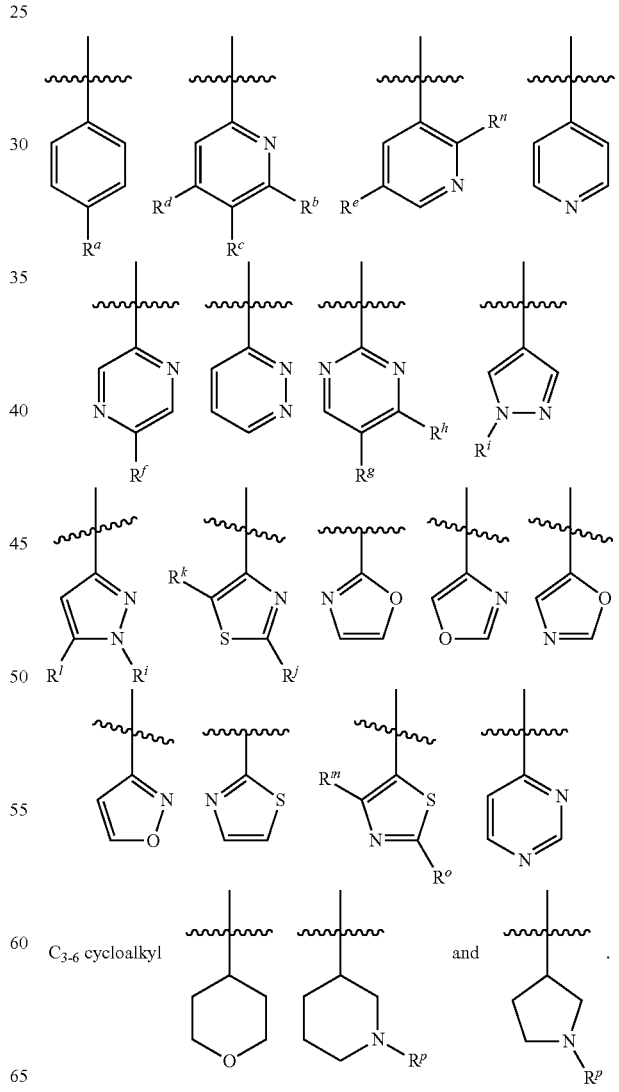

An additional embodiment of the invention is a compound of Formula (I), wherein $R^1$ is selected from the group consisting of:

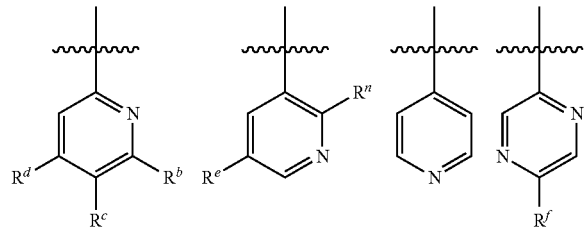

An additional embodiment of the invention is a compound of Formula (I), wherein $R^1$ is selected from the group consisting of:

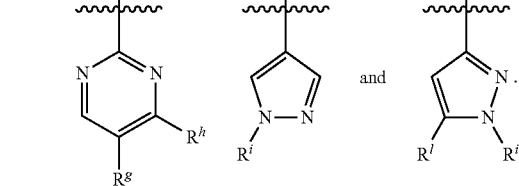

An additional embodiment of the invention is a compound of Formula (I), wherein $R^1$ is selected from the group consisting of:

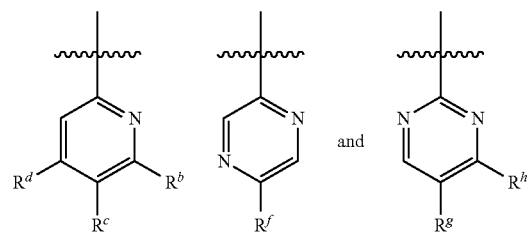

An additional embodiment of the invention is a compound of Formula (I), wherein $R^1$ is selected from the group consisting of:

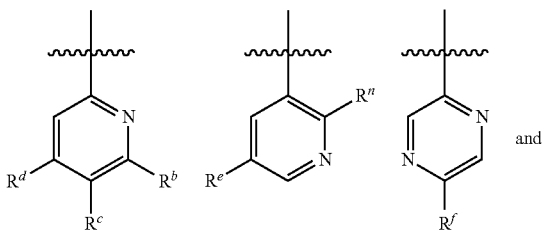

An additional embodiment of the invention is a compound of Formula (I), wherein $R^1$ is selected from the group consisting of:

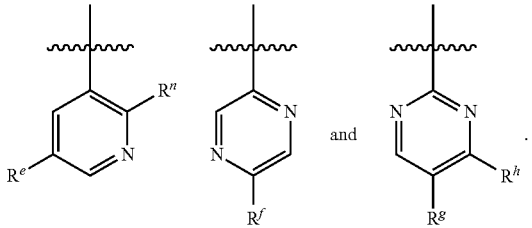

An additional embodiment of the invention is a compound of Formula (I), wherein $R^1$ is:

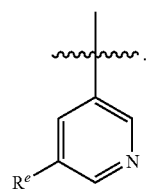

An additional embodiment of the invention is a compound of Formula (I), wherein $R^e$ is F and $R^1$ is:

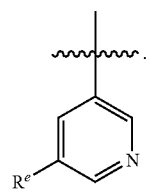

An additional embodiment of the invention is a compound of Formula (I), wherein $R^1$ is:

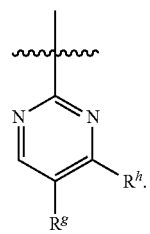

An additional embodiment of the invention is a compound of Formula (I), wherein $R^g$ is F, $R^h$ is H and $R^1$ is

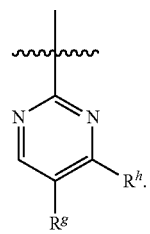

An additional embodiment of the invention is a compound of Formula (I), wherein $R^1$ is An additional embodiment of the invention is a compound of Formula (I), wherein $R^f$ is H and $R^1$ is

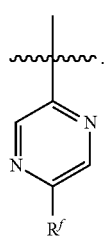

An additional embodiment of the invention is a compound of Formula (I), wherein Y is cyclopropyl, X is H, n is 2, $R^2$ is in the ortho position and is Cl, $R^2$ is in the meta position and is $CF_3$, $R^f$ is H and $R^1$ is

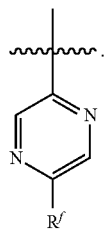

An additional embodiment of the invention is a compound of Formula (I), wherein Y is methyl, X is H, n is 2, $R^2$ is in the ortho position and is Cl, $R^1$ is in the meta position and is $CF_3$, $R^c$ is F, $R^b$ and $R^d$ are H and $R^1$ is

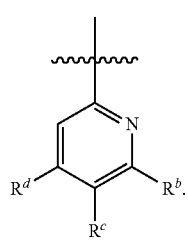

An additional embodiment of the invention is a compound of Formula (I), wherein Y is $CH_3$, X is H, $R^2$ is in the ortho position and is Cl, $R^2$ is in the meta position and is $CF_3$, $R^g$ is F, $R^h$ is H and $R^1$ is An additional embodiment of the invention is a compound of Formula (I), wherein Y is $CH_3$, X is H, $R^2$ is in the ortho position and is Cl, $R^2$ is in the meta position and is $CF_3$, $R^f$ is H and $R^1$ is

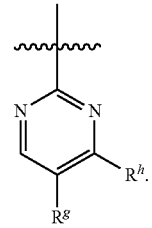

An additional embodiment of the invention is a compound of Formula (I), wherein Y is $CH_3$, X is H, $R^2$ is in the ortho position and is Cl, $R^2$ is in the meta position and is CF, $R^g$ is $^3$H, $R^h$ is H and $R^1$ is

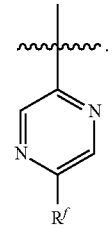

An additional embodiment of the invention is a compound of Formula (I), wherein Y is $CH_3$, X is H, $R^2$ is in the ortho position and is Cl, $R^2$ is in the meta position and is $CF_3$, $R^f$ is H and $R^1$ is

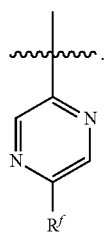

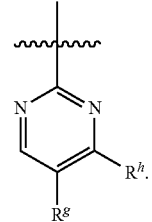

An additional embodiment of the invention is a compound selected from the group consisting of those presented in Table 1:

TABLE 1

| Compounds of the Invention |
|---|
| 7-[2-Chloro-3-(trifluoromethyl)benzyl]-3-(4-fluorophenyl)-6,7-dihydro[1,2,4]triazolo[4,3-a]pyrazin-8(5H)-one |
| 7-(2,3-Dichlorobenzyl)-3-pyrazin-2-yl-6,7-dihydro[1,2,4]triazolo[4,3-a]pyrazin-8(5H)-one |
| 7-[2-Chloro-3-(trifluoromethyl)benzyl]-3-pyrazin-2-yl-6,7-dihydro[1,2,4]triazolo[4,3-a]pyrazin-8(5H)-one |
| (±)7-{1-[2-Chloro-3-(trifluoromethyl)phenyl]ethyl}-3-pyrazin-2-yl-6,7-dihydro[1,2,4]triazolo[4,3-a]pyrazin-8(5H)-one |
| 7-(2,6-Dichlorobenzyl)-3-pyrazin-2-yl-6,7-dihydro[1,2,4]triazolo[4,3-a]pyrazin-8(5H)-one |
| 7-(2,3-Difluorobenzyl)-3-pyrazin-2-yl-6,7-dihydro[1,2,4]triazolo[4,3-a]pyrazin-8(5H)-one |
| 7-[4-Chloro-2-(methylsulfonyl)benzyl]-3-pyrazin-2-yl-6,7-dihydro[1,2,4]triazolo[4,3-a]pyrazin-8(5H)-one |
| 7-(2,3-Dichlorobenzyl)-3-pyridin-2-yl-6,7-dihydro[1,2,4]triazolo[4,3-a]pyrazin-8(5H)-one |
| 7-[2-Chloro-3-(trifluoromethyl)benzyl]-3-pyridin-2-yl-6,7-dihydro[1,2,4]triazolo[4,3-a]pyrazin-8(5H)-one |

TABLE 1-continued

Compounds of the Invention

7-[2-Methyl-3-(trifluoromethyl)benzyl]-3-pyridin-2-yl-6,7-dihydro[1,2,4]triazolo[4,3-a]pyrazin-8(5H)-one
(±)-7-(2,3-Dichlorobenzyl)-6-methyl-3-pyrazin-2-yl-6,7-dihydro[1,2,4]triazolo[4,3-a]pyrazin-8(5H)-one
(6R)-7-(2,3-Dichlorobenzyl)-6-methyl-3-pyrazin-2-yl-6,7-dihydro[1,2,4]triazolo[4,3-a]pyrazin-8(5H)-one
(6S)-7-(2,3-Dichlorobenzyl)-6-methyl-3-pyrazin-2-yl-6,7-dihydro[1,2,4]triazolo[4,3-a]pyrazin-8(5H)-one
(±)-7-[2-Chloro-3-(trifluoromethyl)benzyl]-6-methyl-3-pyrazin-2-yl-6,7-dihydro[1,2,4]triazolo[4,3-a]pyrazin-8(5H)-one
(6R)-7-[2-Chloro-3-(trifluoromethyl)benzyl]-6-methyl-3-pyrazin-2-yl-6,7-dihydro[1,2,4]triazolo[4,3-a]pyrazin-8(5H)-one
(6S)-7-[2-Chloro-3-(trifluoromethyl)benzyl]-6-methyl-3-pyrazin-2-yl-6,7-dihydro[1,2,4]triazolo[4,3-a]pyrazin-8(5H)-one
(6S)-7-[2-Chloro-3-(trifluoromethyl)benzyl]-3-(4-fluorophenyl)-6-methyl-6,7-dihydro[1,2,4]triazolo[4,3-a]pyrazin-8(5H)-one.
(6S)-7-[2-Chloro-3-(trifluoromethyl)benzyl]-6-methyl-3-pyridin-2-yl-6,7-dihydro[1,2,4]triazolo[4,3-a]pyrazin-8(5H)-one
(6S)-7-[2-Chloro-3-(trifluoromethyl)benzyl]-6-methyl-3-(5-methylpyrazin-2-yl)-6,7-dihydro[1,2,4]triazolo[4,3-a]pyrazin-8(5H)-one
(6S)-7-[2-Chloro-3-(trifluoromethyl)benzyl]-6-methyl-3-(1,3-oxazol-2-yl)-6,7-dihydro[1,2,4]triazolo[4,3-a]pyrazin-8(5H)-one
(6S)-7-[2-Chloro-3-(trifluoromethyl)benzyl]-6-methyl-3-(1,3-oxazol-4-yl)-6,7-dihydro[1,2,4]triazolo[4,3-a]pyrazin-8(5H)-one
(6S)-7-[2-Chloro-3-(trifluoromethyl)benzyl]-6-methyl-3-(1,3-oxazol-5-yl)-6,7-dihydro[1,2,4]triazolo[4,3-a]pyrazin-8(5H)-one
(6S)-7-[2-Chloro-3-(trifluoromethyl)benzyl]-6-methyl-3-(1-methyl-1H-pyrazol-3-yl)-6,7-dihydro[1,2,4]triazolo[4,3-a]pyrazin-8(5H)-one
(6S)-7-[2-Chloro-3-(trifluoromethyl)benzyl]-6-methyl-3-(1-methyl-1H-pyrazol-4-yl)-6,7-dihydro[1,2,4]triazolo[4,3-a]pyrazin-8(5H)-one
(6S)-7-[2-Chloro-3-(trifluoromethyl)benzyl]-6-methyl-3-(1H-pyrazol-4-yl)-6,7-dihydro[1,2,4]triazolo[4,3-a]pyrazin-8(5H)-one
(6S)-7-[2-Chloro-3-(trifluoromethyl)benzyl]-6-methyl-3-(5-methyl-1H-pyrazol-3-yl)-6,7-dihydro[1,2,4]triazolo[4,3-a]pyrazin-8(5H)-one
(6S)-7-[2-Chloro-3-(trifluoromethyl)benzyl]-6-methyl-3-pyrimidin-2-yl-6,7-dihydro[1,2,4]triazolo[4,3-a]pyrazin-8(5H)-one
(6S)-7-[2-Chloro-3-(trifluoromethyl)benzyl]-6-methyl-3-(1H-pyrazol-3-yl)-6,7-dihydro[1,2,4]triazolo[4,3-a]pyrazin-8(5H)-one
(6S)-7-[2-Chloro-3-(trifluoromethyl)benzyl]-6-methyl-3-pyridin-3-yl-6,7-dihydro[1,2,4]triazolo[4,3-a]pyrazin-8(5H)-one
(6S)-7-[2-Chloro-3-(trifluoromethyl)benzyl]-3-(5-fluoropyridin-2-yl)-6-methyl-6,7-dihydro[1,2,4]triazolo[4,3-a]pyrazin-8(5H)-one
(6S)-7-[2-Chloro-3-(trifluoromethyl)benzyl]-6-methyl-3-(1,3-thiazol-2-yl)-6,7-dihydro[1,2,4]triazolo[4,3-a]pyrazin-8(5H)-one
(6S)-7-[2-Chloro-3-(trifluoromethyl)benzyl]-6-methyl-3-(1,3-thiazol-4-yl)-6,7-dihydro[1,2,4]triazolo[4,3-a]pyrazin-8(5H)-one
(6S)-7-[2-Chloro-3-(trifluoromethyl)benzyl]-6-methyl-3-pyrimidin-4-yl-6,7-dihydro[1,2,4]triazolo[4,3-a]pyrazin-8(5H)-one
(6S)-7-[2-Chloro-3-(trifluoromethyl)benzyl]-3-(5-fluoropyrimidin-2-yl)-6-methyl-6,7-dihydro[1,2,4]triazolo[4,3-a]pyrazin-8(5H)-one
(6S)-7-[2-Chloro-3-(trifluoromethyl)benzyl]-3-(4-methoxypyridin-2-yl)-6-methyl-6,7-dihydro[1,2,4]triazolo[4,3-a]pyrazin-8(5H)-one
(6S)-7-[2-Chloro-3-(trifluoromethyl)benzyl]-6-methyl-3-(2-methyl-1,3-thiazol-4-yl)-6,7-dihydro[1,2,4]triazolo[4,3-a]pyrazin-8(5H)-one
(6S)-7-[2-Chloro-3-(trifluoromethyl)benzyl]-6-methyl-3-(1,3-thiazol-5-yl)-6,7-dihydro[1,2,4]triazolo[4,3-a]pyrazin-8(5H)-one
(6S)-7-[2-Chloro-3-(trifluoromethyl)benzyl]-6-methyl-3-[2-(trifluoromethyl)-1,3-thiazol-4-yl]-6,7-dihydro[1,2,4]triazolo[4,3-a]pyrazin-8(5H)-one
(6S)-7-[2-Chloro-3-(trifluoromethyl)benzyl]-3-(2,4-dimethyl-1,3-thiazol-5-yl)-6-methyl-6,7-dihydro[1,2,4]triazolo[4,3-a]pyrazin-8(5H)-one
(6S)-7-[2-Chloro-3-(trifluoromethyl)benzyl]-6-methyl-3-(4-methyl-1,3-thiazol-5-yl)-6,7-dihydro[1,2,4]triazolo[4,3-a]pyrazin-8(5H)-one
(6S)-7-[2-Chloro-3-(trifluoromethyl)benzyl]-3-isoxazol-3-yl-6-methyl-6,7-dihydro[1,2,4]triazolo[4,3-a]pyrazin-8(5H)-one
(6S)-3-(5-Bromopyrimidin-2-yl)-7-[2-chloro-3-(trifluoromethyl)benzyl]-6-methyl-6,7-dihydro[1,2,4]triazolo[4,3-a]pyrazin-8(5H)-one
(6S)-3-(5-Tritiopyrimidin-2-yl)-7-[2-chloro-3-(trifluoromethyl)benzyl]-6-methyl-6,7-dihydro[1,2,4]triazolo[4,3-a]pyrazin-8(5H)-one
(6S)-7-[2-Chloro-3-(trifluoromethyl)benzyl]-6-methyl-3-pyridazin-3-yl-6,7-dihydro[1,2,4]triazolo[4,3-a]pyrazin-8(5H)-one
(6S)-7-[2-Chloro-3-(trifluoromethyl)benzyl]-3-(5-fluoropyridin-3-yl)-6-methyl-6,7-dihydro[1,2,4]triazolo[4,3-a]pyrazin-8(5H)-one
(6S)-7-[2-Chloro-3-(trifluoromethyl)benzyl]-6-methyl-3-(6-methylpyridin-2-yl)-6,7-dihydro[1,2,4]triazolo[4,3-a]pyrazin-8(5H)-one
(6S)-7-[2-Chloro-3-(trifluoromethyl)benzyl]-6-methyl-3-pyridin-4-yl-6,7-dihydro[1,2,4]triazolo[4,3-a]pyrazin-8(5H)-one
(6S)-7-[2-Chloro-3-(trifluoromethyl)benzyl]-6-methyl-3-(2-methylpyridin-3-yl)-6,7-dihydro[1,2,4]triazolo[4,3-a]pyrazin-8(5H)-one
(6S)-7-[2-Chloro-3-(trifluoromethyl)benzyl]-3-cyclobutyl-6-methyl-6,7-dihydro[1,2,4]triazolo[4,3-a]pyrazin-8(5H)-one
(6S)-7-[2-Chloro-3-(trifluoromethyl)benzyl]-3-cyclopropyl-6-methyl-6,7-dihydro[1,2,4]triazolo[4,3-a]pyrazin-8(5H)-one
(6S)-7-[2-Chloro-3-(trifluoromethyl)benzyl]-3-cyclohexyl-6-methyl-6,7-dihydro[1,2,4]triazolo[4,3-a]pyrazin-8(5H)-one
(6S)-3-(5-Chloropyridin-3-yl)-7-[2-chloro-3-(trifluoromethyl)benzyl]-6-methyl-6,7-dihydro[1,2,4]triazolo[4,3-a]pyrazin-8(5H)-one
(6S)-7-[2-Chloro-3-(trifluoromethyl)benzyl]-6-methyl-3-(tetrahydro-2H-pyran-4-yl)-6,7-dihydro[1,2,4]triazolo[4,3-a]pyrazin-8(5H)-one
(6S)-7-[2-chloro-3-(trifluoromethyl)benzyl]-6-methyl-3-[4-(trifluoromethyl)pyrimidin-2-yl]-6,7-dihydro[1,2,4]triazolo[4,3-a]pyrazin-8(5H)-one
(6S)-7-[2-Chloro-3-(trifluoromethyl)benzyl]-6-methyl-3-[6-(trifluoromethyl)pyridin-2-yl]-6,7-dihydro[1,2,4]triazolo[4,3-a]pyrazin-8(5H)-one
(6S)-3-(5-Chloropyridin-2-yl)-7-[2-chloro-3-(trifluoromethyl)benzyl]-6-methyl-6,7-dihydro[1,2,4]triazolo[4,3-a]pyrazin-8(5H)-one
(6S)-7-[2-Chloro-3-(trifluoromethyl)benzyl]-6-methyl-3-(5-methylpyridin-3-yl)-6,7-dihydro[1,2,4]triazolo[4,3-a]pyrazin-8(5H)-one
(6S)-tert-Butyl3-{7-[2-chloro-3-(trifluoromethyl)benzyl]-6-methyl-8-oxo-5,6,7,8-tetrahydro[1,2,4]triazolo[4,3-a]pyrazin-3-yl}pyrrolidine-1-carboxylate
(6S)-tert-Butyl3-{7-[2-chloro-3-(trifluoromethyl)benzyl]-6-methyl-8-oxo-5,6,7,8-tetrahydro[1,2,4]triazolo[4,3-a]pyrazin-3-yl}piperidine-1-carboxylate
(6S)-7-[2-Chloro-3-(trifluoromethyl)benzyl]-6-methyl-3-piperidin-3-yl-6,7-dihydro[1,2,4]triazolo[4,3-a]pyrazin-8(5H)-one
(±)-7-[2-Chloro-3-(trifluoromethyl)benzyl]-6-cyclopropyl-3-pyrazin-2-yl-6,7-dihydro[1,2,4]triazolo[4,3-a]pyrazin-8(5H)-one
(6R*)-7-[2-Chloro-3-(trifluoromethyl)benzyl]-6-cyclopropyl-3-pyrazin-2-yl-6,7-dihydro[1,2,4]triazolo[4,3-a]pyrazin-8(5H)-one
(6S*)-7-[2-Chloro-3-(trifluoromethyl)benzyl]-6-cyclopropyl-3-pyrazin-2-yl-6,7-dihydro[1,2,4]triazolo[4,3-a]pyrazin-8(5H)-one
(±)-7-[2-Chloro-3-(trifluoromethyl)benzyl]-6-cyclopropyl-3-pyrimidin-2-yl-6,7-dihydro[1,2,4]triazolo[4,3-a]pyrazin-8(5H)-one

TABLE 1-continued

Compounds of the Invention (6R*)-7-[2-Chloro-3-(trifluoromethyl)benzyl]-6-cyclopropyl-3-pyrimidin-2-yl-6,7-dihydro[1,2,4]triazolo[4,3-a]pyrazin-8(5H)-one
(6S*)-7-[2-Chloro-3-(trifluoromethyl)benzyl]-6-cyclopropyl-3-pyrimidin-2-yl-6,7-dihydro[1,2,4]triazolo[4,3-a]pyrazin-8(5H)-one.
(±)-7-[2-Chloro-3-(trifluoromethyl)benzyl]-6-cyclopropyl-3-pyridin-3-yl-6,7-dihydro[1,2,4]triazolo[4,3-a]pyrazin-8(5H)-one
(±)-7-[2-Chloro-3-(trifluoromethyl)benzyl]-6-cyclopropyl-3-(1H-pyrazol-3-yl)-6,7-dihydro[1,2,4]triazolo[4,3-a]pyrazin-8(5H)-one
(±)-7-[2-Chloro-3-(trifluoromethyl)benzyl]-6-cyclopropyl-3-(5-fluoropyridin-2-yl)-6,7-dihydro[1,2,4]triazolo[4,3-a]pyrazin-8(5H)-one
(±)-7-[2-Chloro-3-(trifluoromethyl)benzyl]-6-cyclopropyl-3-(5-fluoropyrimidin-2-yl)-6,7-dihydro[1,2,4]triazolo[4,3-a]pyrazin-8(5H)-one
(6S)-7-[2-Chloro-3-(trifluoromethyl)benzyl]-6-ethyl-3-pyrazin-2-yl-6,7-dihydro[1,2,4]triazolo[4,3-a]pyrazin-8(5H)-one
(6S)-7-[2-Chloro-3-(trifluoromethyl)benzyl]-6-ethyl-3-pyrimidin-2-yl-6,7-dihydro[1,2,4]triazolo[4,3-a]pyrazin-8(5H)-one
(6S)-7-[2-Chloro-3-(trifluoromethyl)benzyl]-6-ethyl-3-pyridin-3-yl-6,7-dihydro[1,2,4]triazolo[4,3-a]pyrazin-8(5H)-one
(6S)-7-[2-Chloro-3-(trifluoromethyl)benzyl]-6-ethyl-3-(1H-pyrazol-3-yl)-6,7-dihydro[1,2,4]triazolo[4,3-a]pyrazin-8(5H)-one
(6S)-7-[2-Chloro-3-(trifluoromethyl)benzyl]-6-ethyl-3-(5-fluoropyrimidin-2-yl)-6,7-dihydro[1,2,4]triazolo[4,3-a]pyrazin-8(5H)-one
(6S)-7-[2-Chloro-3-(trifluoromethyl)benzyl]-6-ethyl-3-(5-fluoropyridin-2-yl)-6,7-dihydro[1,2,4]triazolo[4,3-a]pyrazin-8(5H)-one
(6S)-6-Methyl-3-pyrazin-2-yl-6,7-dihydro[1,2,4]triazolo[4,3-a]pyrazin-8(5H)-one
(6S)-7-(2-Chloro-4-fluorobenzyl)-6-methyl-3-pyrazin-2-yl-6,7-dihydro[1,2,4]triazolo[4,3-a]pyrazin-8(5H)-one
(6S)-7-Benzyl-6-methyl-3-pyrazin-2-yl-6,7-dihydro[1,2,4]triazolo[4,3-a]pyrazin-8(5H)-one
(6S)-7-(2-Chlorobenzyl)-6-methyl-3-pyrazin-2-yl-6,7-dihydro[1,2,4]triazolo[4,3-a]pyrazin-8(5H)-one
(6S)-7-[2-Chloro-4-(methylsulfonyl)benzyl]-6-methyl-3-pyrazin-2-yl-6,7-dihydro[1,2,4]triazolo[4,3-a]pyrazin-8(5H)-one
(6S)-7-[4-Chloro-2-(methylsulfonyl)benzyl]-6-methyl-3-pyrazin-2-yl-6,7-dihydro[1,2,4]triazolo[4,3-a]pyrazin-8(5H)-one
(6S)-6-Methyl-3-pyrazin-2-yl-7-[2-(trifluoromethoxy)benzyl]-6,7-dihydro[1,2,4]triazolo[4,3-a]pyrazin-8(5H)-one
(6S)-7-[(6-Chloro-1,3-benzodioxol-5-yl)methyl]-6-methyl-3-pyrazin-2-yl-6,7-dihydro[1,2,4]triazolo[4,3-a]pyrazin-8(5H)-one
(6S)-6-Methyl-7-[2-methyl-3-(trifluoromethyl)benzyl]-3-pyrazin-2-yl-6,7-dihydro[1,2,4]triazolo[4,3-a]pyrazin-8(5H)-one
(6S)-7-(2,6-Dichlorobenzyl)-6-methyl-3-pyrazin-2-yl-6,7-dihydro[1,2,4]triazolo[4,3-a]pyrazin-8(5H)-one
(6S)-7-(2,6-Dimethylbenzyl)-6-methyl-3-pyrazin-2-yl-6,7-dihydro[1,2,4]triazolo[4,3-a]pyrazin-8(5H)-one
(6S)-6-Methyl-3-pyrazin-2-yl-7-[3-(trifluoromethyl)benzyl]-6,7-dihydro[1,2,4]triazolo[4,3-a]pyrazin-8(5H)-one
(6S)-6-Methyl-7-(2-nitrobenzyl)-3-pyrazin-2-yl-6,7-dihydro[1,2,4]triazolo[4,3-a]pyrazin-8(5H)-one
(6S)-7-(2-Chloro-5-nitrobenzyl)-6-methyl-3-pyrazin-2-yl-6,7-dihydro[1,2,4]triazolo[4,3-a]pyrazin-8(5H)-one
(6S)-7-(5-Amino-2-chlorobenzyl)-6-methyl-3-pyrazin-2-yl-6,7-dihydro[1,2,4]triazolo[4,3-a]pyrazin-8(5H)-one
(6S)-6-Methyl-7-(1-phenylethyl)-3-pyrazin-2-yl-6,7-dihydro[1,2,4]triazolo[4,3-a]pyrazin-8(5H)-one
(6S)-6-Methyl-7-[(1R/S)-1-phenylethyl]-3-pyrazin-2-yl-6,7-dihydro[1,2,4]triazolo[4,3-a]pyrazin-8(5H)-one
(6S)-6-Methyl-7-[(1R*)-1-phenylethyl]-3-pyrazin-2-yl-6,7-dihydro[1,2,4]triazolo[4,3-a]pyrazin-8(5H)-one
(6S)-6-Methyl-7-[(1S*)-1-phenylethyl]-3-pyrazin-2-yl-6,7-dihydro[1,2,4]triazolo[4,3-a]pyrazin-8(5H)-one An additional embodiment of the invention is a pharmaceutical composition for treating a disease, disorder or medical condition mediated by P2X7 activity comprising:

(a) an effective amount of at least one compound selected from compounds of Formula (I)

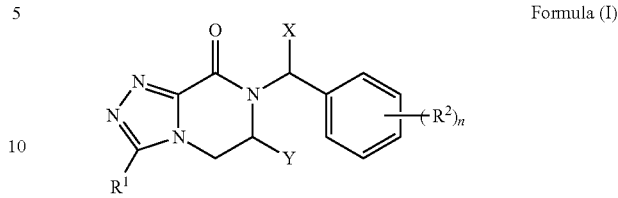

Formula (I)

wherein:

$R^2$ is H, halo, $SO_2CH_3$, $C_{1-3}$ alkyl, $NO_2$, $NH_2$, perhaloalkyl or perhaloalkoxy; or two $R^2$ substituents are taken together to form:

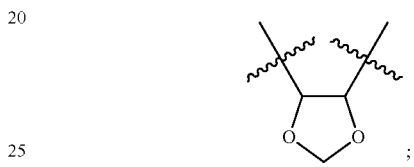

;

n is 0-3;

X is H or $C_1$-$C_3$ alkyl;

Y is H, $C_1$-$C_3$ alkyl or $C_3$-$C_4$ cycloalkyl;

$R^1$ is selected from the group consisting of:

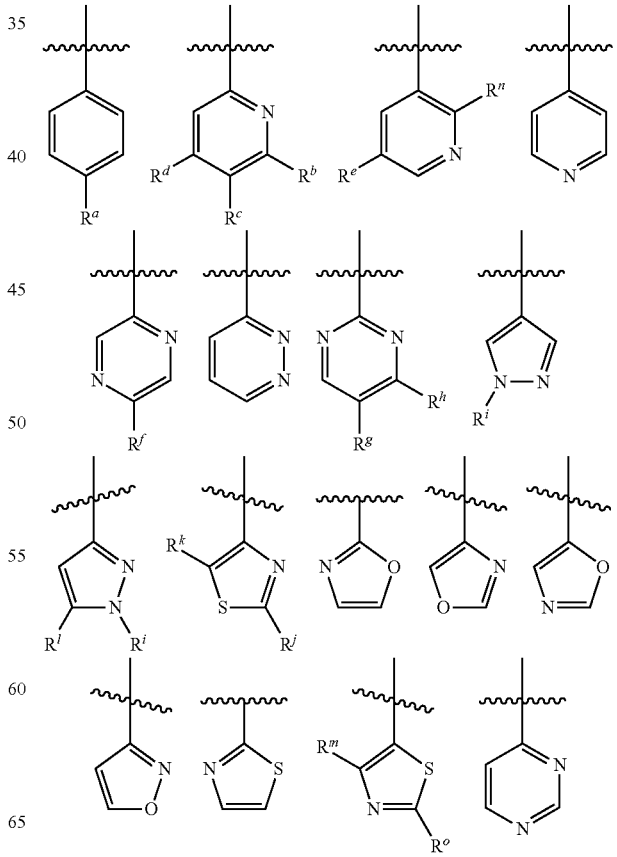

-continued

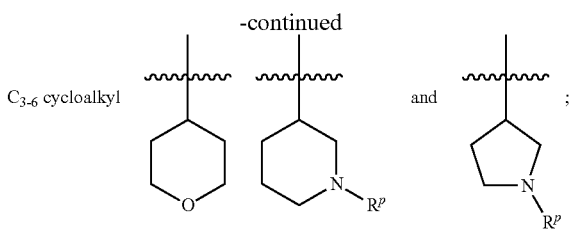

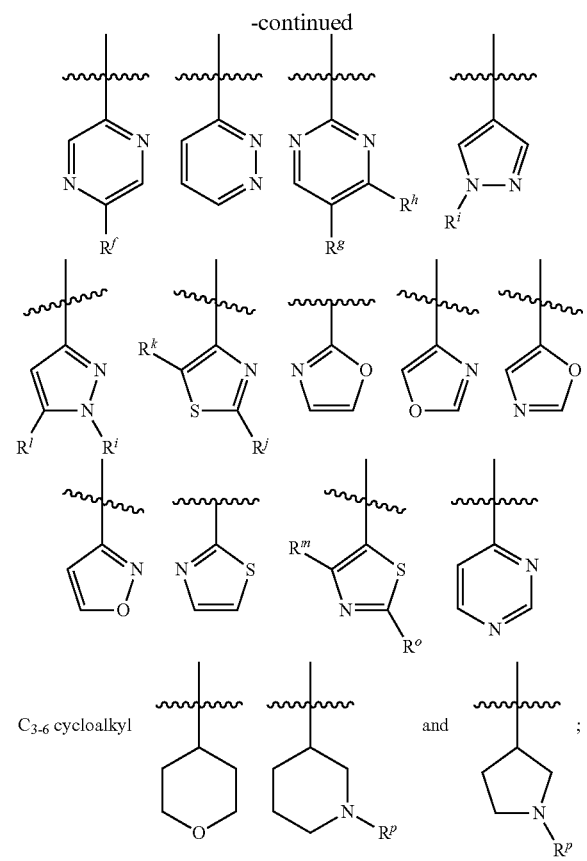

$R^a$, $R^c$ and $R^g$ are independently H or halo;
$R^d$ is H or alkoxy;
$R^e$ is H, $C_1$-$C_3$ alkyl or halo;
$R^b$, $R^f$, $R^h$, $R^i$, $R^j$, $R^k$, $R^l$, $R^m$, $R^n$, $R^o$ are independently H, $C_1$-$C_3$ alkyl or perhaloalkyl;
$R^p$ is H or C(O)OtBu; and
pharmaceutically acceptable salts of compounds of Formula (I).

(b) at least one pharmaceutically acceptable excipient.

An additional embodiment of the invention is a method of treating a subject suffering from or diagnosed with a disease, disorder, or medical condition mediated by P2X7 receptor activity, comprising administering to a subject in need of such treatment an effective amount of at least one compound selected from compounds of Formula (I) wherein:

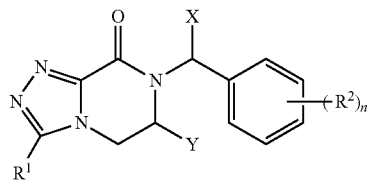

Formula (I)

$R^2$ is H, halo, $SO_2CH_3$, $C_{1-3}$ alkyl, $NO_2$, $NH_2$, perhaloalkyl or perhaloalkoxy; or two $R^2$ substituents are taken together to form:

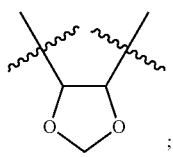 [SMILES: *C1OCOC1*]

n is 0-3;
X is H or $C_1$-$C_3$ alkyl;
Y is H, $C_1$-$C_3$ alkyl or $C_3$-$C_4$ cycloalkyl;
$R^1$ is selected from the group consisting of:

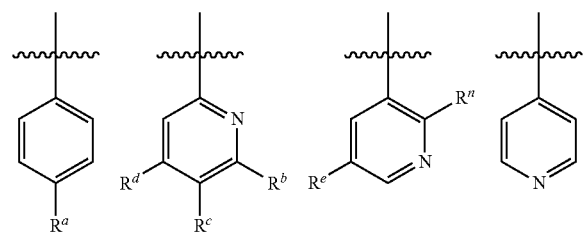

$R^a$, $R^c$ and $R^g$ are independently H or halo;
$R^d$ is H or alkoxy;
$R^e$ is H, $C_1$-$C_3$ alkyl or halo;
$R^b$, $R^f$, $R^h$, $R^i$, $R^j$, $R^k$, $R^l$, $R^m$, $R^n$, $R^o$ are independently H, $C_1$-$C_3$ alkyl or perhaloalkyl;
$R^p$ is H or C(O)OtBu; and
pharmaceutically acceptable salts of compounds of Formula (I).

In preferred embodiments of the inventive method, the disease, disorder, or medical condition is selected from: diseases of the autoimmune and inflammatory system such as: rheumatoid arthritis, osteoarthritis, psoriasis, septic shock, allergic dermatitis, asthma, allergic asthma, mild to severe asthma, steroid resistant asthma, idiopathic pulmonary fibrosis, allergic rhinitis, chronic obstructive pulmonary disease and airway hyper-responsiveness; diseases of the nervous and neuro-immune system such as acute and chronic pain states of neuropathic pain, inflammatory pain, spontaneous pain (diabetic neuropathy, postherpetic neuralgia, low back pain, chemotherapy-induced neuropathic pain, fibromyalgia) (Romagnoli, R, et. al., *Expert Opin. Ther. Targets,* 2008, 12(5), 647-661), and diseases involved with and without neuroinflammation of the CNS such as mood disorders (major depression, major depressive disorder, treatment resistant depression, bipolar disorder, anxious depression, anxiety) (Friedle, S A, et. al., *Recent Patents on CNS Drug Discovery,* 2010, 5, 35-45, Romagnoli, R, et. al., *Expert Opin. Ther. Targets,* 2008, 12(5), 647-661), cognition, sleep disorders, multiple sclerosis (Sharp, A J, et. al., J Neuroinflammation. 2008 Aug. 8; 5:33, Oyanguren-Desez O, et. al., *Cell Calcium.* 2011 November; 50(5):468-72, Grygorowicz, T, et. al., *Neurochem Int.* 2010 December; 57(7):823-9), epileptic seizures (Engel, T, et. al., *FASEB J.*

2012 April; 26(4):1616-28, Kim, J E, et. al. *Neurol Res.* 2009 November; 31(9):982-8, Avignone, E, et. al., *J Neurosci.* 2008 Sep. 10; 28(37):9133-44), Parkinson's disease (Marcellino, D, et. al., *J Neural Transm.* 2010 June; 117(6): 681-7), schizophrenia, Alzheimer's disease (Diaz-Hernandez J I, et. al., *Neurobiol Aging.* 2012 August; 33(8):1816-28, Delarasse C, *J Biol Chem.* 2011 Jan. 28; 286(4):2596-606, Sanz J M, et. al., *J Immunol.* 2009 Apr. 1; 182(7):4378-85), Huntington's disease (Diaz-Hernández M, et. Al., *FASEB J.* 2009 June; 23(6):1893-906), autism, spinal cord injury and cerebral ischemia/traumatic brain injury (Chu K, et. al., *J Neuroinflammation.* 2012 Apr. 18; 9:69, Arbeloa J, et. al, *Neurobiol Dis.* 2012 March; 45(3):954-61).

P2X7 antagonism may also be beneficial in several stress-related disorders. In addition, P2X7 intervention may be beneficial in diseases of the cardiovascular, metabolic, gastrointestinal and urogenital systems such as diabetes (*Arterioscler Thromb Vasc Biol.* 2004 July; 24(7):1240-5), thrombosis (Furlan-Freguia C, et. al., *J Clin Invest.* 2011 July; 121(7):2932-44), irritable bowel syndrome, Crohn's disease, ischemic heart disease, hypertension (Ji X, et. al., *Am J Physiol Renal Physiol.* 2012 October; 303(8):F1207-15), myocardial infarction, and lower urinary tract dysfunction such as incontinence. P2X7 antagonism may also present a novel therapeutic strategy for skeletal disorders, namely osteoporosis/osteopetrosis and may also modulate secretory function of exocrine glands. It is also hypothesized that blocking P2X7 may also be beneficial in glaucoma, interstitial cystitis (Martins J P, et. al., *Br J Pharmacol.* 2012 January; 165(1):183-96) and lower urinary tract syndrome (*Br J Pharmacol.* 2012 January; 165(1):183-96), IBD/IBS (*J Immunol.* 2011 Aug. 1; 187(3):1467-74. Epub 2011 Jun. 22), Sleep, RA/OA, Cough/COPD/asthma, cardiovascular disease, GN, ureteric obstruction, diabetes mellitus, hypertension, sepsis, ischaemia, Amyotrophic Lateral Sclerosis, Chaga's Disease, Chlamydia, Neuroblastoma, Tuberculosis, Polycystic Kidney Disease, and migraine.

An additional embodiment of the invention is a method of treating a subject suffering from or diagnosed with a disease, disorder, or medical condition mediated by P2X7 receptor activity, wherein the disease, disorder, or medical condition is selected from the group consisting of: rheumatoid arthritis, osteoarthritis, psoriasis, septic shock, allergic dermatitis, asthma, allergic asthma, mild to severe asthma, steroid resistant asthma, idiopathic pulmonary fibrosis, allergic rhinitis, chronic obstructive pulmonary disease (COPD) and airway hyper-responsiveness; diseases of the nervous and neuro-immune system such as acute and chronic pain states of neuropathic pain, inflammatory pain, spontaneous pain (diabetic neuropathy, postherpetic neuralgia, low back pain, chemotherapy-induced neuropathic pain, fibromyalgia); diseases involved with and without neuroinflammation of the CNS such as mood disorders (major depression, major depressive disorder, treatment resistant depression, bipolar disorder, anxious depression, anxiety), cognition, sleep disorders, multiple sclerosis, epileptic seizures, Parkinson's disease, schizophrenia, Alzheimer's disease, Huntington's disease, autism, spinal cord injury and cerebral ischemia/traumatic brain injury, stress-related disorders; diseases of the cardiovascular, metabolic, gastrointestinal and urogenital systems such as diabetes, diabetes mellitus, thrombosis, irritable bowel syndrome, IBD, Crohn's disease, ischemic heart disease, ischaemia, hypertension, cardiovascular disease, myocardial infarction, and lower urinary tract dysfunction such as incontinence, lower urinary tract syndrome, Polycystic Kidney Disease, Glomerulonephritis, (GN); skeletal disorders, namely osteoporosis/osteopetrosis: and glaucoma, interstitial cystitis, cough, ureteric obstruction, sepsis, Amyotrophic Lateral Sclerosis, Chaga's Disease, chlamydia, neuroblastoma, Tuberculosis, and migraine.

An additional embodiment of the invention is a method of treating a subject suffering from or diagnosed with a disease, disorder, or medical condition mediated by P2X7 receptor activity wherein the disease, disorder or medical condition is treatment resistant depression.

Additional embodiments, features, and advantages of the invention will be apparent from the following detailed description and through practice of the invention.

The invention may be more fully appreciated by reference to the following description, including the following glossary of terms and the concluding examples. For the sake of brevity, the disclosures of the publications, including patents, cited in this specification are herein incorporated by reference.

As used herein, the terms "including", "containing" and "comprising" are used herein in their open, non-limiting sense.

The term "alkyl" refers to a straight- or branched-chain alkyl group having from 1 to 12 carbon atoms in the chain. Examples of alkyl groups include methyl (Me, which also may be structurally depicted by the symbol, "/"), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples. The term $C_1$-$C_3$ alkyl as used here refers to a straight- or branched-chain alkyl group having from 1 to 3 carbon atoms in the chain.

The term "alkoxy" includes a straight chain or branched alkyl group with a terminal oxygen linking the alkyl group to the rest of the molecule. Alkoxy includes methoxy, ethoxy, propoxy, isopropoxy, butoxy, t-butoxy, pentoxy and so on.

The term "cycloalkyl" refers to a saturated carbocycle having from 3 to 6 ring atoms per carbocycle. Illustrative examples of cycloalkyl groups include the following entities, in the form of properly bonded moieties:

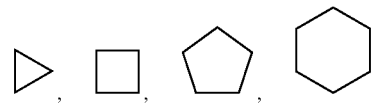

The term "$C_3$-$C_6$ cycloalkyl" as used here refers to a saturated carbocycle having from 3 to 6 ring atoms. The term "$C_3$-$C_4$ cycloalkyl" as used here refers to a saturated carbocycle having from 3 to 4 ring atoms.

A "heterocycloalkyl" refers to a monocyclic ring structure that is saturated and has from 4 to 6 ring atoms per ring structure selected from carbon atoms and one heteroatom selected from nitrogen and oxygen. Illustrative entities, in the form of properly bonded moieties, include:

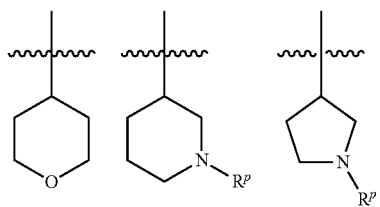

The term "aryl" refers to a monocyclic, aromatic carbocycle (ring structure having ring atoms that are all carbon) having 6 atoms per ring. (Carbon atoms in the aryl groups are sp² hybridized.)

The term "phenyl" represents the following moiety:

The term "heteroaryl" refers to a monocyclic or fused bicyclic heterocycle (ring structure having ring atoms selected from carbon atoms and up to four heteroatoms selected from nitrogen, oxygen, and sulfur) having from 3 to 9 ring atoms per heterocycle. Illustrative examples of heteroaryl groups include the following entities, in the form of properly bonded moieties:

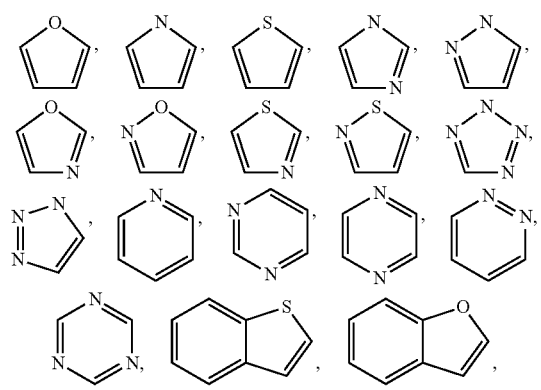

Those skilled in the art will recognize that the species of heteroaryl, cycloalkyl, aryl and heterocycloalkyl groups listed or illustrated above are not exhaustive, and that additional species within the scope of these defined terms may also be selected.

The term "halo" represents chloro, fluoro, bromo or iodo.

The term "perhaloalkyl" refers to a straight- or branched-chain alkyl group having from 1 to 4 carbon atoms in the chain optionally substituting hydrogens with halogens. Examples of perhaloalkyl groups include trifluoromethyl ($CF_3$), difluoromethyl ($CF_2H$), monofluoromethyl ($CH_2F$), pentafluoroethyl ($CF_2CF_3$), tetrafluoroethyl ($CHFCF_3$), trifluoroethyl ($CH_2CF_3$), tetrafluorotrifluoromethylethyl (—$CF(CF_3)_2$), and groups that in light of the ordinary skill in the art and the teachings provided herein would be considered equivalent to any one of the foregoing examples.

The term "perhaloalkoxy" refers to a straight- or branched-chain alkoxy group having from 1 to 4 carbon atoms in the chain optionally substituting hydrogens with halogens. Examples of perhaloalkoxy groups include trifluoromethoxy ($OCF_3$), difluoromethoxy ($OCF_2H$), monofluoromethoxy ($OCH_2F$), pentafluoroethoxy ($OCF_2CF_3$), tetrafluoroethoxy ($OCHFCF_3$), monofluoroethoxy ($OCH_2CH_2F$), trifluoroethoxy ($OCH_2CF_3$), tetrafluorotrifluoromethylethoxy (—$OCF(CF_3)_2$), and groups that in light of the ordinary skill in the art and the teachings provided herein would be considered equivalent to any one of the foregoing examples.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system. In cases where a specified moiety or group is not expressly noted as being optionally substituted or substituted with any specified substituent, it is understood that such a moiety or group is intended to be unsubstituted.

The terms "para", "meta", and "ortho" have the meanings as understood in the art. Thus, for example, a fully substituted phenyl group has substituents at both "ortho" (o) positions adjacent to the point of attachment of the phenyl ring, both "meta" (m) positions, and the one "para" (p) position across from the point of attachment. To further clarify the position of substituents on the phenyl ring, the 2 different ortho positions will be designated as ortho and ortho' and the 2 different meta positions as meta and meta' as illustrated below.

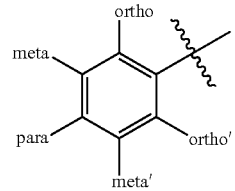

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

The terms "buffered" solution or "buffer" solution are used herein interchangeably according to their standard meaning. Buffered solutions are used to control the pH of a medium, and their choice, use, and function is known to those of ordinary skill in the art. See, for example, G. D. Considine, ed., Van Nostrand's Encyclopedia of Chemistry, p. 261, 5th ed. (2005), describing, inter alia, buffer solutions and how the concentrations of the buffer constituents relate to the pH of the buffer. For example, a buffered solution is obtained by adding $MgSO_4$ and $NaHCO_3$ to a solution in a 10:1 w/w ratio to maintain the pH of the solution at about 7.5.

Any formula given herein is intended to represent compounds having structures depicted by the structural formula as well as certain variations or forms. In particular, compounds of any formula given herein may have asymmetric centers and therefore exist in different enantiomeric forms. All optical isomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers.

It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers."

Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture."

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenyl nitromethane, that are likewise formed by treatment with acid or base.

Tautomeric forms may be relevant to the attainment of the optimal chemical reactivity and biological activity of a compound of interest.

Compounds of the invention may also exist as "rotamers," that is, conformational isomers that occur when the rotation leading to different conformations is hindered, resulting a rotational energy barrier to be overcome to convert from one conformational isomer to another.

The compounds of this invention may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

Certain examples contain chemical structures that are depicted as an absolute enantiomer but are intended to indicate enatiopure material that is of unknown configuration. In these cases (R*) or (S*) is used in the name to indicate that the absolute stereochemistry of the corresponding stereocenter is unknown. Thus, a compound designated as (R*) refers to an enantiopure compound with an absolute configuration of either (R) or (S). In cases where the absolute stereochemistry has been confirmed, the structures are named using (R) and (S).

The symbols  and  are used as meaning the same spatial arrangement in chemical structures shown herein. Analogously, the symbols  and  are used as meaning the same spatial arrangement in chemical structures shown herein.

Additionally, any formula given herein is intended to refer also to hydrates, solvates, and polymorphs of such compounds, and mixtures thereof, even if such forms are not listed explicitly. Certain compounds of Formula (I) or pharmaceutically acceptable salts of compounds of Formula (I) may be obtained as solvates. Solvates include those formed from the interaction or complexation of compounds of the invention with one or more solvents, either in solution or as a solid or crystalline form. In some embodiments, the solvent is water and then the solvates are hydrates. In addition, certain crystalline forms of compounds of Formula (I) or pharmaceutically acceptable salts of compounds of Formula (I) may be obtained as co-crystals. In certain embodiments of the invention, compounds of Formula (I) were obtained in a crystalline form. In other embodiments, crystalline forms of compounds of Formula (I) were cubic in nature. In other embodiments, pharmaceutically acceptable salts of compounds of Formula (I) were obtained in a crystalline form. In still other embodiments, compounds of Formula (I) were obtained in one of several polymorphic forms, as a mixture of crystalline forms, as a polymorphic form, or as an amorphous form. In other embodiments, compounds of Formula (I) convert in solution between one or more crystalline forms and/or polymorphic forms.

Reference to a compound herein stands for a reference to any one of: (a) the actually recited form of such compound, and (b) any of the forms of such compound in the medium in which the compound is being considered when named. For example, reference herein to a compound such as R—COOH, encompasses reference to any one of, for example, R—COOH$_{(s)}$, R—COOH$_{(sol)}$, and R—COO$^-_{(sol)}$. In this example, R—COOH$_{(s)}$ refers to the solid compound, as it could be for example in a tablet or some other solid pharmaceutical composition or preparation; R—COOH$_{(sol)}$ refers to the undissociated form of the compound in a solvent; and R—COO$^-_{(sol)}$ refers to the dissociated form of the compound in a solvent, such as the dissociated form of the compound in an aqueous environment, whether such dissociated form derives from R—COOH, from a salt thereof, or from any other entity that yields R—COO$^-$ upon dissociation in the medium being considered. In another example, an expression such as "exposing an entity to compound of formula R—COOH" refers to the exposure of such entity to the form, or forms, of the compound R—COOH that exists, or exist, in the medium in which such exposure takes place. In still another example, an expression such as "reacting an entity with a compound of formula R—COOH" refers to the reacting of (a) such entity in the chemically relevant form, or forms, of such entity that exists, or exist, in the medium in which such reacting takes place, with (b) the chemically relevant form, or forms, of the compound R—COOH that exists, or exist, in the medium in which such reacting takes place. In this regard, if such entity is for example in an aqueous environment, it is understood that the compound R—COOH is in such same medium, and therefore the entity is being exposed to species such as R—COOH$_{(aq)}$ and/or R—COO$^-_{(aq)}$, where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation, and deprotonation. No further examples in this regard are provided herein because these interactions and transformations in a given medium are known by any one of ordinary skill in the art.

In another example, a zwitterionic compound is encompassed herein by referring to a compound that is known to form a zwitterion, even if it is not explicitly named in its zwitterionic form. Terms such as zwitterion, zwitterions, and their synonyms zwitterionic compound(s) are standard IUPAC-endorsed names that are well known and part of standard sets of defined scientific names. In this regard, the name zwitterion is assigned the name identification CHEBI: 27369 by the Chemical Entities of Biological Interest (ChEBI) dictionary of molecular entities. As generally well known, a zwitterion or zwitterionic compound is a neutral compound that has formal unit charges of opposite sign. Sometimes these compounds are referred to by the term "inner salts". Other sources refer to these compounds as "dipolar ions", although the latter term is regarded by still other sources as a misnomer. As a specific example, aminoethanoic acid (the amino acid glycine) has the formula $H_2NCH_2COOH$, and it exists in some media (in this case in neutral media) in the form of the zwitterion $^+H_3NCH_2COO^-$. Zwitterions, zwitterionic compounds, inner salts and dipolar ions in the known and well established meanings of these terms are within the scope of this invention, as would in any case be so appreciated by those of ordinary skill in the art. Because there is no need to name each and every embodiment that would be recognized by those of ordinary skill in the art, no structures of the zwitterionic compounds that are associated with the compounds of this invention are given explicitly herein. They are, however, part of the embodiments of this invention. No further examples in this regard are provided herein because the interactions and transformations in a given medium that lead to the various forms of a given compound are known by any one of ordinary skill in the art.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorus, fluorine, and chlorine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, $^{125}I$, respectively. Such isotopically labeled compounds are useful in metabolic studies (preferably with $^{14}C$), reaction kinetic studies (with, for example $^2H$ or $^3H$), detection or imaging techniques [such as positron emission tomography (PET) or single-photon emission computed tomography (SPECT)] including drug or substrate tissue distribution assays, or in radioactive treatment of patients. In particular, an $^{18}F$ or $^{11}C$ labeled compound may be particularly preferred for PET or SPECT studies. Further, substitution with heavier isotopes such as deuterium (i.e., $^2H$) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of the species for the same variable elsewhere in the formula, unless stated otherwise.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

The invention includes also pharmaceutically acceptable salts of the compounds of Formula (I), preferably of those described above and of the specific compounds exemplified herein, and methods of treatment using such salts.

Pharmaceutically acceptable means approved or approvable by a regulatory agency of Federal or a state government or the corresponding agency in countries other than the United States, or that is listed in the U. S. Pharmcopoeia or other generally recognized pharmacopoeia for use in animals, and more particularly, in humans.

A "pharmaceutically acceptable salt" is intended to mean a salt of a free acid or base of a compound represented by Formula (I) that is non-toxic, biologically tolerable, or otherwise biologically suitable for administration to the subject. It should possess the desired pharmacological activity of the parent compound. See, generally, G. S. Paulekuhn, et al., "Trends in Active Pharmaceutical Ingredient Salt Selection based on Analysis of the Orange Book Database", *J. Med. Chem.*, 2007, 50:6665-72, S. M. Berge, et al., "Pharmaceutical Salts", *J Pharm Sci.*, 1977, 66:1-19, and *Handbook of Pharmaceutical Salts, Properties, Selection, and Use*, Stahl and Wermuth, Eds., Wiley-VCH and VHCA, Zurich, 2002. Examples of pharmaceutically acceptable salts are those that are pharmacologically effective and suitable for contact with the tissues of patients without undue toxicity, irritation, or allergic response. A compound of Formula (I) may possess a sufficiently acidic group, a sufficiently basic group, or both types of functional groups, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

When the compound of Formula (I) contains a basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid, glutaric acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

When the compound of Formula (I) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as N-methyl-D-glucamine, lysine, choline, glycine and arginine, ammonia, carbonates, bicarbonates, primary, secondary, and tertiary amines, and cyclic amines, such as tromethamine, benzylamines, pyrrolidines, piperidine, morpholine, and piperazine, and inorganic salts derived from sodium, calcium, potassium, magnesium, manganese, iron, copper, zinc, aluminum, and lithium.

The invention also relates to pharmaceutically acceptable prodrugs of the compounds of Formula (I), and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I)). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "*Design of Prodrugs*", ed. H. Bundgaard, Elsevier, 1985.

Exemplary prodrugs include compounds having an amino acid residue, or a polypeptide chain of two or more (e.g., two, three or four) amino acid residues, covalently joined through an amide or ester bond to a free amino, hydroxy, or carboxylic acid group of a compound of Formula (I). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of Formula (I) as amides or alkyl esters. Examples of amides include those derived from ammonia, primary $C_{1-6}$alkyl amines and secondary di($C_{1-6}$alkyl) amines. Secondary amines include 5- or 6-membered heterocycloalkyl or heteroaryl ring moieties. Examples of amides include those that are derived from ammonia, $C_{1-3}$alkyl primary amines, and di($C_{1-2}$alkyl)amines. Examples of esters of the invention include $C_{1-7}$alkyl, $C_{5-7}$cycloalkyl, phenyl, and phenyl($C_{1-6}$alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in Fleisher et al., *Adv. Drug Delivery Rev.* 1996, 19, 115-130. Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in Robinson et al., *J Med Chem.* 1996, 39 (1), 10-18. Free amines can also be derivatized as amides, sulfonamides or phosphonamides. All of these prodrug moieties may incorporate groups including ether, amine, and carboxylic acid functionalities.

The present invention also relates to pharmaceutically active metabolites of the compounds of Formula (I), which may also be used in the methods of the invention. A "pharmaceutically active metabolite" means a pharmacologically active product of metabolism in the body of a compound of Formula (I) or salt thereof. Prodrugs and active metabolites of a compound may be determined using routine techniques known or available in the art. See, e.g., Bertolini, et al., *J Med Chem.* 1997, 40, 2011-2016; Shan, et al., *J Pharm Sci.* 1997, 86 (7), 765-767; Bagshawe, *Drug Dev Res.* 1995, 34, 220-230; Bodor, *Adv Drug Res.* 1984, 13, 225-331; Bundgaard, *Design of Prodrugs* (Elsevier Press, 1985); and Larsen, *Design and Application of Prodrugs* (Chapter 5), in 'Textbook of *Drug Design and Development*' (Krogsgaard-Larsen, et al., eds., Harwood Academic Publishers, 1991).

The compounds of Formula (I) and their pharmaceutically acceptable salts, pharmaceutically acceptable prodrugs, and pharmaceutically active metabolites of the present invention are useful as modulators of the P2X7 receptor in the methods of the invention. As such modulators, the compounds may act as antagonists, agonists, or inverse agonists. The term "modulators" include both inhibitors and activators, where "inhibitors" refer to compounds that decrease, prevent, inactivate, desensitize or down-regulate the P2X7 receptor expression or activity, and "activators" are compounds that increase, activate, facilitate, sensitize, or up-regulate P2X7 receptor expression or activity.

The term "treat", "treatment" or "treating" as used herein is intended to refer to administration of an active agent or composition of the invention to a subject for the purpose of affecting a therapeutic or prophylactic benefit through modulation of P2X7 receptor activity. Treating includes reversing, ameliorating, alleviating, inhibiting the progress of, lessening the severity of, or preventing a disease, disorder, or condition, or one or more symptoms of such disease, disorder or condition mediated through modulation of P2X7 receptor activity. The term "subject" refers to a mammalian patient in need of such treatment, such as a human.

Accordingly, the invention relates to methods of using the compounds described herein to treat subjects diagnosed with or suffering from a disease, disorder, or condition mediated by P2X7 receptor activity, such as: rheumatoid arthritis, osteoarthritis, psoriasis, septic shock, allergic dermatitis, asthma, allergic asthma, mild to severe asthma, steroid resistant asthma, idiopathic pulmonary fibrosis, allergic rhinitis, chronic obstructive pulmonary disease (COPD) and airway hyper-responsiveness; diseases of the nervous and neuro-immune system such as acute and chronic pain states of neuropathic pain, inflammatory pain, spontaneous pain (diabetic neuropathy, postherpetic neuralgia, low back pain, chemotherapy-induced neuropathic pain, fibromyalgia); diseases involved with and without neuroinflammation of the CNS such as mood disorders (major depression, major depressive disorder, treatment resistant depression, bipolar disorder, anxious depression, anxiety), cognition, sleep disorders, multiple sclerosis, epileptic seizures, Parkinson's disease, schizophrenia, Alzheimer's disease, Huntington's disease, autism, spinal cord injury and cerebral ischemia/traumatic brain injury, stress-related disorders; diseases of the cardiovascular, metabolic, gastrointestinal and urogenital systems such as diabetes, diabetes mellitus, thrombosis, irritable bowel syndrome, IBD, Crohn's disease, ischemic heart disease, ischaemia, hypertension, cardiovascular disease, myocardial infarction, and lower urinary tract dysfunction such as incontinence, lower urinary tract syndrome, Polycystic Kidney Disease, Glomerulonephritis, (GN); skeletal disorders, namely osteoporosis/osteopetrosis: and glaucoma, interstitial cystitis, cough, ureteric obstruction, sepsis, Amyotrophic Lateral Sclerosis, Chaga's Disease, chlamydia, neuroblastoma, Tuberculosis, and migraine.

In treatment methods according to the invention, an effective amount of a pharmaceutical agent according to the invention is administered to a subject suffering from or diagnosed as having such a disease, disorder, or condition. An "effective amount" means an amount or dose sufficient to generally bring about the desired therapeutic or prophylactic benefit in patients in need of such treatment for the designated disease, disorder, or condition. Effective amounts or doses of the compounds of the present invention may be ascertained by routine methods such as modeling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician. An example of a dose is in the range of from about 0.001 to about 200 mg of compound per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 0.2 to about 2.5 g/day.

Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the active agents of the invention may be used in combination with additional active ingredients in the treatment of the above conditions. The additional active ingredients may be coadministered separately with an active agent of compounds of Table 1 or included with such an agent in a pharmaceutical composition according to the invention. In an exemplary embodiment, additional active ingredients are those that are known or discovered to be effective in the treatment of conditions, disorders, or diseases mediated by P2X7 activity, such as another P2X7 modulator or a compound active against another target associated with the particular condition, disorder, or disease. The combination may serve to increase efficacy (e.g., by including in the combination a compound potentiating the potency or effectiveness of an active agent according to the invention), decrease one or more side effects, or decrease the required dose of the active agent according to the invention.

The active agents of the invention are used, alone or in combination with one or more additional active ingredients, to formulate pharmaceutical compositions of the invention. A pharmaceutical composition of the invention comprises: (a) an effective amount of at least one active agent in accordance with the invention; and (b) a pharmaceutically acceptable excipient.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the active agents may be prepared using suitable pharmaceutical excipients and compounding techniques known or that become available to those skilled in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the compounds of the invention can be provided in the form of tablets or capsules, or as a solution, emulsion, or suspension. To prepare the oral compositions, the compounds may be formulated to yield a dosage of, e.g., from about 0.05 to about 100 mg/kg daily, or from about 0.05 to about 35 mg/kg daily, or from about 0.1 to about 10 mg/kg daily. For example, a total daily dosage of about 5 mg to 5 g daily may be accomplished by dosing once, twice, three, or four times per day.

Oral tablets may include a compound according to the invention mixed with pharmaceutically acceptable excipients such as inert diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are suitable disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, compounds of the invention may be mixed with a solid, semi-solid, or liquid diluent. Soft gelatin capsules may be prepared by mixing the compound of the invention with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For example, the compositions may be formulated for rectal administration as a suppository. For parenteral use, including intravenous, intramuscular, intraperitoneal, or subcutaneous routes, the compounds of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses may range from about 1 to 1000 μg/kg/minute of compound, admixed with a pharmaceutical carrier over a period ranging from several minutes to several days.

For topical administration, the compounds may be mixed with a pharmaceutical carrier at a concentration of about 0.1% to about 10% of drug to vehicle. Another mode of administering the compounds of the invention may utilize a patch formulation to affect transdermal delivery.

Compounds of the invention may alternatively be administered in methods of this invention by inhalation, via the nasal or oral routes, e.g., in a spray formulation also containing a suitable carrier.

Exemplary compounds useful in methods of the invention will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I). Reactions may be performed between the melting point and the reflux temperature of the solvent, and preferably between 0° C. and the reflux temperature of the solvent. Reactions may be heated employing conventional heating or microwave heating. Reactions may also be conducted in sealed pressure vessels above the normal reflux temperature of the solvent.

Abbreviations and acronyms used herein include the following:

| Term | Acronym |
|---|---|
| High-pressure liquid chromatography | HPLC or hplc |
| Diisopropylethylamine | DIPEA |
| Tetrahydrofuran | THF |
| tert-Butylcarbamoyl | boc or Boc |
| Dichloromethane | DCM |
| Trifluoroacetic acid | TFA |
| Acetic Acid | AcOH |
| N,N-Dimethylformamide | DMF |
| Methanol | MeOH |
| Isopropanol | IPA or iPrOH |
| Ethanol | EtOH |
| Acetonitrile | ACN or MeCN |
| Ethyl Acetate | EtOAc, or EA or Et(OAc) |
| Triethylamine | TEA |
| Dichloroethane | DCE |
| Room temperature | rt or RT |
| Supercritical Fluid Chromatography | SFC |
| gigabecquerel | GBq |
| 2,4-Bis(4-methoxyphenyl)-2,4-dithioxo-1,3,2,4-dithiadiphosphetane | Lawesson's reagent |
| Tetrakis(triphenylphosphine)palladium(0) | Pd(Ph$_3$)$_4$ |
| Hour or hours | h |
| 5% palladium on calcium carbonate; poisoned with lead. | Lindlar catalyst |

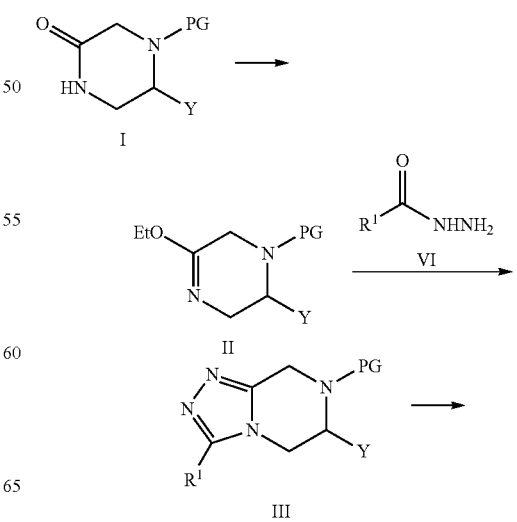

Scheme 1

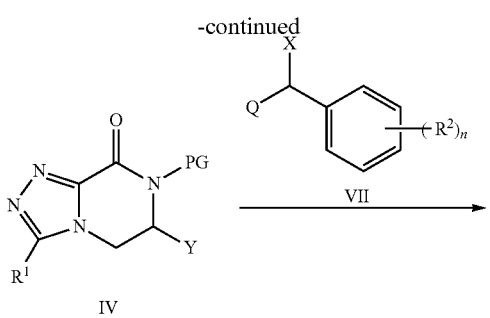

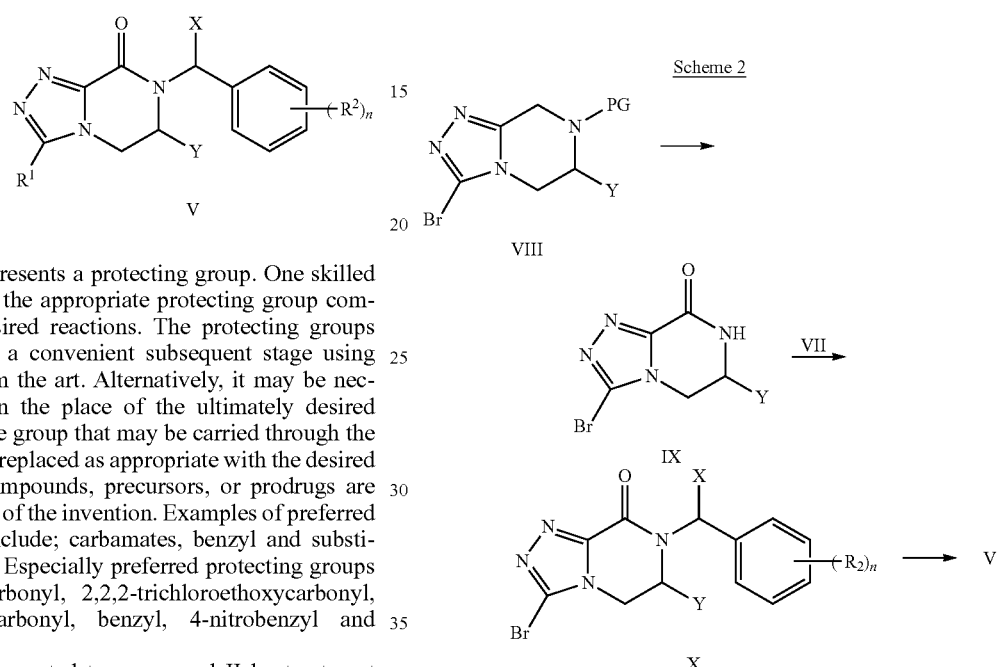

The group PG represents a protecting group. One skilled in the art will select the appropriate protecting group compatible with the desired reactions. The protecting groups may be removed at a convenient subsequent stage using methods known from the art. Alternatively, it may be necessary to employ, in the place of the ultimately desired substituent, a suitable group that may be carried through the reaction scheme and replaced as appropriate with the desired substituent. Such compounds, precursors, or prodrugs are also within the scope of the invention. Examples of preferred protecting groups include; carbamates, benzyl and substituted benzyl groups. Especially preferred protecting groups are; tert-butyloxycarbonyl, 2,2,2-trichloroethoxycarbonyl, alpha-chloroethoxycarbonyl, benzyl, 4-nitrobenzyl and diphenylmethyl.

Compound I is converted to compound II by treatment with triethyloxonium tetrafluoroborate in DCM. Compound II is then converted to bicycle III upon heating with hydrazide VI in a solvent such as 1-butanol at a temperature of approximately 130° C. for approximately 16 hours. Oxidation of bicycle III in a solvent such as 1:1 CHCl$_3$:ACN, with ruthenium (IV) oxide hydrate and sodium metaperiodate in water provides compound IV. After removal of the protecting group, compound IV is then converted to compound V by treatment with compound VII, where Q is a leaving group such as a bromine or chlorine, X is H or CH$_3$, and a base such as Cs$_2$CO$_3$ in a solvent such as DMF. Compound V, where R$^2$ is NO$_2$ is reduced to Compound V, where R$^2$ is NH$_2$ upon treatment of the aryl nitro compound with zinc dust in a solvent such as acetone and water. The hydrazides R$^1$—NH$_2$NH$_2$ that are not commercially available were, in general, prepared by addition of hydrazine monohydrate in EtOH to the appropriately activated carboxylic acid (R$^1$—CO$_2$H) or carboxylic ester (R$^1$—CO$_2$alkyl). The carboxylic acids (R$^1$—CO$_2$H) are prepared from the corresponding nitrile (R$^1$—CN) using standard hydrolysis conditions such as concentrated HCl in MeOH at reflux for approximately 2 hours.

Bromide VIII is converted to compound IX through oxidation with RuO$_2$ and NaIO$_4$ as described in Scheme I for the conversion of compound III to compound IV. After removal of the protecting group, compound IX is converted to compound X by treatment with compound VII using the conditions described for the conversion of compound IV to compound V. Compound X is then converted to compound V upon treatment with the appropriate boronic acid (R$^1$—B(OH)$_2$, Pd(Ph$_3$)$_4$, and 1M Na$_2$CO$_3$ in a solvent such as dioxane with heating to about 100° C.

Scheme 3

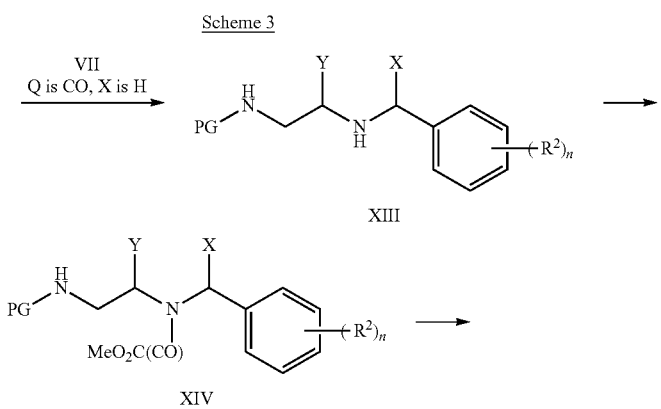

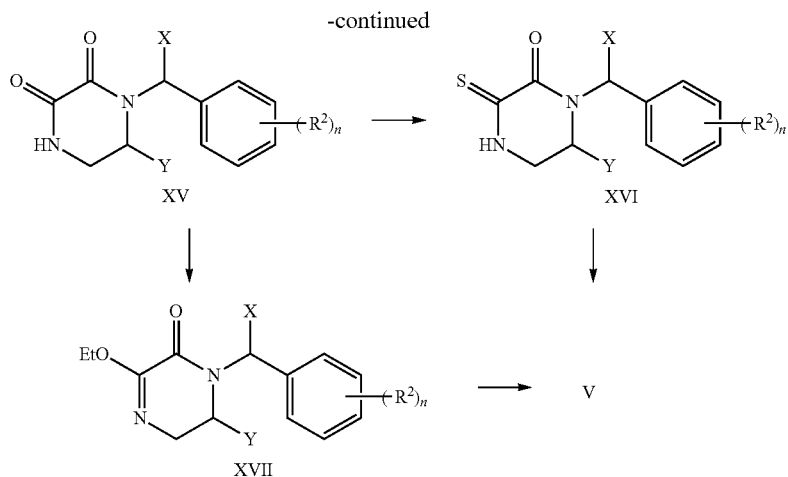

Reductive amination with amine XII and aldehyde VII, where Q is CO and X is H, is accomplished using a reducing agent such as Na(OAc)$_3$BH in a solvent such as DCE or DCM, to provide compound XIII. Treatment of this compound with methyl chlorooxoacetate in DCM with TEA provides compound XIV. Compound XIV is then converted to compound XV, by initial removal of the protecting group, followed by treatment with a base such as TEA or DIPEA in a solvent such as DCM or DMF. Upon treatment with Lawesson's reagent as described in Scheme I for the conversion of compound I to compound II, dione XV is converted to compound XVI. Compound XVI is converted to compound V by treatment with the appropriate hydrazide as described in Scheme I in the conversion of compound II to compound III. Alternatively, Compound XV is converted to compound XVII when treated with triethyloxonium tetrafluroborate in DCM. Compound V is then obtained by treatment of compound XVII with the appropriate hydrazide in a solvent such as 1-butanol at a temperature of approximately 130° C. for approximately 16 hours.

ment with NaN$_3$ in DMF with heating to approximately 70° C. for approximately 18 h. The azide is then reduced to amine XX using catalytic hydrogenation conditions of hydrogen gas, a metal catalyst such as 10% Pd/C in a solvent such as Et(OAc) or EtOH. Compound XX is converted to compound XXI by treatment with methyl chlorooxoacetate in a solvent such as DCM or DMF and a base such as TEA or DIPEA. Compound XV is then prepared from compound XXI by initial removal of the protecting group and reductive amination of the resulting amine (not shown) with aldehyde VII, where Q is CO and X is H, using a reducing agent such as Na(OAc)$_3$BH in a solvent such as DCE or DCM. Compound XX is converted to compound XIX by treatment with chloroacetyl chloride in a solvent such as DCM and a base such as TEA. Compound I is then prepared from compound XIX by initial removal of the protecting group and treatment with a base such as sodium carbonate in a solvent such as THF.

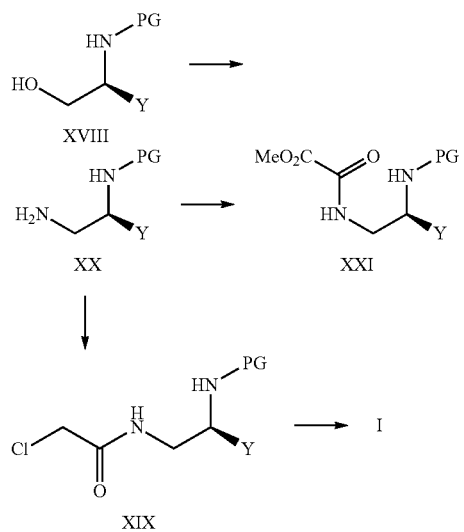

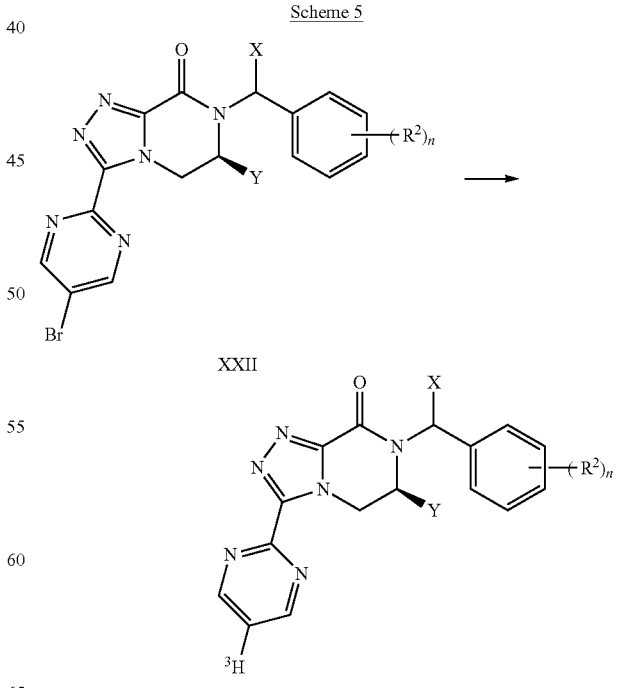

Alcohol XVIII is converted to amine XX by initial treatment of alcohol XVIII with mesyl chloride in a solvent such as DCM, DCE or ether with a base such as TEA or DIPEA. The resulting mesylate (not shown) is then converted to the corresponding azide (not shown) upon treat- Bromide XXII is converted to tritiated compound XXIII upon treatment of XXII with a base such as DIPEA, a metal catalyst such as Lindlar Catalyst under $^3H_2$-atmosphere in a solvent such as EtOH.

EXAMPLES

Chemistry

In obtaining the compounds described in the examples below and the corresponding analytical data, the following experimental and analytical protocols were followed unless otherwise indicated.

Unless otherwise stated, reaction mixtures were magnetically stirred at room temperature (rt) under a nitrogen atmosphere. Where solutions were "dried," they were generally dried over a drying agent such as $Na_2SO_4$ or $MgSO_4$. Where mixtures, solutions, and extracts were "concentrated", they were typically concentrated on a rotary evaporator under reduced pressure. Reactions under microwave irradiation conditions were carried out in a Biotage Initiator or CEM Discover instrument.

Normal-phase flash column chromatography (FCC) was performed on silica gel ($SiO_2$) using prepackaged cartridges, eluting with the indicated solvents.

Preparative reverse-phase high performance liquid chromatography (HPLC) was performed on a Agilent HPLC with an Xterra Prep $RP_{18}$ (5 μm, 30×100 mm, or 50×150 mm) column, and a gradient of 10 to 99% acetonitrile/water (20 mM $NH_4OH$) over 12 to 18 min, and a flow rate of 30 or 80 mL/min, unless otherwise indicated.

Preparative supercritical fluid high performance liquid chromatography (SFC) was performed either on a JASCO preparative SFC system, an APS 1010 system from Berger instruments, or a SFC-PICLAB-PREP 200 (PIC SOLUTION, Avignon, France). The separations were conducted between at 100-150 bar with a flow rate ranging from 40-60 mL/min. The columns used were heated to 35-40° C.

Mass spectra (MS) were obtained on an Agilent series 1100 MSD using electrospray ionization (ESI) in positive mode unless otherwise indicated. Calculated (calcd.) mass corresponds to the exact mass.

Nuclear magnetic resonance (NMR) spectra were obtained on Bruker model DRX spectrometers. The format of the $^1H$ NMR data below is: chemical shift in ppm downfield of the tetramethylsilane reference (multiplicity, coupling constant J in Hz, integration).

Chemical names were generated using ChemDraw Ultra 6.0.2 (CambridgeSoft Corp., Cambridge, Mass.) or ACD/Name Version 9 (Advanced Chemistry Development, Toronto, Ontario, Canada).

Intermediate 1. 3-(pyrazin-2-yl)-6,7-dihydro-[1,2,4]triazolo[4,3-a]pyrazin-8(5H)-one

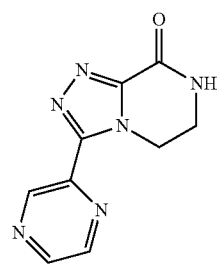 [SMILES: O=C1NCCn2c1nnc2-c1cnccn1]

Step A. tert-butyl 3-ethoxy-5,6-dihydropyrazine-1(2H)-carboxylate

To a solution of tert-butyl 3-oxopiperazine-1-carboxylate (1 g, 5 mmol) in DCM (15 mL) was added triethyloxonium tetrafluoroborate (2.9 g, 15 mmol). Stirred for 2 h and neutralized with sat. aq $NaHCO_3$. Layers separated and aqueous layer extracted with DCM. Combined organic layers dried over $Na_2SO_4$, filtered, and concentrated to give the title compound, which was used directly without further purification.

Step B. tert-butyl 3-(pyrazin-2-yl)-5,6-dihydro-[1,2,4]triazolo[4,3-a]pyrazine-7(8H)-carboxylate To a solution of tert-butyl 3-ethoxy-5,6-dihydropyrazine-1(2H)-carboxylate (1.14 g, 5 mmol) in 1-butanol (30 mL) was added pyrazine-2-carbohydrazide (685 mg, 5 mmol). The reaction mixture was heated at reflux for 16 h. After cooling to rt, the reaction mixture was concentrated and purified by chromatography ($SiO_2$; 2.5% MeOH in DCM) to afford the desired product as a white solid (700 mg, 50% over 2 steps). MS (ESI): mass calcd. for $C_{14}H_{18}N_6O_2$, 302.2; m/z found, 303.2 $[M+H]^+$. 1H NMR (500 MHz, $CDCl_3$) d 9.57 (d, J=1.4 Hz, 1H), 8.62 (d, J=2.5 Hz, 1H), 8.59-8.54 (m, 1H), 4.94 (s, 2H), 4.63-4.50 (m, 2H), 3.89 (t, J=5.4 Hz, 2H), 1.51 (s, 9H).

Step C. 3-(pyrazin-2-yl)-5,6,7,8-tetrahydro-[1,2,4]triazolo[4,3-a]pyrazine

To a solution of tert-butyl 3-(pyrazin-2-yl)-5,6-dihydro-[1,2,4]triazolo[4,3-a]pyrazine-7(8H)-carboxylate (9.3 g, 30 mmol) in DCM (100 mL) was added 1.25M HCl in EtOH (30 mL, 37.5 mmol). After 3 h, the reaction mixture was concentrated, and the resulting solid was purified by chromatography ($SiO_2$; 10% MeOH in DCM) to provide the desired product as a white solid (3.7 g, 61%). MS (ESI): mass calcd. for $C_9H_{10}N_6$, 202.1; m/z found, 203.1 $[M+H]^+$. $^1H$ NMR (400 MHz, $CD_3OD$) δ 9.35 (d, J=1.4 Hz, 1H), 8.72 (dd, J=2.5, 1.6 Hz, 1H), 8.66 (d, J=2.6 Hz, 1H), 4.50 (t, J=5.6 Hz, 2H), 4.22 (s, 2H), 3.24 (t, J=5.6 Hz, 2H).

Step D. 2-(trimethylsilyl)ethyl 3-(pyrazin-2-yl)-5,6-dihydro-[1,2,4]triazolo[4,3-a]pyrazine-7(8H)-carboxylate To a solution of 3-(pyrazin-2-yl)-5,6,7,8-tetrahydro-[1,2,4]triazolo[4,3-a]pyrazine (1.0 g, 5.0 mmol) and N,N-diisopropylethylamine (1.7 mL, 9.9 mmol) in DMF (15 mL) was added 1-[2-(trimethylsilyl)ethoxycarbonyloxy]pyrrolidin-2,5-dione (1.5 g, 5.9 mmol). Stirred for 18 h and poured into ice cold brine (150 mL). Precipitate filtered and washed successively with water and ether to afford the desired product as a white solid (1.5 g, 89%). MS (ESI): mass calcd. for $C_{15}H_{22}N_6O_2Si$, 346.2; m/z found, 347.2 $[M+H]^+$. $^1H$ NMR (500 MHz, $CDCl_3$) δ 9.50 (d, J=1.4 Hz, 1H), 8.56 (d, J=2.5 Hz, 1H), 8.52-8.48 (m, 1H), 4.91 (s, 2H), 4.60-4.45 (m, 2H), 4.25-4.14 (m, 2H), 3.87 (t, J=5.3 Hz, 2H), 1.07-0.92 (m, 2H), 0.01--0.04 (m, 9H).

Step E. 2-(trimethylsilyl)ethyl 8-oxo-3-(pyrazin-2-yl)-5,6-dihydro-[1,2,4]triazolo[4,3-a]pyrazine-7(8H)-carboxylate To a vigorously stirred solution of 2-(trimethylsilyl)ethyl 3-(pyrazin-2-yl)-5,6-dihydro-[1,2,4]triazolo[4,3-a]pyrazine- 7(8H)-carboxylate (172 mg, 0.5 mmol) in 1:1 CHCl₃:MeCN (3.8 mL) was added a solution of ruthenium (IV) oxide hydrate (9.8 mg, 0.07 mmol) and sodium metaperiodate (504 mg, 2.3 mmol) in water (4.7 mL). After 4 h, the reaction mixture was diluted with water and extracted with CHCl₃ (×3). The combined organic extracts were dried (Na₂SO₄), filtered, and concentrated to afford a green oil. Purification by chromatography (SiO₂; EtOAc-10% IPA/EtOAc) provided the desired product as a white solid (663 mg, 63%). MS (ESI): mass calcd. for $C_{15}H_{20}N_6O_3Si$, 360.1; m/z found, 361.2 [M+H]⁺. ¹H NMR (500 MHz, CDCl₃) δ 9.59 (d, J=1.5 Hz, 1H), 8.63 (d, J=2.5 Hz, 1H), 8.55 (dd, J=2.5, 1.6 Hz, 1H), 4.88-4.75 (m, 2H), 4.47-4.33 (m, 2H), 4.33-4.24 (m, 2H), 1.18-1.04 (m, 2H), 0.04-(−0.02) (m, 9H).

Step F. 3-(pyrazin-2-yl)-6,7-dihydro-[1,2,4]triazolo[4,3-a]pyrazin-8(5H)-one

To a solution of 2-(trimethylsilyl)ethyl 8-oxo-3-(pyrazin-2-yl)-5,6-dihydro-[1,2,4]triazolo[4,3-a]pyrazine-7(8H)-carboxylate (1.0 g, 2.9 mmol) in DCM (29 mL) was added TFA (5.7 mL, 75 mmol). After 1 h, the reaction mixture was concentrated. The crude residue was diluted with EtOAc, sonicated, and filtered to provide the desired product as a white solid (1.2 g, 95%). MS (ESI): mass calcd. for $C_9H_8N_6O$, 216.1; m/z found, 217.1 [M+H]⁺. ¹H NMR (500 MHz, DMSO-d₆) δ 9.39 (d, J=1.1 Hz, 1H), 8.77 (q, J=2.6 Hz, 2H), 8.56 (s, 1H), 4.73-4.60 (m, 2H), 3.67-3.55 (m, 2H).

Intermediate 2. 3-(pyridin-2-yl)-6,7-dihydro-[1,2,4]triazolo[4,3-a]pyrazin-8(5H)-one

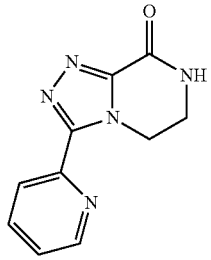 [SMILES: O=C1NCCn2c1nnc2-c1ccccn1]

Intermediate 2 was made in a manner analogous to Intermediate 1 substituting picolinohydrazide for pyrazine-2-carbohydrazide in Step B. MS (ESI): mass calcd. for $C_{10}H_9N_5O$, 215.1; m/z found, 216.1 [M+H]⁺. ¹H NMR (500 MHz, DMSO-d₆) δ 8.73 (d, J=4.5 Hz, 1H), 8.58 (s, 1H), 8.26 (d, J=7.9 Hz, 1H), 8.06-8.00 (m, 1H), 7.56 (dd, J=6.9, 5.1 Hz, 1H), 4.82-4.68 (m, 2H), 3.64 (s, 2H).

Intermediate 3. (±)-6-methyl-3-(pyrazin-2-yl)-6,7-dihydro-[1,2,4]triazolo[4,3-a]pyrazin-8(5H)-one

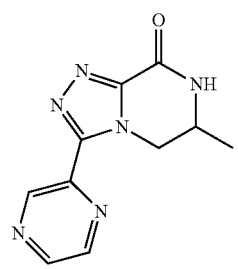 [SMILES: CC1Cn2c(nnc2-c2cnccn2)C(=O)N1]

Intermediate 3 was made in a manner analogous to Intermediate 1 substituting (±)-tert-butyl 2-methyl-5-oxopiperazine-1-carboxylate for tert-butyl 3-oxopiperazine-1-carboxylate in Step A. MS (ESI): mass calcd. for $C_{10}H_{10}N_6O$, 230.1; m/z found, 231.1 [M+H]⁺.

Intermediate 4. (6S)-1-(2-chloro-3-(trifluoromethyl)benzyl)-6-methylpiperazine-2,3-dione

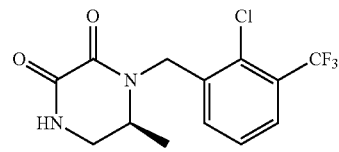 [SMILES: C[C@H]1CNC(=O)C(=O)N1Cc1cccc(C(F)(F)F)c1Cl]

Step A. (S)-tert-butyl (2-aminopropyl)carbamate

To a solution of (S)-1,2-diaminopropane dihydrochloride (16 g, 109 mmol) in MeOH (64 mL) and water (16 mL) was added di-tert-butyl dicarbonate (28.5 g, 131 mmol) in MeOH (16 mL). The resulting solution was cooled in an ice bath, and 4N NaOH (35 mL, 140 mL) was added dropwise over 2 h. The mixture was allowed to warm to rt and stirred for a total of 20 h. The reaction was filtered, and the filtrate concentrated to remove MeOH. 200 mL EtOAc, 200 mL water, and 16 mL 1M HCl were added sequentially. The layers were separated and the aqueous layer washed with EtOAc (200 mL). The combined organic extracts were washed with 0.04M HCl (208 mL). The organic phase was separated and discarded. The aqueous phases were combined, adjusted to pH=14 with 10N NaOH (20 mL), and extracted with DCM (400 mL×2). The combined organic extracts were dried (Na₂SO₄), filtered, and concentrated to afford the desired product as a clear oil (8.0 g, 42%). MS (ESI): mass calcd. for $C_8H_{18}N_2O_2$, 174.1; m/z found, 175.2 [M+H]⁺. ¹H NMR (500 MHz, CDCl₃) δ 5.01 (br s, 1H), 3.24-3.09 (m, 1H), 3.09-2.95 (m, 1H), 2.92-2.84 (m, 1H), 1.45 (s, 9H), 1.35-1.19 (m, 2H), 1.07 (d, J=6.4 Hz, 3H).

Step B. (6S)-tert-butyl (2-((2-chloro-3-(trifluoromethyl)benzyl)amino)propyl) carbamate A solution of (S)-tert-butyl(2-aminopropyl)carbamate (4.0 g, 23 mmol) and 2-chloro-3-trifluoromethylbenzaldehyde (4.8 g, 23 mmol) in DCE (100 mL) was stirred at rt for 2 h. Sodium triacetoxyborohydride (7.3 g, 34 mmol) was added at once and stirring continued overnight. Saturated aqueous NaHCO₃ was added, and the resulting mixture was extracted with DCM (×2). The combined organic extracts were dried (Na₂SO₄), filtered, and concentrated to afford a clear oil. Purification by chromatography (SiO₂; hex-60% EtOAc/hex) provided the desired product as a clear oil (7.2 g, 85%). MS (ESI): mass calcd. for $C_{16}H_{22}ClF_3N_2O_2$, 366.1; m/z found, 367.2 [M+H]⁺. ¹H NMR (400 MHz, CDCl₃) δ 7.72-7.56 (m, 2H), 7.35 (t, J=7.7 Hz, 1H), 4.94 (s, 1H), 3.99 (d, J=14.1 Hz, 1H), 3.90 (d, J=14.1 Hz, 1H), 3.29-3.14 (m, 1H), 3.11-2.99 (m, 1H), 2.84 (dd, J=11.1, 6.2 Hz, 1H), 1.44 (s, 9H), 1.11 (d, J=6.4 Hz, 3H).

Step C. (6S)-methyl 2-((1-((tert-butoxycarbonyl)amino)propan-2-yl)(2-chloro-3-(trifluoromethyl)benzyl)amino)-2-oxoacetate To an ice cold solution of (6S)-tert-butyl (2-((2-chloro-3-(trifluoromethyl)benzyl)amino)propyl) carbamate (7.2 g, 20 mmol) and triethylamine (2.8 mL, 21 mmol) in DCM (121 mL) was added methyl chlorooxoacetate (1.9 mL, 21 mmol) dropwise. The resulting mixture was warmed to rt and stirred overnight. After diluting with brine, the layers were separated, and the aqueous layer washed with DCM. The combined organic extracts were dried ($Na_2SO_4$), filtered, and concentrated to afford the desired product as a white solid (8.5 g, 97%). $^1$H NMR (400 MHz, $CDCl_3$) δ 7.72-7.56 (m, 1H), 7.49-7.32 (m, 2H), 4.83 (d, J=17.1 Hz, 1H), 4.79-4.62 (m, 1H), 4.51 (d, J=17.1 Hz, 1H), 4.11-3.97 (m, 1H), 3.93 (s, 3H), 3.24-3.13 (m, 2H), 1.44 (s, 9H), 1.16-1.12 (m, 3H).

Step D. (6S)-methyl 2((1-aminopropan-2-yl)(2-chloro-3-(trifluoromethyl) benzyl) amino)-2-oxoacetate hydrochloride To a solution of 4M HCl in dioxane (75 mL) was added (6S)-methyl 2-((1-((tert-butoxycarbonyl)amino)propan-2-yl)(2-chloro-3-(trifluoromethyl)benzyl)amino)-2-oxoacetate (7.5 g, 16.7 mmol). After 30 minutes, the reaction mixture was concentrated and the product was used in the next step without further purification (6.5 g, 100%). MS (ESI): mass calcd. for $C_{14}H_{16}ClF_3N_2O_3$, 352.1; m/z found, 353.1 $[M+H]^+$.

Step E. (6S)-1-(2-chloro-3-(trifluoromethyl)benzyl)-6-methylpiperazine-2,3-dione To a solution of (6S)-methyl 2-((1-aminopropan-2-yl)(2-chloro-3-(trifluoromethyl) benzyl) amino)-2-oxoacetate hydrochloride (7.3 g, 18.9 mmol) in DCM (90 mL) was added triethylamine (7.9 mL, 57 mmol) at once. After 2 h, 1N HCl was added and the layers were separated. The aqueous layer was extracted with DCM (×2). The combined organic extracts were dried ($Na_2SO_4$), filtered, and concentrated to afford the desired product as a white solid (5.9 g, 98%). MS (ESI): mass calcd. for $C_{13}H_{11}ClF_3N_2O_2$, 320.1; m/z found, 321.1 $[M+H]^+$. $^1$H NMR (600 MHz, $CDCl_3$) δ 8.24 (d, J=3.6 Hz, 1H), 7.68 (dd, J=7.8, 1.1 Hz, 1H), 7.59 (d, J=7.7 Hz, 1H), 7.39 (t, J=7.8 Hz, 1H), 5.22 (d, J=15.7 Hz, 1H), 4.52 (d, J=15.7 Hz, 1H), 3.82-3.73 (m, 1H), 3.69-3.61 (m, 1H), 3.31 (ddd, J=13.2, 5.2, 2.3 Hz, 1H), 1.46-1.38 (m, 3H).

Intermediate 5. (±)-1-(2-chloro-3-(trifluoromethyl) benzyl)-6-cyclopropylpiperazine-2,3-dione

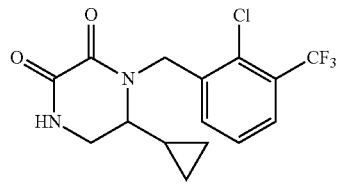 [SMILES: O=C1NCC(C2CC2)N(Cc2cccc(C(F)(F)F)c2Cl)C1=O]

Intermediate 5 was made in a manner analogous to Intermediate 4 substituting (±)1-cyclopropylethane-1,2-diamine for (S)-1,2-diaminopropane dihydrochloride in Step A. MS (ESI): mass calcd. for $C_{15}H_{14}ClF_3N_2O_2$, 346.1; m/z found, 347.1 $[M+H]^+$. $^1$H NMR (400 MHz, $CDCl_3$) δ 8.30 (s, 1H), 7.65 (d, J=7.7 Hz, 1H), 7.53 (d, J=7.7 Hz, 1H), 7.37 (t, J=7.9 Hz, 1H), 5.27 (d, J=16.0 Hz, 1H), 4.75 (d, J=16.0 Hz, 1H), 3.76 (dd, J=12.7, 4.7 Hz, 1H), 3.59-3.50 (m, 1H), 2.76-2.65 (m, 1H), 1.28-1.16 (m, 1H), 0.80-0.70 (m, 1H), 0.64-0.54 (m, 1H), 0.49-0.36 (m, 1H), 0.17-0.08 (m, 1H).

Intermediate 6. (6S)-1-(2-chloro-3-(trifluoromethyl) benzyl)-6-ethyl-3-thioxopiperazine-2-one

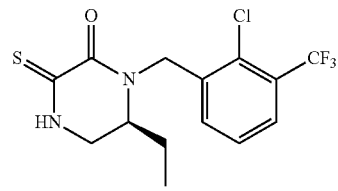 [SMILES: CC[C@H]1CNC(=S)C(=O)N1Cc1cccc(C(F)(F)F)c1Cl]

Step A. (S)-2-((tert-butoxycarbonyl)amino)butyl methanesulfonate

To an ice cold solution of (S)-tert-butyl (1-hydroxybutan-2-yl)carbamate (9.5 g, 50 mmol) and triethylamine (10.5 mL, 75 mmol) in ether (200 mL) was added methanesulfonyl chloride (4.0 mL, 50 mmol). After 1 h, water was added, and the resulting mixture was extracted with DCM, dried ($Na_2SO_4$), filtered, and concentrated to give an oil (13.4 g, 100%) which was used directly without further purification.

Step B. (S)-tert-butyl (1-azidobutan-2-yl)carbamate

To a solution of (S)-2-((tert-butoxycarbonyl)amino)butyl methanesulfonate (13.4 g, 50 mmol) in DMF (100 mL) was added sodium azide (6.5 g, 100 mmol). The reaction mixture was heated at 70° C. for 18 h. After cooling to rt, water was added, and the reaction mixture was extracted with EtOAc. The combined organic extracts were washed with brine, dried ($Na_2SO_4$), filtered, and concentrated. Purification by chromatography ($SiO_2$; 0-50% EtOAc/hexanes) provided the desired product as a white solid. $^1$H NMR (400 MHz, DMSO-$d_6$) δ 6.87 (d, J=8.6 Hz, 1H), 3.54-3.37 (m, 1H), 3.27-3.20 (m, 2H), 1.45-1.25 (m, 2H), 1.39 (s, 9H), 0.82 (t, J=7.4 Hz, 3H).

Step C. (S)-tert-butyl (1-aminobutan-2-yl)carbamate

A mixture of (S)-tert-butyl (1-azidobutan-2-yl)carbamate (7 g, 33 mmol) and 10% Pd/C (777 mg, 0.73 mmol) in EtOAc (150 mL) was stirred under hydrogen (60 psi) for 2 h. The reaction mixture was filtered through Celite and concentrated to give the desired product as a white semi-solid. $^1$H NMR (400 MHz, DMSO-$d_6$) δ 6.50 (d, J=8.7 Hz, 1H), 3.23-3.12 (m, 1H), 2.45 (d, J=6.0 Hz, 2H), 1.51-1.40 (m, 1H), 1.38 (s, 9H), 1.32-1.20 (m, 3H), 0.80 (t, J=7.4 Hz, 3H).

Step D. (S)-methyl 2-((2-((tert-butoxycarbonyl) amino)butyl)amino)-2-oxoacetate

To an ice cold solution of (S)-tert-butyl (1-aminobutan-2-yl)carbamate (1.0 g, 5.4 mmol) and triethylamine (0.78 mL, 5.6 mmol) in DCM (33 mL) was added methyl chlorooxoacetate (0.52 mL, 5.6 mmol) dropwise. Following the addition, the reaction was allowed to warm to rt and stirred overnight. Brine was added, the layers were separated, and the aqueous layer was washed with DCM. The combined organic extracts were dried ($Na_2SO_4$), filtered, and concentrated to provide a yellow oil (1.4 g, 96%), which was used without further purification. ¹H NMR (500 MHz, CDCl₃) δ 7.78 (s, 1H), 4.59 (d, J=7.6 Hz, 1H), 3.92-3.81 (m, 3H), 3.69 (s, 1H) 3.45 (dt, J=13.5, 4.2 Hz, 1H), 3.39-3.22 (m, 1H), 1.47-1.38 (m, 11H), 0.98 (t, J=7.5 Hz, 3H).

Step E. (S)-methyl 2-((2-aminobutyl)amino)-2-oxoacetate hydrochloride

To an ice cold solution of 4M HCl in dioxane (20 mL) was added (S)-methyl 2-((2-((tert-butoxycarbonyl)amino)butyl)amino)-2-oxoacetate (1.3 g, 4.6 mmol). After 30 minutes, the reaction mixture was concentrated to provide a yellow foam (968 mg, 100%), which was used without further purification. MS (ESI): mass calcd. for $C_7H_{14}N_2O_3$, 174.1; m/z found, 175.2 $[M+H]^+$.

Step F. (6S)-1-(2-chloro-3-(trifluoromethyl)benzyl)-6-ethylpiperazine-2,3-dione To an ice cold solution of (S)-methyl 2-((2-aminobutyl)amino)-2-oxoacetate hydrochloride (967 mg, 4.6 mmol) and 2-chloro-3-trifluoromethylbenzaldehyde (957 mg, 4.6 mmol) in DCM (26 mL) was added sodium triacetoxyborohydride (1.46 g, 6.9 mmol). The resulting mixture was allowed to warm to rt and stirred for 13 h. Triethylamine (1.9 mL) was added, and after 2 h the reaction was diluted with 1M HCl. The organic layer was washed with sat. aq. NaHCO₃ and brine, then dried (Na₂SO₄), and concentrated to afford a clear oil. Purification by chromatography (SiO₂; hexanes-10% IPA/EtOAc) provided the desired product as a white solid (580 mg, 38%). MS (ESI): mass calcd. for $C_{14}H_{14}ClF_3N_2O_2$, 334.1; m/z found, 335.1 $[M+H]^+$. ¹H NMR (500 MHz, CDCl₃) δ 8.10 (d, J=4.5 Hz, 1H), 7.68 (dd, J=7.8, 1.1 Hz, 1H), 7.62 (d, J=7.7 Hz, 1H), 7.39 (t, J=7.8 Hz, 1H), 5.28 (d, J=15.5 Hz, 1H), 4.48 (d, J=15.5 Hz, 1H), 3.70 (dd, J=13.4, 4.2 Hz, 1H), 3.44 (ddd, J=13.4, 5.5, 1.6 Hz, 1H), 3.37-3.28 (m, 1H), 1.25-1.17 (m, 2H), 0.99 (t, J=7.5 Hz, 3H).

Step G. (6S)-1-(2-chloro-3-(trifluoromethyl)benzyl)-6-ethyl-3-thioxopiperazin-2-one To a heterogeneous mixture of Lawesson's reagent (346 mg, 0.83 mmol) in THF (16 mL) was added (6S)-1-(2-chloro-3-(trifluoromethyl)benzyl)-6-ethylpiperazine-2,3-dione (555 mg, 1.7 mmol) at once. The mixture was heated at 55° C. for 20 minutes and then concentrated to remove the solvent. Purification by chromatography (SiO₂; hexanes-100% EtOAc) afforded the desired product as a yellow oil (528 mg, 91%). MS (ESI): mass calcd. for $C_{14}H_{14}ClF_3N_2OS$, 350.1; m/z found, 335.1 $[M+H]^+$. ¹H NMR (400 MHz, CDCl₃) δ 8.99 (s, 1H), 7.69 (dd, J=15.9, 7.8 Hz, 2H), 7.38 (t, J=7.8 Hz, 1H), 5.24 (d, J=15.3 Hz, 1H), 4.50 (d, J=15.3 Hz, 1H), 3.67 (dd, J=13.7, 3.9 Hz, 1H), 3.45 (dd, J=12.8, 5.4 Hz, 2H), 1.91-1.75 (m, 2H), 1.00 (t, J=7.5 Hz, 3H).

Intermediate 7. (±)-1-(1-bromozethyl)-2-chloro-3-(trifluoromethyl)benzene

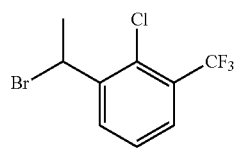

Step A. (±)-1-(2-chloro-3-(trifluoromethyl)phenyl)ethanol

To an ice cooled solution of 2-chloro-3-trifluoromethylbenzaldehyde (1 g, 4.8 mmol) in THF (16 mL) was added methylmagnesium bromide (3M in THF, 1.8 mL, 5.3 mmol). The reaction was allowed to warm to rt and stirred overnight. Saturated aqueous NH₄Cl was added, and the mixture was extracted with EtOAc (×3). The combined organic extracts were dried (Na₂SO₄), filtered, and concentrated to afford the desired product as a clear oil (1.1 g, 98%). ¹H NMR (500 MHz, CDCl₃) δ 7.86-7.82 (m, 1H), 7.62 (dd, J=7.8, 1.5 Hz, 1H), 7.40 (t, J=7.8 Hz, 1H), 5.40 (q, J=6.4 Hz, 1H), 2.14 (s, 1H), 1.50 (d, J=6.4 Hz, 3H).

Step B. (±)-1-(1-bromoethyl)-2-chloro-3-(trifluoromethyl)benzene

To an ice cooled solution of (±)-1-(2-chloro-3-(trifluoromethyl)phenyl)ethanol (1.1 g, 4.9 mmol) in DCM (16 mL) was added phosphorus tribromide (0.23 mL, 2.5 mmol) dropwise. The reaction was allowed to warm to rt and stirred for 3 h. Saturated aqueous NaHCO₃ was added, and the mixture was extracted with DCM (×3). The combined organic extracts were dried (Na₂SO₄), filtered, and concentrated to give the desired product as a yellow oil (1.4 g, 97%). ¹H NMR (400 MHz, CDCl₃) δ 7.93-7.81 (m, 1H), 7.69-7.64 (m, 1H), 7.42 (t, J=7.9 Hz, 1H), 5.73 (q, J=7.0 Hz, 1H), 2.05 (d, J=7.0 Hz, 3H).

Intermediate 8. pyrimidine-2-carbohydrazide

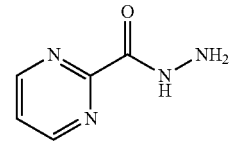

To a slurry of methyl pyrimidine-2-carboxylate (1.0 g, 7.2 mmol) in EtOH (5.6 mL) was added hydrazine monohydrate (0.72 mL, 14 mmol). The reaction mixture became homogeneous and after 5 min a precipitate formed. Stirring was continued for 1 h. The mixture was filtered, and the collected solid was washed with additional EtOH to provide the desired product as a beige solid (720 mg, 72%). MS (ESI): mass calcd. for $C_5H_6N_4O$, 138.1; m/z found, 139.1 $[M+H]^+$. ¹H NMR (500 MHz, DMSO-d₆) δ 10.06 (s, 1H), 8.92 (d, J=4.9 Hz, 2H), 7.64 (t, J=4.9 Hz, 1H), 4.64 (s, 2H).

Intermediate 9. pyrimidine-4-carbohydrazide

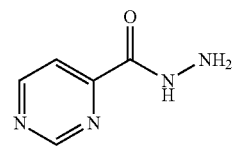

Intermediate 9 was made in a manner analogous to Intermediate 8 substituting ethyl pyrimidine-4-carboxylate for methyl pyrimidine-2-carboxylate to provide the desired compound as a white solid (713 mg, 79%). MS (ESI): mass calcd. for $C_5H_6N_4O$, 138.1; m/z found, 139.1 [M+H]$^+$. $^1$H NMR (400 MHz, DMSO-$d_6$) δ 10.31 (s, 1H), 9.27 (d, J=1.3 Hz, 1H), 9.03 (d, J=5.1 Hz, 1H), 7.97 (dd, J=5.1, 1.4 Hz, 1H), 4.72 (s, 2H).

Intermediate 10
5-bromopyrimidine-2-carbohydrazide

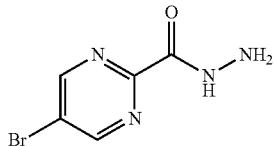

Step A. methyl 5-bromopyrimidine-2-carboxylate

To a solution of 5-bromopyrimidine-2-carbonitrile (3.0 g, 16 mmol) in MeOH (20 mL) was added concentrated HCl (19 mL). The reaction mixture was heated at 80° C. for 2 h. Upon cooling to rt, a precipitate formed. Filtration provided the desired product as a white solid (2.5 g, 71%). MS (ESI): mass calcd. for $C_6H_5BrN_2O_2$, 216.0; m/z found, 217.0 [M+H]$^+$. $^1$H NMR (500 MHz, DMSO-$d_6$) δ 9.20 (s, 2H), 3.92 (s, 3H).

Step B. 5-bromopyrimidine-2-carbohydrazide

To a slurry of methyl 5-bromopyrimidine-2-carboxylate (1.0 g, 4.6 mmol) in EtOH (3.6 mL) was added hydrazine monohydrate (0.46 mL, 9.2 mmol). The reaction mixture was stirred at rt for 1 h. The mixture was filtered, and the collected solid was washed with additional EtOH to provide the desired product as a beige solid (720 mg, 72%). MS (ESI): mass calcd. for $C_5H_5N_4O$, 216.0; m/z found, 217.0 [M+H]$^+$. $^1$H NMR (500 MHz, DMSO-$d_6$) δ 10.15 (s, 1H), 9.18-9.08 (s, 2H), 4.67 (s, 2H).

Intermediate 11. pyridazine-3-carbohydrazide

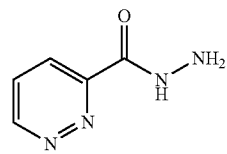

Intermediate 11 was made in a manner analogous to Intermediate 8 substituting methyl pyridazine-3-carboxylate for methyl pyrimidine-2-carboxylate to provide the desired compound as a white solid (328 mg, 66%). MS (ESI): mass calcd. for $C_5H_6N_4O$, 138.1; m/z found, 139.1 [M+H]$^+$. $^1$H NMR (400 MHz, DMSO-$d_6$) δ 10.45 (s, 1H), 9.39 (dd, J=5.0, 1.7 Hz, 1H), 8.17 (dd, J=8.4, 1.7 Hz, 1H), 7.91 (dd, J=8.4, 5.0 Hz, 1H), 4.71 (s, 2H).

Intermediate 12. pyridazine-3-carbohydrazide

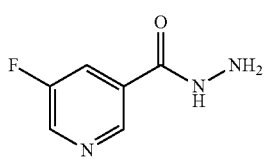 [SMILES: NNC(=O)c1cncc(F)c1]

Intermediate 12 was made in a manner analogous to Intermediate 8 substituting methyl 5-fluoronicotinate for methyl pyrimidine-2-carboxylate to provide the desired compound as a white solid (318 mg, 32%). MS (ESI): mass calcd. for $C_6H_6FN_3O$, 155.1; m/z found, 156.0 [M+H]$^+$. $^1$H NMR (400 MHz, DMSO-$d_6$) δ 10.07 (s, 1H), 8.86 (t, J=1.4 Hz, 1H), 8.74 (d, J=2.8 Hz, 1H), 8.05 (ddd, J=9.6, 2.7, 1.8 Hz, 1H), 4.63 (s, 2H).

Intermediate 13. 6-methylpicolinohydrazide

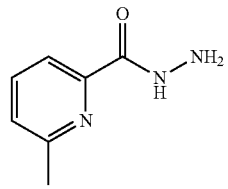

Intermediate 13 was made in a manner analogous to Intermediate 8 substituting methyl 6-methylpicolinate for methyl pyrimidine-2-carboxylate to provide the desired compound as a white solid (493 mg, 99%). $^1$H NMR (500 MHz, DMSO-$d_6$) δ 9.67 (s, 1H), 7.85 (t, J=7.7 Hz, 1H), 7.82-7.72 (m, 1H), 7.42 (dd, J=7.7, 0.6 Hz, 1H), 4.59 (s, 2H), 2.56-2.51 (m, 3H).

Intermediate 14. 2-methylnicotinohydrazide

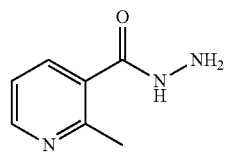

To a solution of ethyl 2-methylnicotinate (500 mg, 3.0 mmol) in EtOH (2.3 mL) was added hydrazine monohydrate (0.3 mL, 6.1 mmol). The reaction mixture was heated at reflux for 3 days and then concentrated to afford the desired product as a beige solid (450 mg, 98%). MS (ESI): mass calcd. for $C_7H_9N_3O$, 151.1; m/z found, 152.1 [M+H]$^+$. $^1$H NMR (500 MHz, DMSO-$d_6$) δ 9.57 (br s, 1H), 8.49 (dd, J=4.9, 1.8 Hz, 1H), 7.66 (dd, J=7.7, 1.7 Hz, 1H), 7.26 (ddd, J=7.7, 4.9, 0.5 Hz, 1H), 4.85-4.05 (bs, 2H), 2.50 (d, J=4.1 Hz, 3H).

Intermediate 15.
4-(trifluoromethyl)pyrimidine-2-carbohydrazide

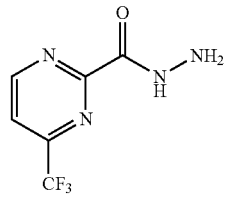 [SMILES: NNC(=O)c1cccc(C(F)(F)F)n1]

Step A. methyl 4-(trifluoromethyl)pyrimidine-2-carboxylate 4-(trifluoromethyl)pyrimidine-2-carboxylic acid (500 mg, 2.6 mmol) was dissolved in a mixture of 1 mL of THF and 300 μL of MeOH and cooled to 0° C. Trimethylsilyldiazomethane (2M in ether, 2.6 mL, 5.2 mmol) was added dropwise. The solution was stirred for 2 hours at 0° C., then 1 hour at rt. A few drops of AcOH were added, followed by water. The aqueous solution was extracted three times with EtOAc. The combined organic layers were dried (Na$_2$SO$_4$), filtered, and concentrated to give an oil which was used without further purification. MS (ESI): mass calcd. for C$_7$H$_5$F$_3$N$_2$O$_2$, 206.0; m/z found, 207.0 [M+H]$^+$. $^1$H NMR (400 MHz, CDCl$_3$) δ 9.24 (d, J=5.0 Hz, 1H), 7.87 (d, J=5.0 Hz, 1H), 4.10 (s, 3H).

Step B. 4-(trifluoromethyl)pyrimidine-2-carbohydrazide

To a solution of methyl 4-(trifluoromethyl)pyrimidine-2-carboxylate (500 mg, 2.4 mmol) in EtOH (12 mL) was added hydrazine monohydrate (0.24 mL, 4.9 mmol). After 1 h, the reaction was concentrated to afford the desired product as a white solid (426 mg, 85%). $^1$H NMR (400 MHz, CDCl$_3$) δ 9.22 (d, J=5.0 Hz, 1H), 9.05 (s, 1H), 7.83 (d, J=5.0 Hz, 1H), 4.25 (br s, 2H).

Intermediate 16. 6-(trifluoromethyl)picolinohydrazide

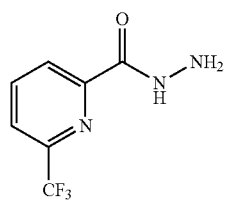

Intermediate 16 was made in a manner analogous to Intermediate 15 substituting 6-(trifluoromethyl)picolinic acid for 4-(trifluoromethyl)pyrimidine-2-carboxylic acid in Step A and heated at 70° C. for 1 h in Step B to provide the desired compound as a white solid (455 mg, 96%). $^1$H NMR (500 MHz, DMSO-d$_6$) δ 9.67 (s, 1H), 7.85 (t, J=7.7 Hz, 1H), 7.82-7.72 (m, 1H), 7.42 (dd, J=7.7, 0.6 Hz, 1H), 4.59 (s, 2H).

Intermediate 17. 5-chloropicolinohydrazide

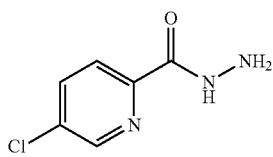 [SMILES: NNC(=O)c1ccc(Cl)cn1]

Intermediate 17 was made in a manner analogous to Intermediate 14 substituting ethyl 5-chloropicolinate for ethyl 2-methylnicotinate to afford the desired product as a beige solid (445 mg, 96%). MS (ESI): mass calcd. for C$_6$H$_6$ClN$_3$O, 171.0; m/z found, 172.0 [M+H]$^+$.

Intermediate 18. 5-methylnicotinohydrazide

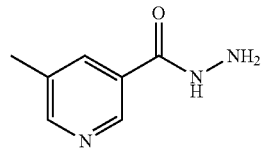

Intermediate 18 was made in a manner analogous to Intermediate 14 substituting methyl 5-methylnicotinate for ethyl 2-methylnicotinate to afford the desired product as a beige solid (497 mg, 99%). MS (ESI): mass calcd. for C$_7$H$_9$N$_3$O, 151.1; m/z found, 152.1 [M+H]$^+$. $^1$H NMR (400 MHz, DMSO-d$_6$) δ 9.91 (s, 1H), 8.77 (d, J=2.1 Hz, 1H), 8.53 (dd, J=2.1, 0.8 Hz, 1H), 8.00-7.97 (m, 1H), 4.46 (s, 2H), 2.34 (s, 3H).

Intermediate 19. 2-chloro-3-(trifluoromethyl)benzohydrazide

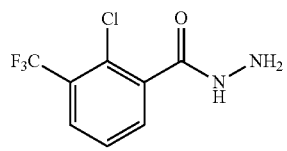 [SMILES: NNC(=O)c1cccc(C(F)(F)F)c1Cl]

To a solution of 2-chloro-3-(trifluoromethyl)benzoic acid (1.0 g, 4.5 mmol) in THF (7 mL) was added carbonyl diimidazole (939 mg, 5.8 mmol). After 40 minutes, additional carbonyl diimidazole (200 mg, 1.2 mmol) was added and stirring was continued for 30 minutes. This solution was added dropwise to a separate flask containing hydrazine monohydrate (0.44 mL, 8.9 mmol) in THF (8 mL). After 1 h, 1M HCl was added, and the reaction mixture was extracted with 20% IPA/CHCl$_3$ (×3). The combined organic extracts were washed with brine, dried (Na$_2$SO$_4$), filtered, and concentrated to afford the desired product as a white solid (1.0 g, 94%). MS (ESI): mass calcd. for C$_8$H$_6$ClF$_3$N$_2$O, 238.0; m/z found, 239.0 [M+H]$^+$. $^1$H NMR (500 MHz, MeOD) δ 7.87 (dd, J=7.9, 1.3 Hz, 1H), 7.72-7.63 (m, 1H), 7.56 (t, J=7.8 Hz, 1H), 7.05 (s, 1H).

Example 1. 7-[2-Chloro-3-(trifluoromethyl)benzyl]-3-(4-fluorophenyl)-6,7-dihydro[1,2,4]triazolo[4,3-a]pyrazin-8(5H)-one

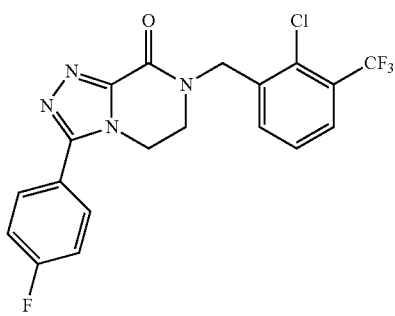 [SMILES: O=C1c2nnc(-c3ccc(F)cc3)n2CCN1Cc1cccc(C(F)(F)F)c1Cl]

Step A. tert-Butyl 3-bromo-8-oxo-5,6-dihydro-[1,2,4]triazolo[4,3-a]pyrazine-7(8H)-carboxylate To a vigorously stirred solution of tert-butyl 3-bromo-5,6-dihydro-[1,2,4]triazolo[4,3-a]pyrazine-7(8H)-carboxylate (1.0 g, 3.3 mmol) in 1:1 CHCl$_3$:MeCN (25 mL) was added ruthenium (IV) oxide hydrate (65 mg, 0.43 mmol) and sodium metaperiodate (3.3 g, 15.5 mmol) in water (31 mL). After 1 h, additional ruthenium (IV) oxide hydrate (50 mg) was added. After another hour, a final portion of ruthenium (IV) oxide hydrate (30 mg) was added. Stirring was maintained for 30 minutes and then water was added. The entire mixture was extracted with CHCl$_3$. The combined organic extracts were dried (Na$_2$SO$_4$), filtered, and concentrated to afford a green oil. Purification by chromatography (SiO$_2$; hexanes-100% EtOAc) provided the desired product as a white solid (663 mg, 63%). MS (ESI): mass calcd. for C$_{10}$H$_{13}$BrN$_4$O$_3$, 316.0; m/z found, 317.0 [M+H]$^+$. $^1$H NMR (400 MHz, CDCl$_3$) δ 4.41-4.28 (m, 2H), 4.26-4.22 (m, 2H), 1.58 (s, 9H).

Step B. 3-bromo-6,7-dihydro-[1,2,4]triazolo[4,3-a]pyrazin-8(5H)-one

To a solution of tert-butyl 3-bromo-8-oxo-5,6-dihydro-[1,2,4]triazolo[4,3-a]pyrazine-7(8H)-carboxylate (663 mg, 2.1 mmol) in DCM (21 mL) was added TFA (4.2 mL, 55 mmol). After 30 minutes, the reaction was concentrated and the residue was diluted with EtOAc, sonicated, and filtered to provide the desired product as a white solid (393 mg, 87%). MS (ESI): mass calcd. for C$_5$H$_5$BrN$_4$O, 216.0; m/z found, 217.0 [M+H]$^+$.

Step C. 3-bromo-7-(2-chloro-3-(trifluoromethyl)benzyl)-6,7-dihydro-[1,2,4]triazolo[4,3-a]pyrazin-8(5H)-one To a slurry of 3-bromo-6,7-dihydro-[1,2,4]triazolo[4,3-a]pyrazin-8(5H)-one (294 mg, 1.4 mmol) and cesium carbonate (1.32 g, 4.1 mmol) in DMF (10 mL) was added 1-(bromomethyl)-2-chloro-3-(trifluoromethyl)benzene (446 mg, 1.6 mmol). After 5 h, the reaction mixture was poured into ice cold brine (200 mL). The resulting precipitate was filtered and washed successively with water and ether to provide the product as a white solid (456 mg, 82%). MS (ESI): mass calcd. for C$_{13}$H$_9$BrClF$_3$N$_4$O, 408.0; m/z found, 409.0 [M+H]$^+$. $^1$H NMR (500 MHz, DMSO-d$_6$) δ 7.82 (d, J=7.6 Hz, 1H), 7.77 (d, J=7.6 Hz, 1H), 7.55 (t, J=7.8 Hz, 1H), 4.85 (s, 2H), 4.36-4.24 (m, 2H), 3.99-3.83 (m, 2H).

Step D. 7-[2-Chloro-3-(trifluoromethyl)benzyl]-3-(4-fluorophenyl)-6,7-dihydro[1,2,4]triazolo[4,3-a]pyrazin-8(5H)-one To a solution of 3-bromo-7-(2-chloro-3-(trifluoromethyl)benzyl)-6,7-dihydro-[1,2,4]triazolo[4,3-a]pyrazin-8(5H)-one (100 mg, 0.24 mmol) and 4-fluorophenylboronic acid (40 mg, 0.27 mmol) in dioxane (0.6 mL) was added 1M Na$_2$CO$_3$ (0.6 mL). The flask was purged with nitrogen for 10 minutes and Pd(PPh$_3$)$_4$ (14 mg, 0.012 mmol) was added at once. The flask was purged with nitrogen for an additional 5 minutes and then heated at 100° C. for 18 h. After cooling to rt, brine was added, and the mixture was extracted with EtOAc (×3). The combined organic extracts were dried (Na$_2$SO$_4$), filtered, and concentrated to give a brown solid. Purification by chromatography (SiO$_2$; hexanes-100% EtOAc) afforded the desired product as a white solid (47 mg, 45%). MS (ESI): mass calcd. for C$_{19}$H$_{13}$ClF$_4$N$_4$O, 424.1; m/z found, 425.1 [M+H]$^+$. $^1$H NMR (500 MHz, DMSO-d$_6$) δ 7.91-7.73 (m, 4H), 7.59-7.54 (m, 1H), 7.49-7.43 (m, 2H), 4.89 (s, 2H), 4.56-4.42 (m, 2H), 3.92-3.84 (m, 2H).

Example 2. 7-(2,3-Dichlorobenzyl)-3-pyrazin-2-yl-6,7-dihydro[1,2,4]triazolo[4,3-a]pyrazin-8(5H)-one

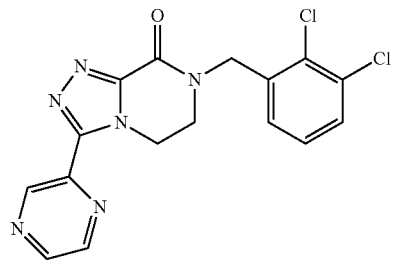 [SMILES: O=C1c2nnc(-c3cnccn3)n2CCN1Cc1cccc(Cl)c1Cl]

To a slurry of Intermediate 1 (60 mg, 0.18 mmol) and cesium carbonate (237 mg, 0.73 mmol) in DMF (1.4 mL) was added 1-(bromomethyl)-2,3-dichlorobenzene (65 mg, 0.27 mmol). After 5 h, the reaction was quenched with sat aq NH$_4$Cl, poured into brine, and extracted with 20% IPA/CHCl$_3$ (×3). The combined organic extracts were dried (Na$_2$SO$_4$), filtered, and concentrated to give a brown sludge. Trituration with MeOH provided the desired product as a beige powder (60 mg, 88%). MS (ESI): mass calcd. for C$_{16}$H$_{12}$Cl$_2$N$_6$O, 374.0; m/z found, 375.1 [M+H]$^+$. $^1$H NMR (500 MHz, DMSO-d$_6$) δ 9.41 (s, 1H), 8.77 (s, 2H), 7.57 (dd, J=7.9, 1.2 Hz, 1H), 7.49-7.38 (m, 1H), 7.33 (t, J=7.9 Hz, 1H), 4.86-4.75 (m, 4H), 3.90-3.81 (m, 2H).

Example 3. 7-[2-Chloro-3-(trifluoromethyl)benzyl]-3-pyrazin-2-yl-6,7-dihydro[1,2,4]triazolo[4,3-a]pyrazin-8(5H)-one

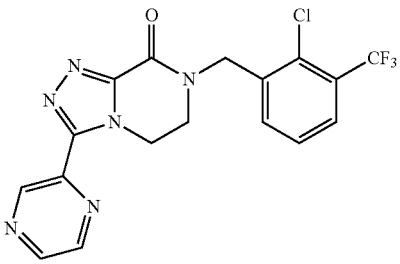 [SMILES: O=C1c2nnc(-c3cnccn3)n2CCN1Cc1cccc(C(F)(F)F)c1Cl]

Example 3 was made in a manner analogous to Example 2 substituting 1-(bromomethyl)-2-chloro-3-(trifluoromethyl)benzene for 1-(bromomethyl)-2,3-dichlorobenzene to provide the desired compound as a white solid (90 mg, 79%). MS (ESI): mass calcd. for C$_{17}$H$_{12}$ClF$_3$N$_5$O, 408.1; m/z found, 409.1 [M+H]$^+$. $^1$H NMR (500 MHz, DMSO-d$_6$) δ 9.46 (d, J=1.1 Hz, 1H), 8.83 (d, J=1.2 Hz, 2H), 7.90-7.75 (m, 2H), 7.57 (t, J=7.8 Hz, 1H), 4.89 (s, 2H), 4.88-4.84 (m, 2H), 4.01-3.88 (m, 2H).

Example 4. (±)7-{1-[2-Chloro-3-(trifluoromethyl)phenyl]ethyl}-3-pyrazin-2-yl-6,7-dihydro[1,2,4]triazolo[4,3-a]pyrazin-8(5H)-one

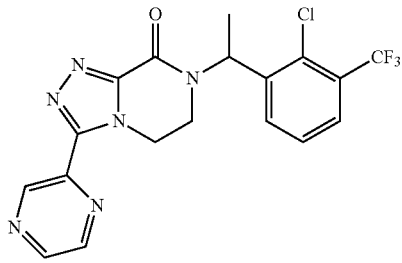 [SMILES: CC(c1cccc(C(F)(F)F)c1Cl)N1CCn2c(nnc2-c2cnccn2)C1=O]

Example 4 was made in a manner analogous to Example 2 substituting Intermediate 7 for 1-(bromomethyl)-2,3-dichlorobenzene to provide the desired compound as a white solid (52 mg, 53%). MS (ESI): mass calcd. for $C_{18}H_{14}ClF_3N_5O$, 422.1; m/z found, 423.1 [M+H]$^+$. $^1$H NMR (500 MHz, DMSO-d$_6$) δ 9.43 (d, J=1.4 Hz, 1H), 8.79 (dt, J=2.6, 2.1 Hz, 2H), 7.95 (d, J=7.8 Hz, 1H), 7.88 (dd, J=7.8, 1.0 Hz, 1H), 7.65 (t, J=7.9 Hz, 1H), 5.98 (q, J=7.0 Hz, 1H), 4.75 (ddd, J=13.6, 6.9, 4.4 Hz, 1H), 4.65-4.54 (m, 1H), 3.79 (ddd, J=12.6, 7.9, 4.4 Hz, 1H), 3.54-3.44 (m, 1H), 1.63 (d, J=7.1 Hz, 3H).

Example 5. 7-(2,6-Dichlorobenzyl)-3-pyrazin-2-yl-6,7-dihydro[1,2,4]triazolo[4,3-a]pyrazin-8(5H)-one

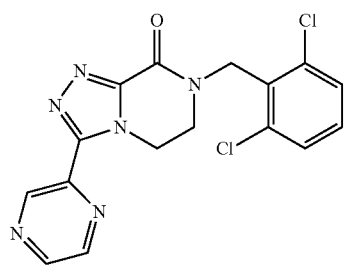 [SMILES: O=C1c2nnc(-c3cnccn3)n2CCN1Cc1c(Cl)cccc1Cl]

Example 5 was made in a manner analogous to Example 2 substituting 2-(bromomethyl)-1,3-dichlorobenzene for 1-(bromomethyl)-2,3-dichlorobenzene to provide the desired compound as a white solid (54 mg, 95%). MS (ESI): mass calcd. for $C_{16}H_{12}Cl_2N_6O$, 374.0; m/z found, 375.0 [M+H]$^+$. $^1$H NMR (500 MHz, DMSO-d$_6$) δ 9.42 (d, J=1.2 Hz, 1H), 8.78 (dd, J=8.0, 1.9 Hz, 2H), 7.55 (d, J=8.1 Hz, 2H), 7.50-7.36 (m, 1H), 5.00 (s, 2H), 4.73-4.56 (m, 2H), 3.72-3.56 (m, 2H).

Example 6. 7-(2,3-Difluorobenzyl)-3-pyrazin-2-yl-6,7-dihydro[1,2,4]triazolo[4,3-a]pyrazin-8(5H)-one

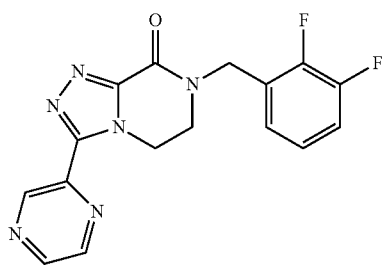 [SMILES: O=C1c2nnc(-c3cnccn3)n2CCN1Cc1cccc(F)c1F]

Example 6 was made in a manner analogous to Example 2 substituting 1-(bromomethyl)-2,3-difluorobenzene for 1-(bromomethyl)-2,3-dichlorobenzene to provide the desired compound as a white solid (43 mg, 83%). MS (ESI): mass calcd. for $C_{16}H_{12}F_2N_6O$, 342.1; m/z found, 343.1 [M+H]$^+$. $^1$H NMR (500 MHz, DMSO-d$_6$) δ 9.44 (d, J=0.7 Hz, 1H), 8.81 (s, 2H), 7.39 (dd, J=17.0, 8.3 Hz, 1H), 7.29 (t, J=7.0 Hz, 1H), 7.25-7.16 (m, 1H), 4.84 (s, 2H), 4.82-4.75 (m, 2H), 3.94-3.78 (m, 2H).

Example 7. 7-[4-Chloro-2-(methylsulfonyl)benzyl]-3-pyrazin-2-yl-6,7-dihydro[1,2,4]triazolo[4,3-a]pyrazin-8(5H)-one

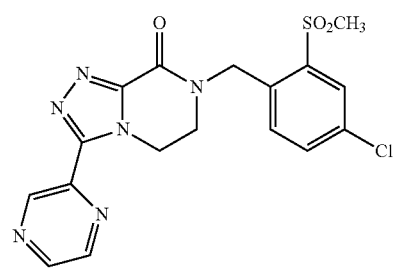 [SMILES: CS(=O)(=O)c1cc(Cl)ccc1CN1CCn2c(nnc2-c2cnccn2)C1=O]

Example 7 was made in a manner analogous to Example 2 substituting 1-(bromomethyl)-4-chloro-2-(methylsulfonyl)benzene for 1-(bromomethyl)-2,3-dichlorobenzene to provide the desired compound as a white solid (38 mg, 60%). MS (ESI): mass calcd. for $C_{17}H_{15}ClN_6O_3S$, 418.1; m/z found, 419.1 [M+H]$^+$. $^1$H NMR (500 MHz, DMSO-d$_6$) δ 9.47-9.42 (m, 1H), 8.82 (s, 2H), 7.95 (d, J=1.6 Hz, 1H), 7.77 (d, J=8.3 Hz, 1H), 7.67 (d, J=8.4 Hz, 1H), 5.14 (s, 2H), 4.94-4.80 (m, 2H), 4.03-3.85 (m, 2H), 2.50 (s, 3H).

Example 8. 7-(2,3-Dichlorobenzyl)-3-pyridin-2-yl-6,7-dihydro[1,2,4]triazolo[4,3-a]pyrazin-8(5H)-one

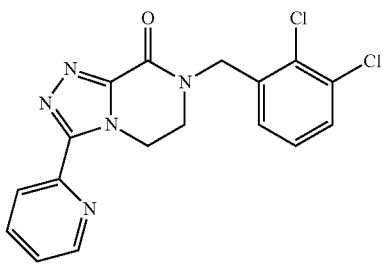 [SMILES: O=C1c2nnc(-c3ccccn3)n2CCN1Cc1cccc(Cl)c1Cl]

Example 8 was made in a manner analogous to Example 2 substituting Intermediate 2 for Intermediate 1 to provide the desired compound as a white solid (45 mg, 66%). MS (ESI): mass calcd. for $C_{17}H_{13}Cl_2N_5O$, 373.1; m/z found, 374.1 [M+H]$^+$. $^1$H NMR (600 MHz, DMSO-d$_6$) δ 8.74 (d, J=4.3 Hz, 1H), 8.29 (d, J=7.9 Hz, 1H), 8.05 (dt, J=7.8, 1.6 Hz, 1H), 7.66-7.52 (m, 2H), 7.47 (d, J=7.5 Hz, 1H), 7.37 (t, J=7.9 Hz, 1H), 4.96-4.88 (m, 2H), 4.84 (s, 2H), 3.93-3.82 (m, 2H).

Example 9. 7-[2-Chloro-3-(trifluoromethyl)benzyl]-3-pyridin-2-yl-6,7-dihydro[1,2,4]triazolo[4,3-a]pyrazin-8(5H)-one

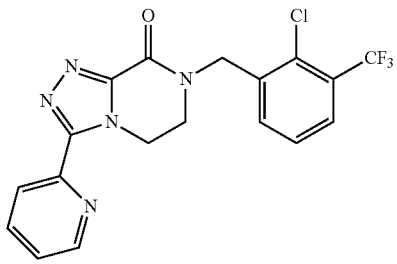

Example 9 was made in a manner analogous to Example 2 substituting Intermediate 2 for Intermediate 1 and 1-(bromomethyl)-2-chloro-3-(trifluoromethyl)benzene for 1-(bromomethyl)-2,3-dichlorobenzene to provide the desired compound as a white solid (66 mg, 89%). MS (ESI): mass calcd. for $C_{18}H_{13}ClF_3N_5O$, 407.1; m/z found, 408.1 [M+H]$^+$. $^1$H NMR (600 MHz, DMSO-$d_6$) δ 8.75 (ddd, J=4.8, 1.6, 0.9 Hz, 1H), 8.29 (dt, J=8.0, 0.9 Hz, 1H), 8.05 (dt, J=7.8, 1.7 Hz, 1H), 7.82 (dd, J=12.7, 7.8 Hz, 2H), 7.64-7.49 (m, 2H), 4.97-4.90 (m, 2H), 4.88 (s, 2H), 3.98-3.88 (m, 2H).

Example 10. 7-[2-Methyl-3-(trifluoromethyl)benzyl]-3-pyridin-2-yl-6,7-dihydro[1,2,4]triazolo[4,3-a]pyrazin-8(5H)-one

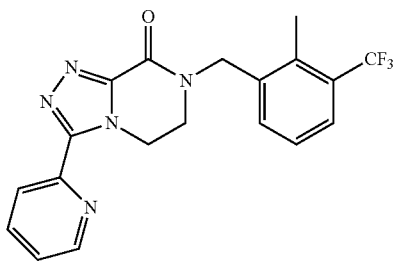 [SMILES: Cc1c(CN2CCn3c(nnc3-c3ccccn3)C2=O)cccc1C(F)(F)F]

Example 10 was made in a manner analogous to Example 2 substituting Intermediate 2 for Intermediate 1 and 1-(bromomethyl)-2-methyl-3-(trifluoromethyl)benzene for 1-(bromomethyl)-2,3-dichlorobenzene to provide the desired compound as a white solid (53 mg, 75%). MS (ESI): mass calcd. for $C_{19}H_{16}F_3N_5O$, 387.1; m/z found, 388.1 [M+H]$^+$. $^1$H NMR (500 MHz, DMSO-$d_6$) δ 8.78-8.66 (m, 1H), 8.29 (d, J=7.9 Hz, 1H), 8.05 (dt, J=7.8, 1.7 Hz, 1H), 7.63 (dd, J=16.8, 7.8 Hz, 2H), 7.57 (ddd, J=7.6, 4.9, 1.1 Hz, 1H), 7.40 (t, J=7.8 Hz, 1H), 4.87 (dd, J=15.9, 9.8 Hz, 4H), 3.85-3.74 (m, 2H), 2.41 (s, 3H).

Example 11. (±)-7-(2,3-Dichlorobenzyl)-6-methyl-3-pyrazin-2-yl-6,7-dihydro[1,2,4]triazolo[4,3-a]pyrazin-8(5H)-one

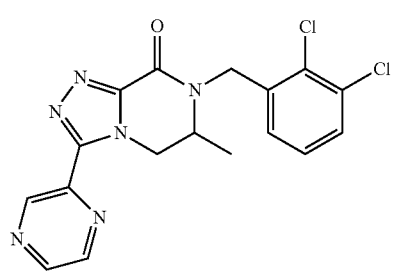 [SMILES: CC1Cn2c(nnc2-c2cnccn2)C(=O)N1Cc1cccc(Cl)c1Cl]

Example 11 was made in a manner analogous to Example 2 substituting Intermediate 3 for Intermediate 1 to provide the desired compound as a white solid (107 mg, 72%). MS (ESI): mass calcd. for $C_{17}H_{14}Cl_2N_6O$, 388.1; m/z found, 389.1 [M+H]$^+$. $^1$H NMR (600 MHz, DMSO-$d_6$) δ 9.48 (d, J=1.2 Hz, 1H), 8.89-8.69 (m, 2H), 7.68-7.56 (m, 1H), 7.51 (d, J=7.5 Hz, 1H), 7.37 (t, J=7.9 Hz, 1H), 5.17 (d, J=16.4 Hz, 1H), 4.97 (dd, J=13.8, 2.1 Hz, 1H), 4.77 (dd, J=13.8, 4.6 Hz, 1H), 4.51 (d, J=16.4 Hz, 1H), 4.17-4.06 (m, 1H), 1.22 (d, J=6.7 Hz, 3H).

Example 12. (6R)-7-(2,3-Dichlorobenzyl)-6-methyl-3-pyrazin-2-yl-6,7-dihydro[1,2,4]triazolo[4,3-a]pyrazin-8(5H)-one

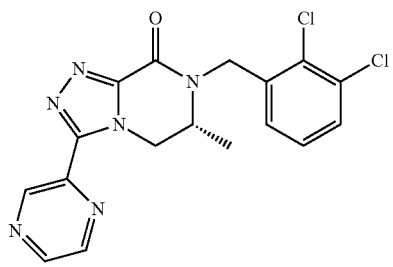 [SMILES: C[C@@H]1Cn2c(nnc2-c2cnccn2)C(=O)N1Cc1cccc(Cl)c1Cl]

Chiral SFC separation of (±)-7-(2,3-dichlorobenzyl)-6-methyl-3-pyrazin-2-yl-6,7-dihydro[1,2,4]triazolo[4,3-a]pyrazin-8(5H)-one on a CHIRALCEL OD-H column (5 μM, 250×20 mm) using 60% $CO_2$/40% MeOH provided 28 mg of the title compound as the first eluting enantiomer. [α]=+58° (c 3.0, CHCl$_3$). MS (ESI): mass calcd. for $C_{17}H_{14}Cl_2N_6O$, 388.1; m/z found, 389.1 [M+H]$^+$. $^1$H NMR (500 MHz, CDCl$_3$) δ 9.67 (d, J=1.5 Hz, 1H), 8.68 (d, J=2.5 Hz, 1H), 8.58 (dd, J=2.6, 1.5 Hz, 1H), 7.43 (ddd, J=18.7, 7.9, 1.5 Hz, 2H), 7.23 (t, J=7.8 Hz, 1H), 5.46 (d, J=15.4 Hz, 1H), 5.15 (dd, J=14.0, 2.1 Hz, 1H), 4.57-4.48 (m, 2H), 4.05-3.95 (m, 1H), 1.34 (d, J=6.7 Hz, 3H).

Example 13. (6S)-7-(2,3-Dichlorobenzyl)-6-methyl-3-pyrazin-2-yl-6,7-dihydro[1,2,4]triazolo[4,3-a]pyrazin-8(5H)-one

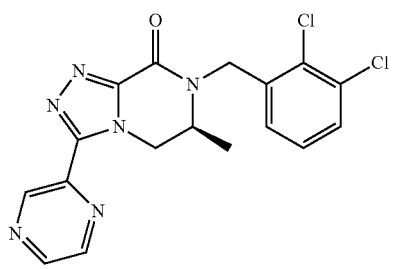 [SMILES: C[C@H]1Cn2c(nnc2-c2cnccn2)C(=O)N1Cc1cccc(Cl)c1Cl]

Chiral SFC separation of (±)-7-(2,3-dichlorobenzyl)-6-methyl-3-pyrazin-2-yl-6,7-dihydro[1,2,4]triazolo[4,3-a]pyrazin-8(5H)-one on a CHIRALCEL OD-H column (5 μM, 250×20 mm) using 60% $CO_2$/40% MeOH provided 30 mg of the title compound as the second eluting enantiomer. [α]=−55° (c 3.0, CHCl$_3$). MS (ESI): mass calcd. for $C_{17}H_{14}Cl_2N_6O$, 388.1; m/z found, 389.1 [M+H]$^+$. $^1$H NMR (500 MHz, CDCl$_3$) δ 9.67 (d, J=1.5 Hz, 1H), 8.68 (d, J=2.5 Hz, 1H), 8.58 (dd, J=2.6, 1.5 Hz, 1H), 7.43 (ddd, J=18.7, 7.9, 1.5 Hz, 2H), 7.23 (t, J=7.8 Hz, 1H), 5.46 (d, J=15.4 Hz, 1H), 5.15 (dd, J=14.0, 2.1 Hz, 1H), 4.57-4.48 (m, 2H), 4.05-3.95 (m, 1H), 1.34 (d, J=6.7 Hz, 3H).

Example 14. (±)-7-[2-Chloro-3-(trifluoromethyl) benzyl]-6-methyl-3-pyrazin-2-yl-6,7-dihydro[1,2,4] triazolo[4,3-a]pyrazin-8(5H)-one

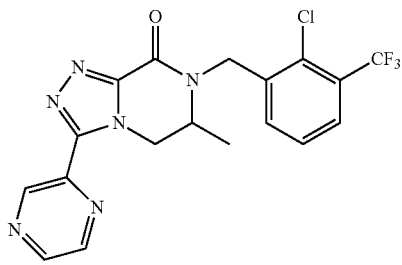 [SMILES: CC1Cn2c(nnc2-c2cnccn2)C(=O)N1Cc1cccc(C(F)(F)F)c1Cl]

Example 14 was made in a manner analogous to Example 2 substituting Intermediate 3 for Intermediate 1 and 1-(bromomethyl)-2-chloro-3-(trifluoromethyl)benzene for 1-(bromomethyl)-2,3-dichlorobenzene to provide the desired compound as a white solid (102 mg, 63%). MS (ESI): mass calcd. for $C_{18}H_{14}ClF_3N_5O$, 422.1; m/z found, 423.1 [M+H]$^+$. $^1$H NMR (500 MHz, DMSO-d$_6$) δ 9.48 (d, J=1.2 Hz, 1H), 8.84-8.82 (m, 2H), 7.85-7.82 (m, 2H), 7.56 (t, J=7.8 Hz, 1H), 5.20 (d, J=16.5 Hz, 1H), 4.98 (dd, J=13.8, 2.2 Hz, 1H), 4.80 (dd, J=13.8, 4.6 Hz, 1H), 4.56 (d, J=16.6 Hz, 1H), 4.23-4.10 (m, 1H), 1.23 (d, J=6.7 Hz, 3H).

Example 15. (6R)-7-[2-Chloro-3-(trifluoromethyl) benzyl]-6-methyl-3-pyrazin-2-yl-6,7-dihydro[1,2,4] triazolo[4,3-a]pyrazin-8(5H)-one

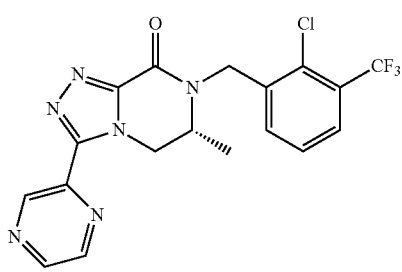 [SMILES: C[C@@H]1Cn2c(nnc2-c2cnccn2)C(=O)N1Cc1cccc(C(F)(F)F)c1Cl]

Chiral SFC separation of (±)-7-[2-Chloro-3-(trifluoromethyl)benzyl]-6-methyl-3-pyrazin-2-yl-6,7-dihydro[1,2,4] triazolo[4,3-a]pyrazin-8(5H)-one on a CHIRALCEL OD-H column (5 μM, 250×20 mm) using 70% CO$_2$/30% MeOH provided 39 mg of the title compound as the first eluting enantiomer. [α]=+40° (c 2.2, CHCl$_3$). MS (ESI): mass calcd. for $C_{18}H_{14}ClF_3N_5O$, 422.1; m/z found, 423.1 [M+H]$^+$. $^1$H NMR (500 MHz, CDCl$_3$) δ 9.66 (d, J=1.5 Hz, 1H), 8.68 (d, J=2.5 Hz, 1H), 8.59 (dd, J=2.5, 1.5 Hz, 1H), 7.76-7.72 (m, 1H), 7.69 (dd, J=7.9, 1.6 Hz, 1H), 7.41 (t, J=7.8 Hz, 1H), 5.44 (d, J=15.5 Hz, 1H), 5.17 (dd, J=13.9, 2.1 Hz, 1H), 4.62-4.54 (m, 2H), 4.08-4.02 (m, 1H), 1.36 (d, J=6.8 Hz, 3H).

Example 16. (6S)-7-[2-Chloro-3-(trifluoromethyl) benzyl]-6-methyl-3-pyrazin-2-yl-6,7-dihydro[1,2,4] triazolo[4,3-a]pyrazin-8(5H)-one

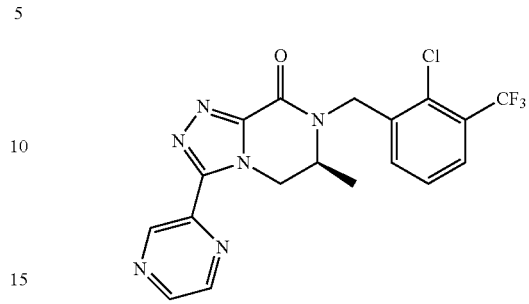

Chiral SFC separation of (±)-7-[2-Chloro-3-(trifluoromethyl)benzyl]-6-methyl-3-pyrazin-2-yl-6,7-dihydro[1,2,4] triazolo[4,3-a]pyrazin-8(5H)-one on a CHIRALCEL OD-H column (5 μM, 250×20 mm) using 70% CO$_2$/30% MeOH provided 40 mg of the title compound as the second eluting enantiomer. [α]=−44° (c 2.2, CHCl$_3$). MS (ESI): mass calcd. for $C_{18}H_{14}ClF_3N_5O$, 422.1; m/z found, 423.1 [M+H]$^+$. $^1$H NMR (500 MHz, CDCl$_3$) δ 9.66 (d, J=1.5 Hz, 1H), 8.68 (d, J=2.5 Hz, 1H), 8.59 (dd, J=2.5, 1.5 Hz, 1H), 7.76-7.72 (m, 1H), 7.69 (dd, J=7.9, 1.6 Hz, 1H), 7.41 (t, J=7.8 Hz, 1H), 5.44 (d, J=15.5 Hz, 1H), 5.17 (dd, J=13.9, 2.1 Hz, 1H), 4.62-4.54 (m, 2H), 4.08-4.02 (m, 1H), 1.36 (d, J=6.8 Hz, 3H).

Example 17. (6S)-7-[2-Chloro-3-(trifluoromethyl) benzyl]-3-(4-fluorophenyl)-6-methyl-6,7-dihydro[1, 2,4]triazolo[4,3-a]pyrazin-8(5H)-one

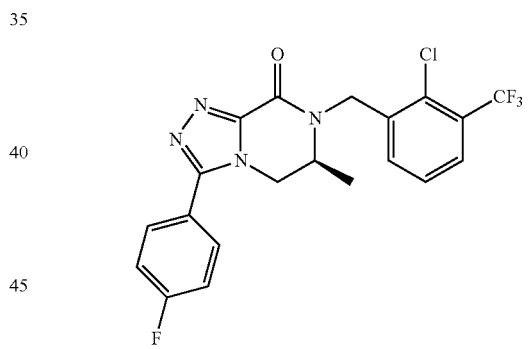

Step A. (6S)-1-(2-chloro-3-(trifluoromethyl)benzyl)-3-ethoxy-6-methyl-5,6-dihydropyrazin-2(1H)-one To an ice cooled solution of Intermediate 4 (1.0 g, 3.1 mmol) and sodium carbonate (6.6 g, 62 mmol) in DCM (45 mL) was added triethyloxonium tetrafluoroborate (1M in DCM, 15.6 mL, 15.6 mmol) dropwise. The ice bath was removed and the reaction was stirred at rt for 1.5 h. Water was added and the mixture was extracted with DCM (×3). The combined organic extracts were dried (Na$_2$SO$_4$), filtered, and concentrated to afford a yellow oil (1.1 g, 99%), which was used directly without further purification.

Step B. (6S)-7-[2-Chloro-3-(trifluoromethyl)benzyl]-3-(4-fluorophenyl)-6-methyl-6,7-dihydro[1,2,4] triazolo[4,3-a]pyrazin-8(5H)-one A solution of (6S)-1-(2-chloro-3-(trifluoromethyl)benzyl)-3-ethoxy-6-methyl-5,6-dihydropyrazin-2(1H)-one (216 mg, 0.62 mmol) and 4-fluorobenzohydrazide (105 mg, 0.68 mmol) in 1-butanol (6.2 mL) was heated at 130° C. for 16 h. After cooling to rt, the solvent was removed in vacuo. Purification by chromatography (SiO$_2$; 0-10% IPA/EtOAc) afforded the desired product as a white solid (158 mg, 58%). MS (ESI): mass calcd. for C$_{20}$H$_{15}$ClF$_4$N$_4$O, 438.1; m/z found, 439.1 [M+H]$^+$. $^1$H NMR (400 MHz, CDCl$_3$) δ 7.77-7.70 (m, 3H), 7.68-7.59 (m, 1H), 7.38 (t, J=7.8 Hz, 1H), 7.25-7.15 (m, 2H), 5.33 (d, J=15.7 Hz, 1H), 4.66 (dd, J=13.0, 4.5 Hz, 1H), 4.55 (d, J=15.7 Hz, 1H), 4.23 (dd, J=13.0, 2.0 Hz, 1H), 4.11 (dt, J=14.3, 4.8 Hz, 1H), 1.27-1.24 (m, 3H).

Example 18. (6S)-7-[2-Chloro-3-(trifluoromethyl)benzyl]-6-methyl-3-pyridin-2-yl-6,7-dihydro[1,2,4]triazolo[4,3-a]pyrazin-8(5H)-one

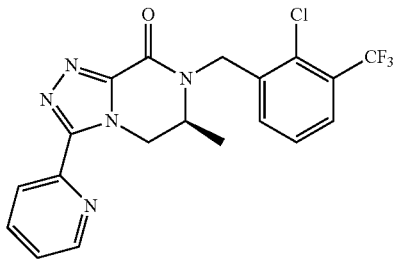 [SMILES: C[C@H]1Cn2c(nnc2-c2ccccn2)C(=O)N1Cc1cccc(C(F)(F)F)c1Cl]

Example 18 was made in a manner analogous to Example 17 substituting picolinohydrazide for 4-fluorobenzohydrazide in Step B to provide the desired compound as a white solid (133 mg, 51%). MS (ESI): mass calcd. for C$_{19}$H$_{15}$ClF$_3$N$_5$O, 421.1; m/z found, 422.1 [M+H]$^+$. $^1$H NMR (400 MHz, CDCl$_3$) δ 8.63 (ddd, J=4.8, 1.6, 0.9 Hz, 1H), 8.39 (dt, J=8.1, 1.0 Hz, 1H), 7.89-7.83 (m, 1H), 7.78-7.61 (m, 2H), 7.44-7.37 (m, 2H), 5.43 (d, J=15.7 Hz, 1H), 5.34 (dd, J=14.1, 2.1 Hz, 1H), 4.69-4.51 (m, 2H), 4.09-3.94 (m, 1H), 1.35 (d, J=6.8 Hz, 3H).

Example 19. (6S)-7-[2-Chloro-3-(trifluoromethyl)benzyl]-6-methyl-3-(5-methylpyrazin-2-yl)-6,7-dihydro[1,2,4]triazolo[4,3-a]pyrazin-8(5H)-one

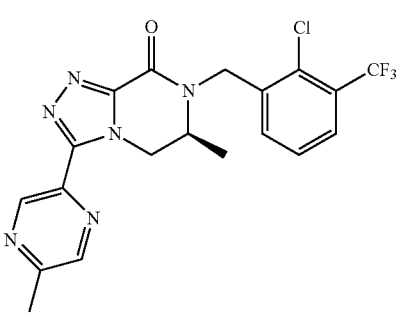 [SMILES: Cc1cnc(-c2nnc3n2C[C@H](C)N(Cc2cccc(C(F)(F)F)c2Cl)C3=O)cn1]

Example 19 was made in a manner analogous to Example 17 substituting 5-methylpyrazine-2-carbohydrazide for 4-fluorobenzohydrazide in Step B to provide the desired compound as a white solid (135 mg, 50%). MS (ESI): mass calcd. for C$_{19}$H$_{16}$ClF$_3$N$_5$O, 436.1; m/z found, 437.1 [M+H]$^+$. $^1$H NMR (500 MHz, CDCl$_3$) δ 9.47 (d, J=1.4 Hz, 1H), 8.47 (dd, J=1.4, 0.4 Hz, 1H), 7.76 (d, J=7.8 Hz, 1H), 7.68 (dd, J=7.8, 1.1 Hz, 1H), 7.42 (t, J=7.8 Hz, 1H), 5.42 (d, J=15.7 Hz, 1H), 5.16 (dd, J=14.0, 2.1 Hz, 1H), 4.68-4.51 (m, 2H), 4.09-3.99 (m, 1H), 2.66 (s, 3H), 1.35 (d, J=6.8 Hz, 3H).

Example 20. (6S)-7-[2-Chloro-3-(trifluoromethyl)benzyl]-6-methyl-3-(1,3-oxazol-2-yl)-6,7-dihydro[1,2,4]triazolo[4,3-a]pyrazin-8(5H)-one

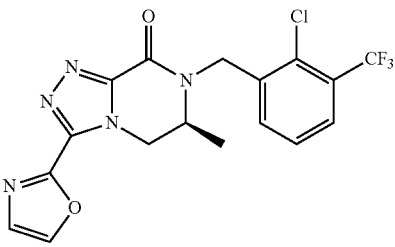 [SMILES: C[C@H]1Cn2c(nnc2-c2ncco2)C(=O)N1Cc1cccc(C(F)(F)F)c1Cl]

Example 20 was made in a manner analogous to Example 17 substituting oxazole-2-carbohydrazide for 4-fluorobenzohydrazide in Step B to provide the desired compound as a white solid (135 mg, 53%). MS (ESI): mass calcd. for C$_{17}$H$_{13}$ClF$_3$N$_5$O$_2$, 411.1; m/z found, 412.1 [M+H]$^+$. $^1$H NMR (500 MHz, CDCl$_3$) δ 7.90 (d, J=0.7 Hz, 1H), 7.74 (d, J=7.8 Hz, 1H), 7.72-7.61 (m, 1H), 7.42 (t, J=7.8 Hz, 1H), 7.36 (d, J=0.7 Hz, 1H), 5.39 (d, J=15.7 Hz, 1H), 5.05 (dd, J=13.9, 2.1 Hz, 1H), 4.66-4.52 (m, 2H), 4.22-4.13 (m, 1H), 1.37 (d, J=6.8 Hz, 3H).

Example 21. (6S)-7-[2-Chloro-3-(trifluoromethyl)benzyl]-6-methyl-3-(1,3-oxazol-4-yl)-6,7-dihydro[1,2,4]triazolo[4,3-a]pyrazin-8(5H)-one

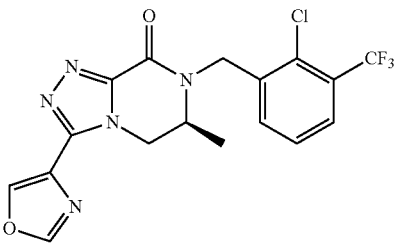 [SMILES: C[C@H]1Cn2c(nnc2-c2cocn2)C(=O)N1Cc1cccc(C(F)(F)F)c1Cl]

Example 21 was made in a manner analogous to Example 17 substituting oxazole-4-carbohydrazide for 4-fluorobenzohydrazide in Step B to provide the desired compound as a white solid (117 mg, 46%). MS (ESI): mass calcd. for C$_{17}$H$_{13}$ClF$_3$N$_5$O$_2$, 411.1; m/z found, 412.1 [M+H]$^+$. $^1$H NMR (500 MHz, CDCl$_3$) δ 8.51 (d, J=1.0 Hz, 1H), 8.06 (d, J=1.0 Hz, 1H), 7.72 (d, J=7.8 Hz, 1H), 7.70-7.63 (m, 1H), 7.40 (t, J=7.8 Hz, 1H), 5.40 (d, J=15.7 Hz, 1H), 5.01 (dd, J=13.7, 2.1 Hz, 1H), 4.64-4.50 (m, 2H), 4.07 (m, 1H), 1.36 (t, J=6.2 Hz, 3H).

Example 22. (6S)-7-[2-Chloro-3-(trifluoromethyl)benzyl]-6-methyl-3-(1,3-oxazol-5-yl)-6,7-dihydro[1,2,4]triazolo[4,3-a]pyrazin-8(5H)-one

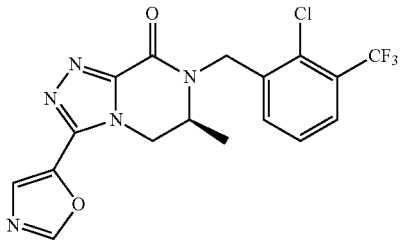 [SMILES: C[C@H]1Cn2c(nnc2-c2cnco2)C(=O)N1Cc1cccc(C(F)(F)F)c1Cl]

Example 22 was made in a manner analogous to Example 17 substituting oxazole-5-carbohydrazide for 4-fluorobenzohydrazide in Step B to provide the desired compound as a white solid (4.8 mg, 2%). MS (ESI): mass calcd. for $C_{17}H_{13}ClF_3N_5O_2$, 411.1; m/z found, 412.1 [M+H]$^+$. $^1$H NMR (400 MHz, CDCl$_3$) δ 8.07 (s, 1H), 7.90 (s, 1H), 7.72 (t, J=8.3 Hz, 2H), 7.41 (t, J=7.8 Hz, 1H), 5.45 (d, J=15.4 Hz, 1H), 4.57 (d, J=15.4 Hz, 1H), 4.49 (d, J=3.1 Hz, 2H), 4.13-4.03 (m, 1H), 1.37 (d, J=6.8 Hz, 3H).

Example 23. (6S)-7-[2-Chloro-3-(trifluoromethyl)benzyl]-6-methyl-3-(1-methyl-1H-pyrazol-3-yl)-6,7-dihydro[1,2,4]triazolo[4,3-a]pyrazin-8(5H)-one

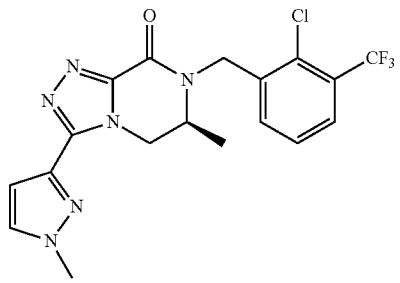 [SMILES: C[C@H]1Cn2c(nnc2-c2ccn(C)n2)C(=O)N1Cc1cccc(C(F)(F)F)c1Cl]

Example 23 was made in a manner analogous to Example 17 substituting 1-methyl-1H-pyrazole-3-carbohydrazide for 4-fluorobenzohydrazide in Step B to provide the desired compound as a white solid (61 mg, 23%). MS (ESI): mass calcd. for $C_{18}H_{16}ClF_3N_5O$, 424.1; m/z found, 425.1 [M+H]$^+$. $^1$H NMR (500 MHz, CDCl$_3$) δ 7.69 (dd, J=11.9, 7.8 Hz, 2H), 7.47 (d, J=2.3 Hz, 1H), 7.40 (t, J=7.8 Hz, 1H), 7.02 (d, J=2.3 Hz, 1H), 5.43 (d, J=15.7 Hz, 1H), 5.00 (dd, J=13.9, 2.0 Hz, 1H), 4.55 (d, J=15.7 Hz, 1H), 4.46 (dd, J=13.9, 4.6 Hz, 1H), 4.07-4.00 (m, 1H), 3.97 (s, 3H), 1.33 (d, J=6.7 Hz, 3H).

Example 24. (6S)-7-[2-Chloro-3-(trifluoromethyl)benzyl]-6-methyl-3-(1-methyl-1H-pyrazol-4-yl)-6,7-dihydro[1,2,4]triazolo[4,3-a]pyrazin-8(5H)-one

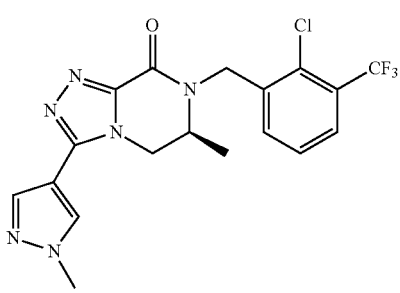 [SMILES: C[C@H]1Cn2c(nnc2-c2cnn(C)c2)C(=O)N1Cc1cccc(C(F)(F)F)c1Cl]

Example 24 was made in a manner analogous to Example 17 substituting 1-methyl-1H-pyrazole-4-carbohydrazide for 4-fluorobenzohydrazide in Step B to provide the desired compound as a white solid (116 mg, 44%). MS (ESI): mass calcd. for $C_{18}H_{16}ClF_3N_5O$, 424.1; m/z found, 425.1 [M+H]$^+$. $^1$H NMR (400 MHz, CDCl$_3$) δ 8.06 (s, 1H), 7.78 (s, 1H), 7.75-7.68 (m, 2H), 7.41 (t, J=7.8 Hz, 1H), 5.41 (d, J=15.5 Hz, 1H), 4.54 (d, J=15.5 Hz, 1H), 4.44 (dd, J=12.8, 4.6 Hz, 1H), 4.17 (dd, J=12.8, 1.9 Hz, 1H), 4.10-4.05 (m, 1H), 4.01 (s, 3H), 1.30 (d, J=6.8 Hz, 3H).

Example 25. (6S)-7-[2-Chloro-3-(trifluoromethyl)benzyl]-6-methyl-3-(1H-pyrazol-4-yl)-6,7-dihydro[1,2,4]triazolo[4,3-a]pyrazin-8(5H)-one

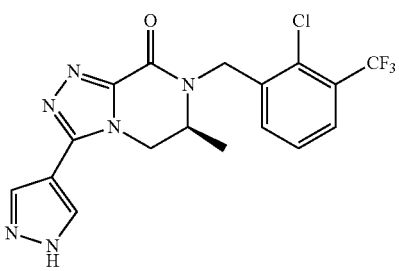 [SMILES: C[C@H]1Cn2c(nnc2-c2cn[nH]c2)C(=O)N1Cc1cccc(C(F)(F)F)c1Cl]

Example 25 was made in a manner analogous to Example 17 substituting 1H-pyrazole-4-carbohydrazide for 4-fluorobenzohydrazide in Step B to provide the desired compound as a white solid (104 mg, 41%). MS (ESI): mass calcd. for $C_{17}H_{14}ClF_3N_5O$, 410.1; m/z found, 411.1 [M+H]$^+$. $^1$H NMR (500 MHz, DMSO-d$_6$) δ 13.62 (br s, 1H), 8.27 (m, 2H), 7.84-7.78 (m, 2H), 7.55 (t, J=7.8 Hz, 1H), 5.19 (d, J=16.5 Hz, 1H), 4.65 (dd, J=13.2, 4.6 Hz, 1H), 4.53 (d, J=16.5 Hz, 1H), 4.36 (dd, J=13.2, 2.2 Hz, 1H), 4.22-4.06 (m, 1H), 1.21 (d, J=6.7 Hz, 3H).

Example 26. (6S)-7-[2-Chloro-3-(trifluoromethyl)benzyl]-6-methyl-3-(5-methyl-1H-pyrazol-3-yl)-6,7-dihydro[1,2,4]triazolo[4,3-a]pyrazin-8(5H)-one

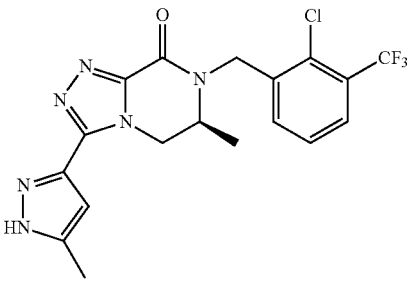 [SMILES: Cc1cc(-c2nnc3n2C[C@H](C)N(Cc2cccc(C(F)(F)F)c2Cl)C3=O)n[nH]1]

Example 26 was made in a manner analogous to Example 17 substituting 5-methyl-1H-pyrazole-3-carbohydrazide for 4-fluorobenzohydrazide in Step B to provide the desired compound as a white solid (87 mg, 33%). MS (ESI): mass calcd. for $C_{18}H_{16}ClF_3N_5O$, 424.1; m/z found, 425.1 [M+H]$^+$. $^1$H NMR (400 MHz, DMSO-d$_6$) δ 13.19 (s, 1H), 7.83 (d, J=7.9 Hz, 2H), 7.55 (t, J=7.8 Hz, 1H), 6.66 (s, 1H), 5.18 (d, J=16.6 Hz, 1H), 4.84 (d, J=13.6 Hz, 1H), 4.68 (dd, J=13.8, 4.5 Hz, 1H), 4.53 (d, J=16.6 Hz, 1H), 4.21-4.02 (m, 1H), 2.34 (s, 3H), 1.20 (d, J=6.6 Hz, 3H).

Example 27. (6S)-7-[2-Chloro-3-(trifluoromethyl)benzyl]-6-methyl-3-pyrimidin-2-yl-6,7-dihydro[1,2,4]triazolo[4,3-a]pyrazin-8(5H)-one

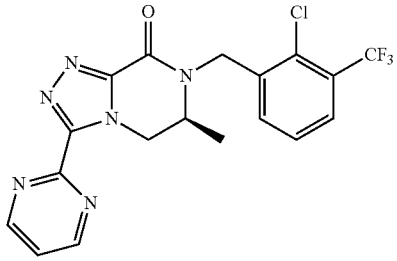 [SMILES: C[C@H]1Cn2c(nnc2-c2ncccn2)C(=O)N1Cc1cccc(C(F)(F)F)c1Cl]

Example 27 was made in a manner analogous to Example 17 substituting Intermediate 8 for 4-fluorobenzohydrazide in Step B to provide the desired compound as a white solid (85 mg, 32%). MS (ESI): mass calcd. for $C_{18}H_{14}ClF_3N_5O$, 422.1; m/z found, 423.1 [M+H]$^+$. $^1$H NMR (500 MHz, CDCl$_3$) δ 8.91 (d, J=4.9 Hz, 2H), 7.74 (d, J=7.6 Hz, 1H), 7.67 (d, J=7.6 Hz, 1H), 7.48-7.38 (m, 2H), 5.41 (d, J=15.7 Hz, 1H), 5.26 (dd, J=14.0, 2.0 Hz, 1H), 4.75-4.56 (m, 2H), 4.09 (ddd, J=6.6, 5.5, 3.2 Hz, 1H), 1.35 (d, J=6.7 Hz, 3H).

Example 28. (6S)-7-[2-Chloro-3-(trifluoromethyl)benzyl]-6-methyl-3-(1H-pyrazol-3-yl)-6,7-dihydro[1,2,4]triazolo[4,3-a]pyrazin-8(5H)-one

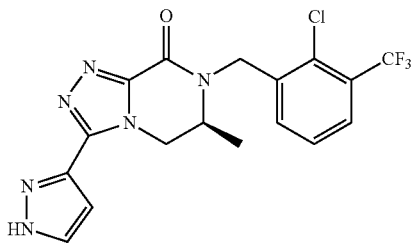 [SMILES: C[C@H]1Cn2c(nnc2-c2cc[nH]n2)C(=O)N1Cc1cccc(C(F)(F)F)c1Cl]

Example 28 was made in a manner analogous to Example 17 substituting 1H-pyrazole-3-carbohydrazide for 4-fluorobenzohydrazide in Step B to provide the desired compound as a white solid (68 mg, 27%). MS (ESI): mass calcd. for $C_{17}H_{14}ClF_3N_5O$, 410.1; m/z found, 411.1 [M+H]$^+$. $^1$H NMR (500 MHz, CDCl$_3$) δ 13.06 (s, 1H), 7.85 (d, J=2.4 Hz, 1H), 7.70-7.58 (m, 2H), 7.38 (t, J=7.8 Hz, 1H), 7.03 (d, J=2.3 Hz, 1H), 5.41 (d, J=15.8 Hz, 1H), 5.05 (dd, J=14.0, 1.5 Hz, 1H), 4.62-4.43 (m, 2H), 4.07-3.96 (m, 1H), 1.32 (d, J=6.7 Hz, 3H).

Example 29. (6S)-7-[2-Chloro-3-(trifluoromethyl)benzyl]-6-methyl-3-pyridin-3-yl-6,7-dihydro[1,2,4]triazolo[4,3-a]pyrazin-8(5H)-one

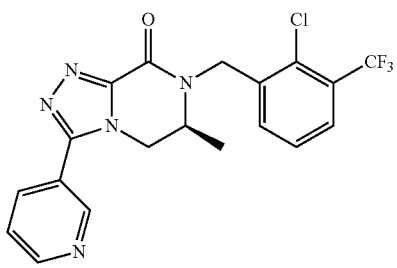 [SMILES: C[C@H]1Cn2c(nnc2-c2cccnc2)C(=O)N1Cc1cccc(C(F)(F)F)c1Cl]

Step A. (S)-1-(2-chloro-3-(trifluoromethyl)benzyl)-6-methyl-3-thioxopiperazin-2-one To a heterogeneous mixture of Lawesson's reagent (650 mg, 1.6 mmol) in THF (30 mL) was added Intermediate 4 (1.0 g, 3.1 mmol) in one portion. The mixture was heated at 55° C. for 20 minutes and then concentrated to remove solvent. Purification by chromatography (SiO$_2$; hexanes-100% EtOAc) afforded the desired product as a yellow solid (950 mg, 90%). MS (ESI): mass calcd. for $C_{13}H_{12}ClF_3N_2OS$, 336.0; m/z found, 337.1 [M+H]$^+$. $^1$H NMR (500 MHz, CDCl$_3$) δ 9.78 (d, J=4.2 Hz, 1H), 7.65 (d, J=7.9 Hz, 2H), 7.38 (t, J=7.8 Hz, 1H), 5.17 (d, J=15.6 Hz, 1H), 4.53 (d, J=15.6 Hz, 1H), 3.84-3.66 (m, 2H), 3.40 (dd, J=11.7, 5.6 Hz, 1H), 1.38 (d, J=6.7 Hz, 3H).

Step B. (6S)-7-[2-Chloro-3-(trifluoromethyl)benzyl]-6-methyl-3-pyridin-3-yl-6,7-dihydro[1,2,4]triazolo[4,3-a]pyrazin-8(5H)-one A solution of (S)-1-(2-chloro-3-(trifluoromethyl)benzyl)-6-methyl-3-thioxopiperazin-2-one (105 mg, 0.31 mmol) and nicotinohydrazide (47 mg, 0.34 mmol) in 1-butanol (3.1 mL) was heated at 130° C. for 16 h. After cooling to rt, the solvent was removed in vacuo. Purification by chromatography (SiO$_2$; 0-20% IPA/EtOAc) afforded the desired product as a white solid (102 mg, 78%). MS (ESI): mass calcd. for $C_{19}H_{15}ClF_3N_5O$, 421.1; m/z found, 422.1 [M+H]$^+$. $^1$H NMR (500 MHz, CDCl$_3$) δ 8.90 (d, J=1.8 Hz, 1H), 8.74 (dd, J=4.8, 1.4 Hz, 1H), 8.16-8.12 (m, 1H), 7.75 (d, J=7.7 Hz, 1H), 7.66 (d, J=7.6 Hz, 1H), 7.48 (dd, J=7.9, 4.9 Hz, 1H), 7.39 (t, J=7.8 Hz, 1H), 5.35 (d, J=15.6 Hz, 1H), 4.68 (dd, J=12.9, 4.5 Hz, 1H), 4.57 (d, J=15.6 Hz, 1H), 4.25 (dd, J=12.9, 1.8 Hz, 1H), 4.19-4.09 (m, 1H), 1.30 (d, J=6.7 Hz, 3H).

Example 30. (6S)-7-[2-Chloro-3-(trifluoromethyl)benzyl]-3-(5-fluoropyridin-2-yl)-6-methyl-6,7-dihydro[1,2,4]triazolo[4,3-a]pyrazin-8(5H)-one

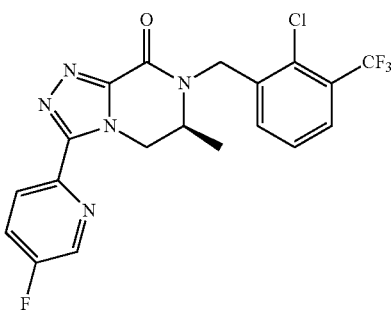 [SMILES: C[C@H]1Cn2c(nnc2-c2ccc(F)cn2)C(=O)N1Cc1cccc(C(F)(F)F)c1Cl]

Example 30 was made in a manner analogous to Example 29 substituting 5-fluoropicolinohydrazide for nicotinohydrazide in Step B to provide the desired compound as a white solid (109 mg, 49%). MS (ESI): mass calcd. for $C_{19}H_{14}ClF_4N_5O$, 439.1; m/z found, 440.1 [M+H]$^+$. $^1$H NMR (400 MHz, CDCl$_3$) δ 8.56-8.41 (m, 2H), 7.81-7.65 (m, 2H), 7.60 (ddd, J=8.8, 8.0, 2.9 Hz, 1H), 7.41 (t, J=7.8 Hz, 1H), 5.43 (d, J=15.6 Hz, 1H), 5.24 (dd, J=14.1, 2.1 Hz, 1H), 4.58 (dd, J=14.7, 4.8 Hz, 2H), 4.05 (ddd, J=6.7, 4.6, 2.1 Hz, 1H), 1.35 (d, J=6.8 Hz, 3H).

Example 31. (6S)-7-[2-Chloro-3-(trifluoromethyl)benzyl]-6-methyl-3-(1,3-thiazol-2-yl)-6,7-dihydro[1,2,4]triazolo[4,3-a]pyrazin-8(5H)-one

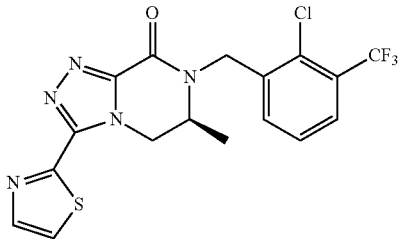

Example 31 was made in a manner analogous to Example 29 substituting thiazole-2-carbohydrazide for nicotinohydrazide in Step B to provide the desired compound as a white solid (187 mg, 87%). MS (ESI): mass calcd. for $C_{17}H_{13}ClF_3N_5OS$, 427.1; m/z found, 428.1 [M+H]$^+$. $^1$H NMR (500 MHz, CDCl$_3$) δ 7.96 (d, J=3.2 Hz, 1H), 7.79-7.65 (m, 2H), 7.57 (d, J=3.2 Hz, 1H), 7.41 (t, J=7.8 Hz, 1H), 5.41 (d, J=15.7 Hz, 1H), 5.18 (dd, J=13.9, 2.1 Hz, 1H), 4.59 (dd, J=14.7, 4.3 Hz, 2H), 4.13-4.07 (m, 1H), 1.37 (d, J=6.8 Hz, 3H).

Example 32. (6S)-7-[2-Chloro-3-(trifluoromethyl)benzyl]-6-methyl-3-(1,3-thiazol-4-yl)-6,7-dihydro[1,2,4]triazolo[4,3-a]pyrazin-8(5H)-one

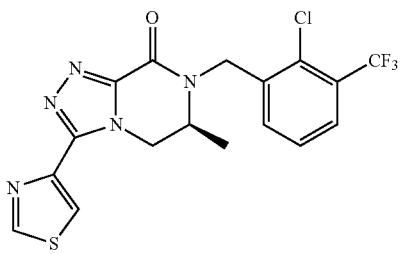 [SMILES: C[C@H]1Cn2c(nnc2-c2cscn2)C(=O)N1Cc1cccc(C(F)(F)F)c1Cl]

Example 32 was made in a manner analogous to Example 29 substituting thiazole-4-carbohydrazide for nicotinohydrazide in Step B to provide the desired compound as a white solid (191 mg, 89%). MS (ESI): mass calcd. for $C_{17}H_{13}ClF_3N_5OS$, 427.1; m/z found, 428.0 [M+H]$^+$. $^1$H NMR (500 MHz, CDCl$_3$) δ 8.94 (d, J=2.1 Hz, 1H), 8.36 (d, J=2.1 Hz, 1H), 7.73 (d, J=7.8 Hz, 1H), 7.70-7.64 (m, 1H), 7.40 (t, J=7.8 Hz, 1H), 5.42 (d, J=15.7 Hz, 1H), 5.15 (dd, J=13.8, 2.1 Hz, 1H), 4.65-4.52 (m, 2H), 4.08-3.99 (m, 1H), 1.35 (d, J=6.8 Hz, 3H).

Example 33. (6S)-7-[2-Chloro-3-(trifluoromethyl)benzyl]-6-methyl-3-pyrimidin-4-yl-6,7-dihydro[1,2,4]triazolo[4,3-a]pyrazin-8(5H)-one

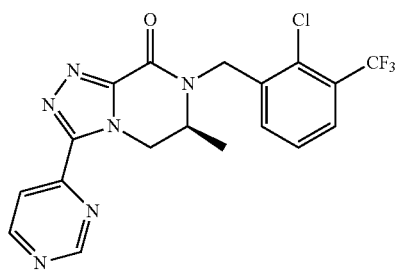 [SMILES: C[C@H]1Cn2c(nnc2-c2ccncn2)C(=O)N1Cc1cccc(C(F)(F)F)c1Cl]

Example 33 was made in a manner analogous to Example 29 substituting Intermediate 9 for nicotinohydrazide in Step B to provide the desired compound as a white solid (97 mg, 77%). MS (ESI): mass calcd. for $C_{18}H_{14}ClF_3N_5O$, 422.1; m/z found, 423.1 [M+H]$^+$. $^1$H NMR (400 MHz, CDCl$_3$) δ 9.27 (d, J=1.4 Hz, 1H), 8.93 (d, J=5.2 Hz, 1H), 8.36 (dd, J=5.2, 1.4 Hz, 1H), 7.74 (d, J=7.8 Hz, 1H), 7.70-7.64 (m, 1H), 7.41 (t, J=7.8 Hz, 1H), 5.51-5.31 (m, 2H), 4.77-4.54 (m, 2H), 4.09 (dd, J=4.6, 2.1 Hz, 1H), 1.37 (d, J=6.8 Hz, 3H).

Example 34. (6S)-7-[2-Chloro-3-(trifluoromethyl)benzyl]-3-(5-fluoropyrimidin-2-yl)-6-methyl-6,7-dihydro[1,2,4]triazolo[4,3-a]pyrazin-8(5H)-one

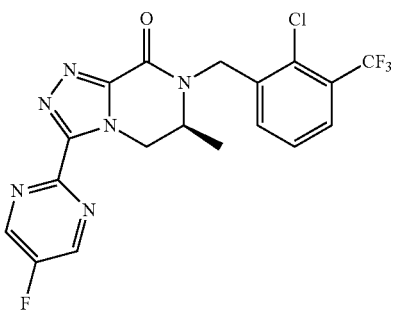

Example 34 was made in a manner analogous to Example 29 substituting 5-fluoropyrimidine-2-carbohydrazide for nicotinohydrazide in Step B to provide the desired compound as a white solid (94 mg, 72%). MS (ESI): mass calcd. for $C_{18}H_{13}ClF_4N_6O$, 440.1; m/z found, 441.1 [M+H]$^+$. $^1$H NMR (400 MHz, CDCl$_3$) δ 8.77 (s, 2H), 7.75 (d, J=7.6 Hz, 1H), 7.68 (d, J=7.8 Hz, 1H), 7.40 (t, J=7.8 Hz, 1H), 5.40 (d, J=15.7 Hz, 1H), 5.16 (dd, J=14.0, 2.1 Hz, 1H), 4.74-4.54 (m, 2H), 4.15-4.00 (m, 1H), 1.35 (d, J=6.8 Hz, 3H).

Example 35. (6S)-7-[2-Chloro-3-(trifluoromethyl)benzyl]-3-(4-methoxypyridin-2-yl)-6-methyl-6,7-dihydro[1,2,4]triazolo[4,3-a]pyrazin-8(5H)-one

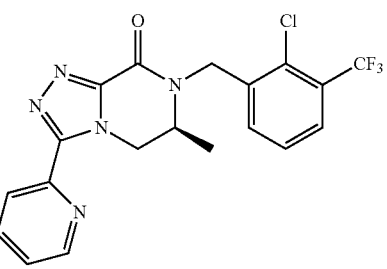

Example 35 was made in a manner analogous to Example 29 substituting 4-methoxypicolinohydrazide for nicotinohydrazide in Step B to provide the desired compound as a white solid (68 mg, 51%). MS (ESI): mass calcd. for $C_{20}H_{17}ClF_3N_5O_2$, 451.1; m/z found, 452.1 [M+H]$^+$. $^1$H NMR (400 MHz, CDCl$_3$) δ 8.39 (d, J=5.8 Hz, 1H), 7.99 (d, J=2.5 Hz, 1H), 7.70 (t, J=7.5 Hz, 2H), 7.40 (t, J=7.8 Hz, 1H), 6.90 (dd, J=5.8, 2.6 Hz, 1H), 5.46 (d, J=15.6 Hz, 1H), 5.35 (dd, J=14.1, 2.0 Hz, 1H), 4.64-4.41 (m, 2H), 4.05-3.97 (m, 1H), 3.95 (s, 3H), 1.34 (d, J=6.8 Hz, 3H).

Example 36. (6S)-7-[2-Chloro-3-(trifluoromethyl)benzyl]-6-methyl-3-(2-methyl-1,3-thiazol-4-yl)-6,7-dihydro[1,2,4]triazolo[4,3-a]pyrazin-8(5H)-one

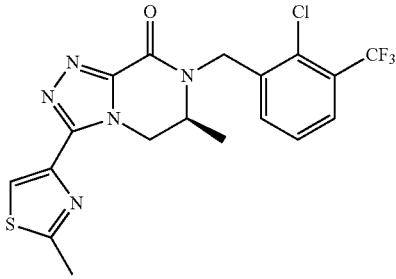 [SMILES: Cc1nc(-c2nnc3n2C[C@H](C)N(Cc2cccc(C(F)(F)F)c2Cl)C3=O)cs1]

Example 36 was made in a manner analogous to Example 29 substituting 2-methylthiazole-4-carbohydrazide for nicotinohydrazide in Step B to provide the desired compound as a white solid (103 mg, 79%). MS (ESI): mass calcd. for $C_{18}H_{15}ClF_3N_5OS$, 441.2; m/z found, 442.1 [M+H]$^+$. $^1$H NMR (500 MHz, CDCl$_3$) δ 8.13 (s, 1H), 7.75-7.63 (m, 2H), 7.40 (t, J=7.8 Hz, 1H), 5.42 (d, J=15.7 Hz, 1H), 5.15 (dd, J=13.9, 2.0 Hz, 1H), 4.64-4.45 (m, 2H), 4.04 (ddd, J=9.0, 4.4, 2.2 Hz, 1H), 2.76 (s, 3H), 1.35 (d, J=6.7 Hz, 3H).

Example 37. (6S)-7-[2-Chloro-3-(trifluoromethyl)benzyl]-6-methyl-3-(1,3-thiazol-5-yl)-6,7-dihydro[1,2,4]triazolo[4,3-a]pyrazin-8(5H)-one

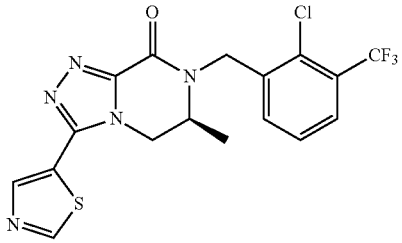

Example 37 was made in a manner analogous to Example 29 substituting thiazole-5-carbohydrazide for nicotinohydrazide in Step B to provide the desired compound as a white solid (90 mg, 71%). MS (ESI): mass calcd. for $C_{17}H_{13}ClF_3N_5OS$, 427.1; m/z found, 428.1 [M+H]$^+$. $^1$H NMR (500 MHz, CDCl$_3$) δ 9.00 (s, 1H), 8.24 (s, 1H), 7.77-7.69 (m, 2H), 7.42 (t, J=7.8 Hz, 1H), 5.43 (d, J=15.4 Hz, 1H), 4.57 (d, J=15.4 Hz, 1H), 4.51 (dd, J=12.8, 4.6 Hz, 1H), 4.27 (dd, J=12.8, 1.9 Hz, 1H), 4.19-4.07 (m, 1H), 1.35 (d, J=6.8 Hz, 3H).

Example 38. (6S)-7-[2-Chloro-3-(trifluoromethyl)benzyl]-6-methyl-3-[2-(trifluoromethyl)-1,3-thiazol-4-yl]-6,7-dihydro[1,2,4]triazolo[4,3-a]pyrazin-8(5H)-one

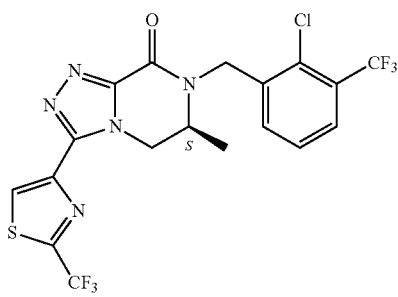

Example 38 was made in a manner analogous to Example 29 substituting 2-(trifluoromethyl)thiazole-4-carbohydrazide for nicotinohydrazide in Step B to provide the desired compound as a white solid (116 mg, 79%). MS (ESI): mass calcd. for $C_{18}H_{12}ClF_6N_5OS$, 495.0; m/z found, 496.0 [M+H]$^+$. $^1$H NMR (500 MHz, CDCl$_3$) δ 8.61 (s, 1H), 7.81-7.63 (m, 2H), 7.41 (t, J=7.8 Hz, 1H), 5.45 (d, J=15.6 Hz, 1H), 5.04 (dd, J=13.8, 1.9 Hz, 1H), 4.65-4.51 (m, 2H), 4.11-4.01 (m, 1H), 1.38 (d, J=6.8 Hz, 3H).

Example 39. (6S)-7-[2-Chloro-3-(trifluoromethyl)benzyl]-3-(2,4-dimethyl-1,3-thiazol-5-yl)-6-methyl-6,7-dihydro[1,2,4]triazolo[4,3-a]pyrazin-8(5H)-one

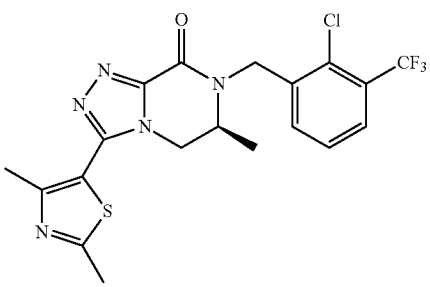 [SMILES: Cc1nc(C)c(-c2nnc3n2C[C@H](C)N(Cc2cccc(C(F)(F)F)c2Cl)C3=O)s1]

Example 39 was made in a manner analogous to Example 29 substituting 2,4-dimethylthiazole-5-carbohydrazide for nicotinohydrazide in Step B to provide the desired compound as a white solid (86 mg, 64%). MS (ESI): mass calcd. for $C_{19}H_{17}ClF_3N_5OS$, 455.1; m/z found, 456.1 [M+H]$^+$. $^1$H NMR (500 MHz, CDCl$_3$) δ 7.80-7.61 (m, 2H), 7.40 (t, J=7.8 Hz, 1H), 5.37 (d, J=15.5 Hz, 1H), 4.56 (d, J=15.5 Hz, 1H), 4.35 (dd, J=13.3, 4.8 Hz, 1H), 4.14-4.01 (m, 2H), 2.75 (s, 3H), 2.56 (s, 3H), 1.31 (d, J=6.7 Hz, 3H).

Example 40. (6S)-7-[2-Chloro-3-(trifluoromethyl)benzyl]-6-methyl-3-(4-methyl-1,3-thiazol-5-yl)-6,7-dihydro[1,2,4]triazolo[4,3-a]pyrazin-8(5H)-one

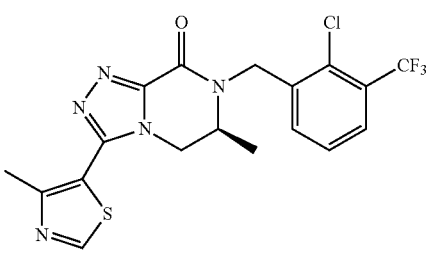 [SMILES: Cc1ncsc1-c1nnc2n1C[C@H](C)N(Cc1cccc(C(F)(F)F)c1Cl)C2=O]

Example 40 was made in a manner analogous to Example 29 substituting 4-methylthiazole-5-carbohydrazide for nicotinohydrazide in Step B to provide the desired compound as a white solid (106 mg, 81%). MS (ESI): mass calcd. for $C_{18}H_{15}ClF_3N_5OS$, 441.1; m/z found, 442.1 [M+H]$^+$. $^1$H NMR (500 MHz, CDCl$_3$) δ 8.94 (s, 1H), 7.73 (d, J=7.7 Hz, 1H), 7.70-7.64 (m, 1H), 7.40 (t, J=7.8 Hz, 1H), 5.35 (d, J=15.6 Hz, 1H), 4.57 (d, J=15.6 Hz, 1H), 4.49-4.36 (m, 1H), 4.17-4.08 (m, 2H), 2.64 (s, 3H), 1.33 (d, J=6.7 Hz, 3H).

Example 41. (6S)-7-[2-Chloro-3-(trifluoromethyl)benzyl]-3-isoxazol-3-yl-6-methyl-6,7-dihydro[1,2,4]triazolo[4,3-a]pyrazin-8(5H)-one

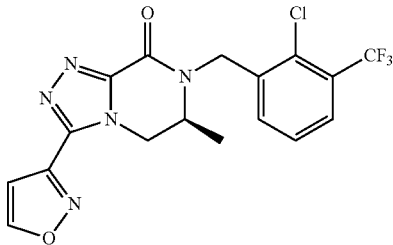 [SMILES: C[C@H]1Cn2c(nnc2-c2ccon2)C(=O)N1Cc1cccc(C(F)(F)F)c1Cl]

Example 41 was made in a manner analogous to Example 29 substituting isoxazole-3-carbohydrazide for nicotinohydrazide in Step B to provide the desired compound as a white solid (43 mg, 35%). MS (ESI): mass calcd. for $C_{17}H_{13}ClF_3N_5O_2$, 411.1; m/z found, 412.1 [M+H]$^+$. $^1$H NMR (500 MHz, CDCl$_3$) δ 8.59 (d, J=1.7 Hz, 1H), 7.73-7.68 (m, 2H), 7.41 (t, J=7.8 Hz, 1H), 7.18 (d, J=1.7 Hz, 1H), 5.43 (d, J=15.6 Hz, 1H), 4.92 (dd, J=13.8, 2.0 Hz, 1H), 4.66-4.47 (m, 2H), 4.10-4.02 (m, 1H), 1.36 (d, J=6.8 Hz, 3H).

Example 42. (6S)-3-(5-Bromopyrimidin-2-yl)-7-[2-chloro-3-(trifluoromethyl)benzyl]-6-methyl-6,7-dihydro[1,2,4]triazolo[4,3-a]pyrazin-8(5H)-one

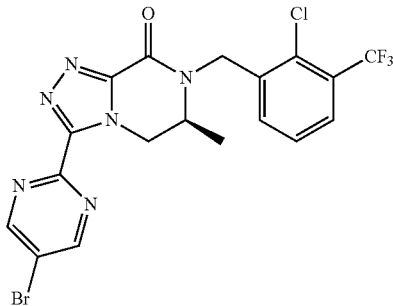

Example 42 was made in a manner analogous to Example 29 substituting Intermediate 10 for nicotinohydrazide in Step B to provide the desired compound as a white solid (193 mg, 65%). MS (ESI): mass calcd. for $C_{18}H_{13}BrClF_3N_5O$, 500.0; m/z found, 501.0 [M+H]$^+$. $^1$H NMR (500 MHz, CDCl$_3$) δ 8.96 (s, 2H), 7.76-7.68 (m, 2H), 7.42 (t, J=7.8 Hz, 1H), 5.42 (d, J=15.5 Hz, 1H), 5.16 (dd, J=14.0, 1.3 Hz, 1H), 4.59 (dd, J=14.5, 3.7 Hz, 2H), 4.13-4.02 (m, 1H), 1.35 (d, J=6.8 Hz, 3H).

Example 43. (6S)-3-(5-Tritiopyrimidin-2-yl)-7-[2-chloro-3-(trifluoromethyl)benzyl]-6-methyl-6,7-dihydro[1,2,4]triazolo[4,3-a]pyrazin-8(5H)-one

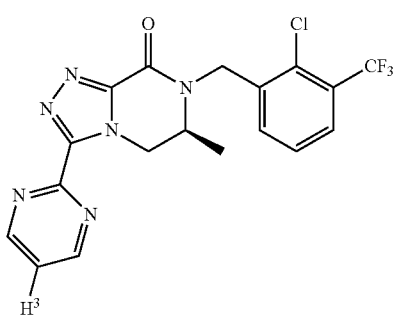

This reaction was performed on a RC Tritec Tritium Manifold system. (6S)-3-(5-bromopyrimidin-2-yl)-7-[2-chloro-3-(trifluoromethyl)benzyl]-6-methyl-6,7-dihydro[1,2,4]triazolo[4,3-a]pyrazin-8(5H)-one (1.9 mg, 3.8 μmol) was dissolved in EtOH (200 μL) together with diisopropylethylamine (2.1 μL, 11.5 μmol) and Lindlar Catalyst (4.4 mg) in a reaction vial with magnetic stirring bar. The mixture was cooled with liquid nitrogen and put under vacuum at 10$^{-3}$ mbar and thoroughly degassed. The mixture was cooled with liquid nitrogen and put under $^3$H$_2$-atmosphere (120 mbar). The mixture was allowed to warm to rt and stirred for 1 h (620 mbar final pressure). The reaction mixture was cooled with liquid nitrogen and the unreacted excess of tritium gas was absorbed on a waste trap. The volatile components of the reaction mixture were transferred by lyophilization to a waste vial. The solid residue was stirred with 200 μL of EtOH, cooled with liquid nitrogen, placed under vacuum and lyophilized to the waste vial. This was done 3 times to remove all volatile tritium. The mixture containing product was dissolved in EtOH (1 ml), filtered over an Acrodisk 13 GHP 0.45 μm syringe filter and the filter was thoroughly rinsed with EtOH. All fractions were combined and stored in 10 ml EtOH (at −20° C.), containing 4.0 GBq of the desired product.

Example 44. (6S)-7-[2-Chloro-3-(trifluoromethyl)benzyl]-6-methyl-3-pyridazin-3-yl-6,7-dihydro[1,2,4]triazolo[4,3-a]pyrazin-8(5H)-one

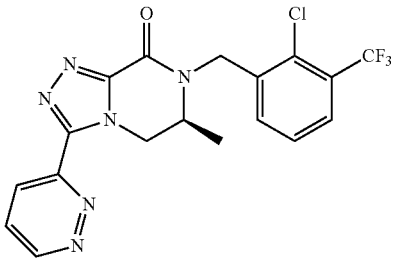 [SMILES: C[C@H]1Cn2c(nnc2-c2cccnn2)C(=O)N1Cc1cccc(C(F)(F)F)c1Cl]

Example 44 was made in a manner analogous to Example 29 substituting Intermediate 11 for nicotinohydrazide in Step B to provide the desired compound as a white solid (159 mg, 87%). MS (ESI): mass calcd. for $C_{18}H_{14}ClF_3N_5O$, 422.1; m/z found, 423.1 [M+H]$^+$. $^1$H NMR (500 MHz, CDCl$_3$) δ 9.27 (dd, J=5.0, 1.7 Hz, 1H), 8.60 (dd, J=8.6, 1.7 Hz, 1H), 7.80-7.70 (m, 3H), 7.41 (t, J=7.8 Hz, 1H), 5.52-5.32 (m, 2H), 4.74 (dd, J=14.1, 4.6 Hz, 1H), 4.61 (d, J=15.7 Hz, 1H), 4.17-4.07 (m, 1H), 1.39 (d, J=6.8 Hz, 3H).

Example 45. (6S)-7-[2-Chloro-3-(trifluoromethyl)benzyl]-3-(5-fluoropyridin-3-yl)-6-methyl-6,7-dihydro[1,2,4]triazolo[4,3-a]pyrazin-8(5H)-one

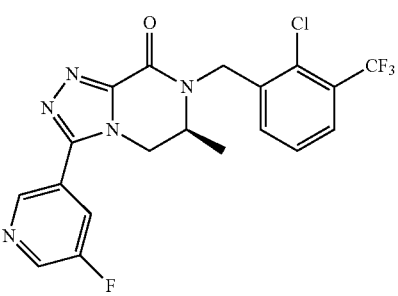 [SMILES: C[C@H]1Cn2c(nnc2-c2cncc(F)c2)C(=O)N1Cc1cccc(C(F)(F)F)c1Cl]

Example 45 was made in a manner analogous to Example 29 substituting Intermediate 12 for nicotinohydrazide in Step B to provide the desired compound as a white solid (85 mg, 65%). MS (ESI): mass calcd. for $C_{19}H_{14}ClF_4N_5O$, 439.1; m/z found, 439.9 [M+H]$^+$. $^1$H NMR (500 MHz, CDCl$_3$) δ 8.73 (d, J=1.3 Hz, 1H), 8.62 (d, J=2.7 Hz, 1H), 7.93 (ddd, J=8.6, 2.7, 1.8 Hz, 1H), 7.75 (d, J=7.7 Hz, 1H), 7.67 (dd, J=7.8, 1.1 Hz, 1H), 7.40 (t, J=7.8 Hz, 1H), 5.35 (d, J=15.6 Hz, 1H), 4.70 (dd, J=12.9, 4.5 Hz, 1H), 4.58 (d, J=15.6 Hz, 1H), 4.27 (dd, J=12.9, 2.0 Hz, 1H), 4.15 (ddd, J=7.9, 3.9, 1.6 Hz, 1H), 1.31 (d, J=6.8 Hz, 3H).

Example 46. (6S)-7-[2-Chloro-3-(trifluoromethyl)benzyl]-6-methyl-3-(6-methylpyridin-2-yl)-6,7-dihydro[1,2,4]triazolo[4,3-a]pyrazin-8(5H)-one

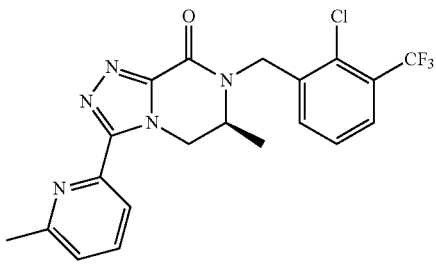

Example 46 was made in a manner analogous to Example 29 substituting Intermediate 13 for nicotinohydrazide in Step B to provide the desired compound as a white solid (98 mg, 76%). MS (ESI): mass calcd. for $C_{20}H_{17}ClF_3N_5O$, 435.1; m/z found, 436.0 [M+H]$^+$. $^1$H NMR (500 MHz, CDCl$_3$) δ 8.19 (d, J=7.8 Hz, 1H), 7.79-7.70 (m, 2H), 7.70-7.63 (m, 1H), 7.42 (t, J=7.8 Hz, 1H), 7.24 (d, J=7.6 Hz, 1H), 5.44 (d, J=15.7 Hz, 1H), 5.37 (dd, J=14.1, 1.9 Hz, 1H), 4.65-4.52 (m, 2H), 4.08-4.02 (m, 1H), 2.58 (s, 3H), 1.35 (d, J=6.7 Hz, 3H).

Example 47. (6S)-7-[2-Chloro-3-(trifluoromethyl)benzyl]-6-methyl-3-pyridin-4-yl-6,7-dihydro[1,2,4]triazolo[4,3-a]pyrazin-8(5H)-one

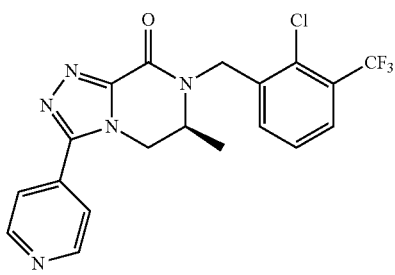 [SMILES: C[C@H]1Cn2c(nnc2-c2ccncc2)C(=O)N1Cc1cccc(C(F)(F)F)c1Cl]

Example 47 was made in a manner analogous to Example 29 substituting isonicotinohydrazide for nicotinohydrazide in Step B to provide the desired compound as a white solid (108 mg, 86%). MS (ESI): mass calcd. for $C_{19}H_{15}ClF_3N_5O$, 421.1; m/z found, 422.1 [M+H]$^+$. $^1$H NMR (500 MHz, CDCl$_3$) δ 8.79-8.75 (m, 2H), 7.74 (d, J=7.7 Hz, 1H), 7.68-7.61 (m, 3H), 7.39 (t, J=7.8 Hz, 1H), 5.34 (d, J=15.6 Hz, 1H), 4.72 (dd, J=13.0, 4.5 Hz, 1H), 4.56 (d, J=15.6 Hz, 1H), 4.32 (dd, J=13.0, 2.0 Hz, 1H), 4.19-4.13 (m, 1H), 1.28 (d, J=6.8 Hz, 3H).

Example 48. (6S)-7-[2-Chloro-3-(trifluoromethyl)benzyl]-6-methyl-3-(2-methylpyridin-3-yl)-6,7-dihydro[1,2,4]triazolo[4,3-a]pyrazin-8(5H)-one

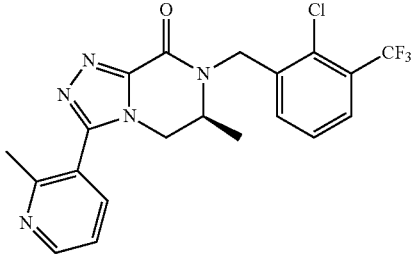 [SMILES: Cc1ncccc1-c1nnc2n1C[C@H](C)N(Cc1cccc(C(F)(F)F)c1Cl)C2=O]

Example 48 was made in a manner analogous to Example 29 substituting Intermediate 14 for nicotinohydrazide in Step B to provide the desired compound as a white solid (73 mg, 56%). MS (ESI): mass calcd. for $C_{20}H_{17}ClF_3N_5O$, 435.1; m/z found, 436.0 [M+H]$^+$. $^1$H NMR (500 MHz, CDCl$_3$) δ 8.67 (dd, J=4.9, 1.7 Hz, 1H), 7.80-7.70 (m, 2H), 7.69-7.66 (m, 1H), 7.40 (t, J=7.8 Hz, 1H), 7.32-7.29 (m, 1H), 5.34 (d, J=15.6 Hz, 1H), 4.57 (d, J=15.6 Hz, 1H), 4.38 (dd, J=13.1, 4.4 Hz, 1H), 4.08-4.01 (m, 1H), 3.84 (dd, J=13.1, 2.0 Hz, 1H), 2.55 (s, 3H), 1.30 (d, J=6.7 Hz, 3H).

Example 49. (6S)-7-[2-Chloro-3-(trifluoromethyl)benzyl]-3-cyclobutyl-6-methyl-6,7-dihydro[1,2,4]triazolo[4,3-a]pyrazin-8(5H)-one

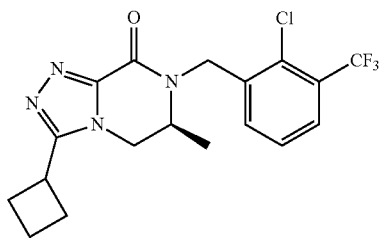 [SMILES: C[C@H]1Cn2c(nnc2C2CCC2)C(=O)N1Cc1cccc(C(F)(F)F)c1Cl]

Example 49 was made in a manner analogous to Example 29 substituting cyclobutanecarbohydrazide for nicotinohydrazide in Step B to provide the desired compound as a white solid (52 mg, 95%). MS (ESI): mass calcd. for $C_{18}H_{18}ClF_3N_4O$, 398.1; m/z found, 399.0 [M+H]$^+$. $^1$H NMR (500 MHz, CDCl$_3$) δ 7.69 (dd, J=13.2, 7.8 Hz, 2H), 7.38 (t, J=7.8 Hz, 1H), 5.38 (d, J=15.5 Hz, 1H), 4.53 (d, J=15.6 Hz, 1H), 4.16 (dd, J=12.8, 4.5 Hz, 1H), 4.05-3.91 (m, 1H), 3.86 (dd, J=12.8, 1.8 Hz, 1H), 3.59-3.51 (m, 1H), 2.66-2.51 (m, 2H), 2.50-2.33 (m, 2H), 2.23-2.00 (m, 2H), 1.29 (t, J=8.2 Hz, 3H).

Example 50. (6S)-7-[2-Chloro-3-(trifluoromethyl)benzyl]-3-cyclopropyl-6-methyl-6,7-dihydro[1,2,4]triazolo[4,3-a]pyrazin-8(5H)-one

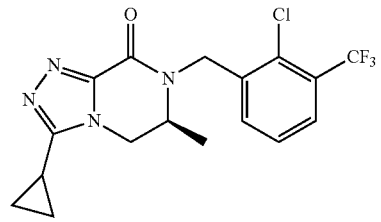 [SMILES: C[C@H]1Cn2c(nnc2C2CC2)C(=O)N1Cc1cccc(C(F)(F)F)c1Cl]

Example 50 was made in a manner analogous to Example 29 substituting cyclopropanecarbohydrazide for nicotinohydrazide in Step B to provide the desired compound as a white solid (76 mg, 83%). MS (ESI): mass calcd. for $C_{17}H_{16}ClF_3N_4O$, 384.1; m/z found, 385.0 [M+H]$^+$. $^1$H NMR (500 MHz, CDCl$_3$) δ 7.70-7.63 (m, 2H), 7.38 (t, J=7.8 Hz, 1H), 5.34 (d, J=15.7 Hz, 1H), 4.53 (d, J=15.7 Hz, 1H), 4.37 (dd, J=13.0, 4.5 Hz, 1H), 4.20 (dd, J=13.0, 2.1 Hz, 1H), 4.10-4.01 (m, 1H), 1.83-1.76 (m, 1H), 1.32 (d, J=6.7 Hz, 3H), 1.23-1.04 (m, 4H).

Example 51. (6S)-7-[2-Chloro-3-(trifluoromethyl) benzyl]-3-cyclohexyl-6-methyl-6,7-dihydro[1,2,4] triazolo[4,3-a]pyrazin-8(5H)-one

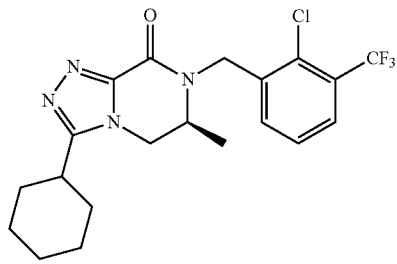 [SMILES: C[C@H]1Cn2c(nnc2C2CCCCC2)C(=O)N1Cc1cccc(C(F)(F)F)c1Cl]

Example 51 was made in a manner analogous to Example 29 substituting cyclohexanecarbohydrazide for nicotinohydrazide in Step B to provide the desired compound as a white solid (62 mg, 61%). MS (ESI): mass calcd. for $C_{20}H_{22}ClF_3N_4O$, 426.1; m/z found, 427.0 [M+H]$^+$. $^1$H NMR (500 MHz, CDCl$_3$) δ 7.78-7.60 (m, 2H), 7.37 (t, J=7.8 Hz, 1H), 5.35 (d, J=15.7 Hz, 1H), 4.53 (d, J=15.7 Hz, 1H), 4.29 (dd, J=12.9, 4.4 Hz, 1H), 4.17-4.00 (m, 2H), 2.76-2.68 (m, 1H), 2.02-1.82 (m, 4H), 1.84-1.61 (m, 3H), 1.43-1.24 (m, 6H).

Example 52. (6S)-3-(5-Chloropyridin-3-yl)-7-[2-chloro-3-(trifluoromethyl)benzyl]-6-methyl-6,7-dihydro[1,2,4]triazolo[4,3-a]pyrazin-8(5H)-one

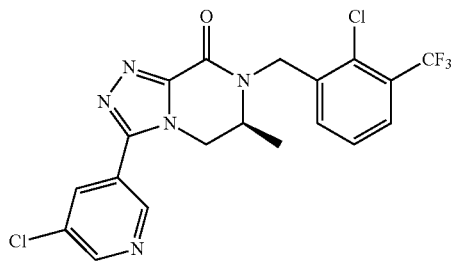 [SMILES: C[C@H]1Cn2c(nnc2-c2cncc(Cl)c2)C(=O)N1Cc1cccc(C(F)(F)F)c1Cl]

Example 52 was made in a manner analogous to Example 29 substituting 5-chloronicotinohydrazide for nicotinohydrazide in Step B to provide the desired compound as a white solid (85 mg, 63%). MS (ESI): mass calcd. for $C_{19}H_{14}Cl_2F_3N_5O$, 455.1; m/z found, 455.9 [M+H]$^+$. $^1$H NMR (400 MHz, CDCl$_3$) δ 8.79 (d, J=1.9 Hz, 1H), 8.70 (d, J=2.3 Hz, 1H), 8.18-8.15 (m, 1H), 7.83-7.74 (m, 1H), 7.70-7.65 (m, 1H), 7.40 (t, J=7.8 Hz, 1H), 5.36 (d, J=15.6 Hz, 1H), 4.69 (dd, J=12.9, 4.5 Hz, 1H), 4.57 (d, J=15.6 Hz, 1H), 4.26 (dd, J=12.9, 2.1 Hz, 1H), 4.21-4.12 (m, 1H), 1.31 (d, J=6.7 Hz, 3H).

Example 53. (6S)-7-[2-Chloro-3-(trifluoromethyl) benzyl]-6-methyl-3-(tetrahydro-2H-pyran-4-yl)-6,7-dihydro[1,2,4]triazolo[4,3-a]pyrazin-8(5H)-one

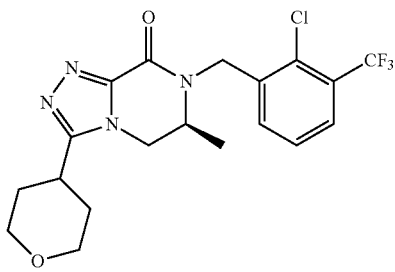 [SMILES: C[C@H]1Cn2c(nnc2C2CCOCC2)C(=O)N1Cc1cccc(C(F)(F)F)c1Cl]

Example 53 was made in a manner analogous to Example 29 substituting tetrahydro-2H-pyran-4-carbohydrazide for nicotinohydrazide in Step B to provide the desired compound as a white solid (83 mg, 65%). MS (ESI): mass calcd. for $C_{19}H_{20}ClF_3N_4O_2$, 428.1; m/z found, 429.0 [M+H]$^+$. $^1$H NMR (400 MHz, CDCl$_3$) δ 7.74-7.63 (m, 2H), 7.38 (t, J=7.8 Hz, 1H), 5.36 (d, J=15.5 Hz, 1H), 4.53 (d, J=15.6 Hz, 1H), 4.32 (dd, J=12.9, 4.5 Hz, 1H), 4.19-3.99 (m, 4H), 3.58-3.48 (m, 2H), 3.09-2.99 (m, 1H), 2.22-1.98 (m, 2H), 1.93-1.80 (m, 2H), 1.31 (d, J=6.7 Hz, 3H).

Example 54. (6S)-7-[2-chloro-3-(trifluoromethyl) benzyl]-6-methyl-3-[4-(trifluoromethyl)pyrimidin-2-yl]-6,7-dihydro[1,2,4]triazolo[4,3-a]pyrazin-8(5H)-one

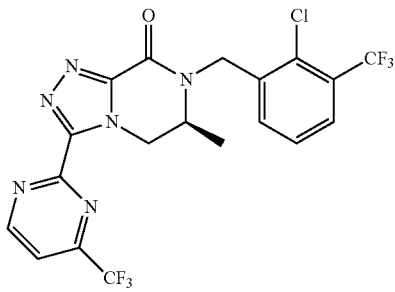 [SMILES: C[C@H]1Cn2c(nnc2-c2nccc(C(F)(F)F)n2)C(=O)N1Cc1cccc(C(F)(F)F)c1Cl]

Example 54 was made in a manner analogous to Example 29 substituting Intermediate 15 for nicotinohydrazide in Step B to provide the desired compound as a white solid (85 mg, 58%). MS (ESI): mass calcd. for $C_{19}H_{13}ClF_6N_6O$, 490.1; m/z found, 490.9 [M+H]$^+$. $^1$H NMR (400 MHz, DMSO-d$_6$) δ 9.42 (d, J=5.1 Hz, 1H), 8.21 (d, J=5.1 Hz, 1H), 7.89-7.81 (m, 2H), 7.57 (t, J=7.8 Hz, 1H), 5.21 (d, J=16.6 Hz, 1H), 4.96 (dd, J=13.9, 2.2 Hz, 1H), 4.81 (dd, J=13.9, 4.6 Hz, 1H), 4.56 (d, J=16.6 Hz, 1H), 4.24-4.15 (m, 1H), 1.22 (d, J=6.6 Hz, 3H).

Example 55. (6S)-7-[2-Chloro-3-(trifluoromethyl)benzyl]-6-methyl-3-[6-(trifluoromethyl)pyridin-2-yl]-6,7-dihydro[1,2,4]triazolo[4,3-a]pyrazin-8(5H)-one

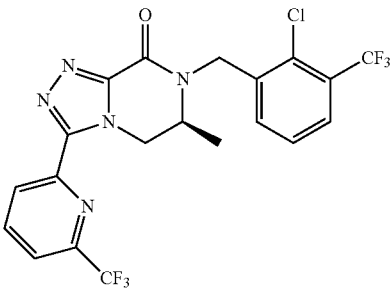 [SMILES: C[C@H]1Cn2c(nnc2-c2cccc(C(F)(F)F)n2)C(=O)N1Cc1cccc(C(F)(F)F)c1Cl]

Example 55 was made in a manner analogous to Example 29 substituting Intermediate 16 for nicotinohydrazide in Step B to provide the desired compound as a white solid (70 mg, 48%). MS (ESI): mass calcd. for $C_{20}H_{14}ClF_6N_6O$, 489.1; m/z found, 489.9 [M+H]$^+$. $^1$H NMR (400 MHz, CDCl$_3$) δ 8.69-8.65 (m, 1H), 7.87-7.82 (m, 1H), 7.80-7.77 (m, 1H), 7.75-7.68 (m, 2H), 7.45-7.38 (m, 1H), 5.47 (d, J=15.5 Hz, 1H), 5.28 (dd, J=14.1, 1.9 Hz, 1H), 4.62-4.55 (m, 2H), 4.10-4.02 (m, 1H), 1.37 (d, J=6.7 Hz, 3H).

Example 56. (6S)-3-(5-Chloropyridin-2-yl)-7-[2-chloro-3-(trifluoromethyl)benzyl]-6-methyl-6,7-dihydro[1,2,4]triazolo[4,3-a]pyrazin-8(5H)-one

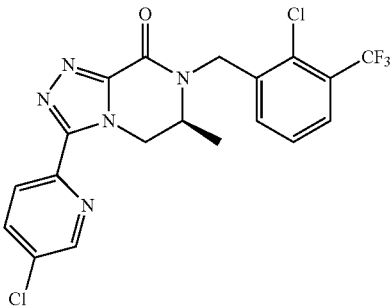 [SMILES: C[C@H]1Cn2c(nnc2-c2ccc(Cl)cn2)C(=O)N1Cc1cccc(C(F)(F)F)c1Cl]

Example 56 was made in a manner analogous to Example 29 substituting Intermediate 17 for nicotinohydrazide in Step B to provide the desired compound as a white solid (61 mg, 45%). MS (ESI): mass calcd. for $C_{19}H_{14}Cl_2F_3N_6O$, 455.1; m/z found, 455.9 [M+H]$^+$. $^1$H NMR (400 MHz, DMSO-d$_6$) δ 8.81 (dd, J=2.5, 0.8 Hz, 1H), 8.32 (dd, J=8.6, 0.7 Hz, 1H), 8.20 (dd, J=8.6, 2.5 Hz, 1H), 7.85-7.81 (m, 2H), 7.55 (t, J=7.8 Hz, 1H), 5.19 (d, J=16.7 Hz, 1H), 5.04 (dd, J=13.9, 2.3 Hz, 1H), 4.79 (dd, J=13.9, 4.6 Hz, 1H), 4.55 (d, J=16.6 Hz, 1H), 4.19-4.11 (m, 1H), 1.22 (d, J=6.7 Hz, 3H).

Example 57. (6S)-7-[2-Chloro-3-(trifluoromethyl)benzyl]-6-methyl-3-(5-methylpyridin-3-yl)-6,7-dihydro[1,2,4]triazolo[4,3-a]pyrazin-8(5H)-one

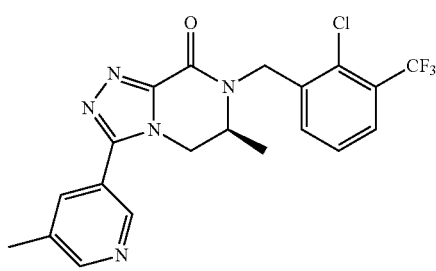 [SMILES: Cc1cncc(-c2nnc3n2C[C@H](C)N(Cc2cccc(C(F)(F)F)c2Cl)C3=O)c1]

Example 57 was made in a manner analogous to Example 29 substituting Intermediate 18 for nicotinohydrazide in Step B to provide the desired compound as a white solid (73 mg, 56%). MS (ESI): mass calcd. for $C_{20}H_{17}ClF_3N_5O$, 435.1; m/z found, 436.0 [M+H]$^+$. $^1$H NMR (500 MHz, CDCl$_3$) δ 8.68-8.60 (m, 2H) 8.03-8.00 (m, 1H), 7.77-7.69 (m, 2H), 7.45-7.39 (m, 1H), 5.44 (d, J=15.4 Hz, 1H), 4.58 (d, J=15.4 Hz, 1H), 4.49 (dd, J=12.9, 4.5 Hz, 1H), 4.17 (dd, J=12.9, 2.0 Hz, 1H), 4.09-4.03 (m, 1H), 2.47-2.43 (m, 3H), 1.30 (d, J=6.8 Hz, 3H).

Example 58. (6S)-tert-Butyl3-{7-[2-chloro-3-(trifluoromethyl)benzyl]-6-methyl-8-oxo-5,6,7,8-tetrahydro[1,2,4]triazolo[4,3-a]pyrazin-3-yl}pyrrolidine-1-carboxylate

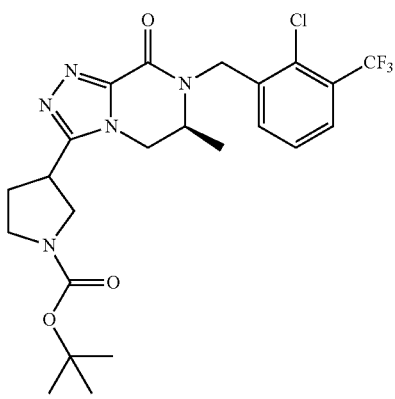 [SMILES: C[C@H]1Cn2c(nnc2C2CCN(C(=O)OC(C)(C)C)C2)C(=O)N1Cc1cccc(C(F)(F)F)c1Cl]

Example 58 was made in a manner analogous to Example 29 substituting (±)-tert-butyl 3-(hydrazinecarbonyl)pyrrolidine-1-carboxylate for nicotinohydrazide in Step B to provide the desired compound as a white solid. MS (ESI): mass calcd. for $C_{23}H_{27}ClF_3N_5O_3$, 513.2; m/z found, 514.2 [M+H]$^+$. $^1$H NMR (400 MHz, CDCl$_3$) δ 7.69 (d, J=7.8 Hz, 2H), 7.43-7.36 (m, 1H), 5.40 (dd, J=15.5, 7.1 Hz, 1H), 4.54 (d, J=15.5 Hz, 1H), 4.32-4.21 (m, 1H), 4.07-3.96 (m, 2H), 3.84-3.78 (m, 1H), 3.76-3.64 (m, 1H), 3.50-3.38 (m, 2H), 2.41-2.30 (m, 1H), 1.68-1.59 (m, 2H), 1.46 (m, 9H), 1.34-1.28 (m, 3H).

Example 59. (6S)-tert-Butyl3-{7-[2-chloro-3-(trifluoromethyl)benzyl]-6-methyl-8-oxo-5,6,7,8-tetrahydro[1,2,4]triazolo[4,3-a]pyrazin-3-yl}piperidine-1-carboxylate

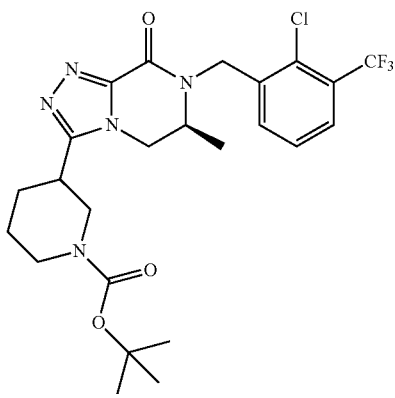 [SMILES: C[C@H]1Cn2c(nnc2C2CCCN(C(=O)OC(C)(C)C)C2)C(=O)N1Cc1cccc(C(F)(F)F)c1Cl]

Example 59 was made in a manner analogous to Example 29 substituting (±)-tert-butyl 3-(hydrazinecarbonyl)piperidine-1-carboxylatecarboxylate for nicotinohydrazide in Step B to provide the desired compound as a white solid (98 mg, 63%). MS (ESI): mass calcd. for $C_{24}H_{29}ClF_3N_5O_3$, 527.2; m/z found, 528.0 [M+H]$^+$. $^1$H NMR (400 MHz, CDCl$_3$) δ 7.71-7.65 (m, 2H), 7.42-7.36 (m, 1H), 5.45-5.35 (m, 1H), 4.56-4.48 (m, 1H), 4.37-3.97 (m, 4H), 3.15-2.68 (m, 3H), 2.27-2.04 (m, 2H), 1.92-1.80 (m, 1H), 1.65-1.52 (m, 2H), 1.48-1.42 (m, 9H), 1.35-1.29 (m, 3H).

Example 60. (6S)-7-[2-Chloro-3-(trifluoromethyl)benzyl]-6-methyl-3-piperidin-3-yl-6,7-dihydro[1,2,4]triazolo[4,3-a]pyrazin-8(5H)-one

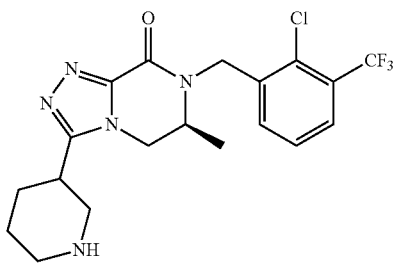 [SMILES: C[C@H]1Cn2c(nnc2C2CCCNC2)C(=O)N1Cc1cccc(C(F)(F)F)c1Cl]

A solution of (±)-tert-butyl 3-(hydrazinecarbonyl)piperidine-1-carboxylatecarboxylate (94 mg, 0.18 mmol) in 1:1 DCM:TFA (2 mL) was stirred at rt for 1 h. The solvent was concentrated to give an oil, which was purified by chromatography (SiO$_2$; 0-50% 10% NH$_3$ in MeOH in DCM) to afford the desired product as a beige solid (70 mg, 92%). MS (ESI): mass calcd. for $C_{19}H_{21}ClF_3N_5O$, 427.1; m/z found, 428.0 [M+H]$^+$. $^1$H NMR (500 MHz, DMSO-d$_6$) δ 7.83 (dd, J=7.8, 1.5 Hz, 1H), 7.80-7.71 (m, 1H), 7.55 (t, J=7.8 Hz, 1H), 5.17 (dd, J=16.5, 6.5 Hz, 1H), 4.59-4.42 (m, 2H), 4.32-4.26 (m, 1H), 4.16-4.08 (m, 1H), 3.49-3.21 (m, 5H), 3.12-3.00 (m, 1H), 2.12-2.01 (m, 1H), 1.93-1.67 (m, 3H), 1.22-1.17 (m, 3H).

Example 61. (±)-7-[2-Chloro-3-(trifluoromethyl)benzyl]-6-cyclopropyl-3-pyrazin-2-yl-6,7-dihydro[1,2,4]triazolo[4,3-a]pyrazin-8(5H)-one

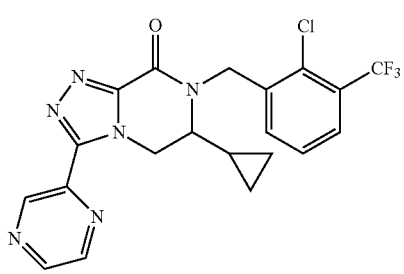 [SMILES: O=C1c2nnc(-c3cnccn3)n2CC(C2CC2)N1Cc1cccc(C(F)(F)F)c1Cl]

Step A. (±)-1-(2-chloro-3-(trifluoromethyl)benzyl)-6-cyclopropyl-3-methoxy-5,6-dihydropyrazin-2(1H)-one To an ice cooled solution of Intermediate 5 (400 mg, 1.2 mmol) and sodium carbonate (2.5 g, 23 mmol) in DCM (45 mL) was added triethyloxonium tetrafluoroborate (1M in DCM, 5.8 mL, 5.8 mmol) dropwise. The ice bath was removed and the reaction was stirred at rt for 1.5 h. Water was added and the mixture was extracted with DCM (×3). The combined organic extracts were dried (Na$_2$SO$_4$), filtered, and concentrated to afford a yellow oil (432 mg, 100%), which was used directly without further purification. MS (ESI): mass calcd. for $C_{17}H_{18}ClF_3N_2O_2$, 374.1; m/z found, 375.1 [M+H]$^+$.

Step B. (±)-7-[2-Chloro-3-(trifluoromethyl)benzyl]-6-cyclopropyl-3-pyrazin-2-yl-6,7-dihydro[1,2,4]triazolo[4,3-a]pyrazin-8(5H)-one A solution of (±)-1-(2-chloro-3-(trifluoromethyl)benzyl)-6-cyclopropyl-3-methoxy-5,6-dihydropyrazin-2(1H)-one (216 mg, 0.58 mmol) and pyrazine-2-carbohydrazide (88 mg, 0.63 mmol) in 1-butanol (5.8 mL) was heated at 130° C. for 16 h. After cooling to rt, the solvent was removed in vacuo. Purification by chromatography (SiO$_2$; hexanes-100% EtOAc) afforded the desired product as a white solid (116 mg, 45%). MS (ESI): mass calcd. for $C_{20}H_{16}ClF_3N_5O$, 448.1; m/z found, 449.1 [M+H]$^+$. $^1$H NMR (400 MHz, CDCl$_3$) δ 9.69-9.58 (m, 1H), 8.70 (d, J=2.6 Hz, 1H), 8.64 (dd, J=2.5, 1.5 Hz, 1H), 7.75-7.62 (m, 2H), 7.38 (t, J=7.8 Hz, 1H), 5.49 (d, J=15.9 Hz, 1H), 5.27-5.16 (m, 1H), 4.78 (dd, J=15.6, 1.7 Hz, 1H), 4.68 (ddd, J=13.9, 4.5, 2.4 Hz, 1H), 3.16 (ddd, J=9.9, 4.5, 3.3 Hz, 1H), 1.06-0.96 (m, 1H), 0.80-0.72 (m, 1H), 0.67-0.43 (m, 2H), 0.28-0.21 (m, 1H).

Example 62. (6R)-7-[2-Chloro-3-(trifluoromethyl)benzyl]-6-cyclopropyl-3-pyrazin-2-yl-6,7-dihydro[1,2,4]triazolo[4,3-a]pyrazin-8(5H)-one

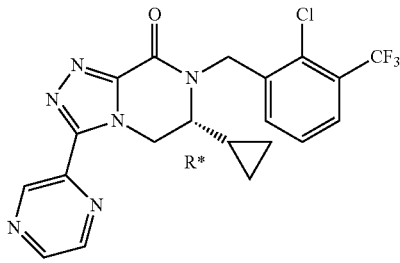 [SMILES: O=C1c2nnc(-c3cnccn3)n2C[C@@H](C2CC2)N1Cc1cccc(C(F)(F)F)c1Cl]

Chiral SFC separation of (±)-7-[2-chloro-3-(trifluoromethyl)benzyl]-6-cyclopropyl-3-pyrazin-2-yl-6,7-dihydro[1,2,4]triazolo[4,3-a]pyrazin-8(5H)-one on a Lux cellulose column (4.5 μM, 250×21.2 mm) using 45% CO$_2$/55% MeOH provided 52 mg of the title compound as the first eluting enantiomer. R$_t$=5.41 min. MS (ESI): mass calcd. for $C_{20}H_{16}ClF_3N_5O$, 448.1; m/z found, 449.2 [M+H]$^+$. $^1$H NMR (500 MHz, CDCl$_3$) δ 9.66 (s, 1H), 8.69 (d, J=2.2 Hz, 1H), 8.62 (d, J=2.3 Hz, 1H), 7.75-7.63 (m, 2H), 7.38 (t, J=7.9 Hz, 1H), 5.50 (d, J=15.8 Hz, 1H), 5.28-5.21 (m, 1H), 4.77 (d, J=15.9 Hz, 1H), 4.72-4.60 (m, 1H), 3.19-3.11 (m, 1H), 1.05-0.96 (m, 1H), 0.81-0.70 (m, 1H), 0.65-0.45 (m, 2H), 0.27-0.19 (m, 1H).

Example 63. (6S)-7-[2-Chloro-3-(trifluoromethyl)benzyl]-6-cyclopropyl-3-pyrazin-2-yl-6,7-dihydro[1,2,4]triazolo[4,3-a]pyrazin-8(5H)-one

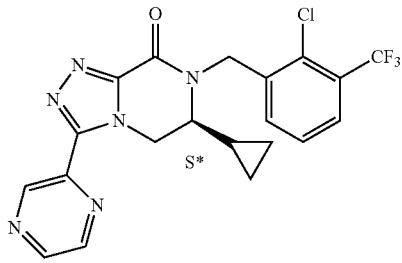 [SMILES: O=C1c2nnc(-c3cnccn3)n2C[C@H](C2CC2)N1Cc1cccc(C(F)(F)F)c1Cl]

Chiral SFC separation of (±)-7-[2-chloro-3-(trifluoromethyl)benzyl]-6-cyclopropyl-3-pyrazin-2-yl-6,7-dihydro[1,2,4]triazolo[4,3-a]pyrazin-8(5H)-one on a Lux cellulose column (4.5 μM, 250×21.2 mm) using 45% $CO_2$/55% MeOH provided 9 mg of the title compound as the second eluting enantiomer. $R_t$=6.33 min. MS (ESI): mass calcd. for $C_{20}H_{16}ClF_3N_5O$, 448.1; m/z found, 449.2 [M+H]$^+$. $^1$H NMR (500 MHz, CDCl$_3$) δ 9.66 (s, 1H), 8.69 (d, J=2.2 Hz, 1H), 8.62 (d, J=2.3 Hz, 1H), 7.75-7.63 (m, 2H), 7.38 (t, J=7.9 Hz, 1H), 5.50 (d, J=15.8 Hz, 1H), 5.28-5.21 (m, 1H), 4.77 (d, J=15.9 Hz, 1H), 4.72-4.60 (m, 1H), 3.19-3.11 (m, 1H), 1.05-0.96 (m, 1H), 0.81-0.70 (m, 1H), 0.65-0.45 (m, 2H), 0.27-0.19 (m, 1H).

Example 64. (±)-7-[2-Chloro-3-(trifluoromethyl)benzyl]-6-cyclopropyl-3-pyrimidin-2-yl-6,7-dihydro[1,2,4]triazolo[4,3-a]pyrazin-8(5H)-one

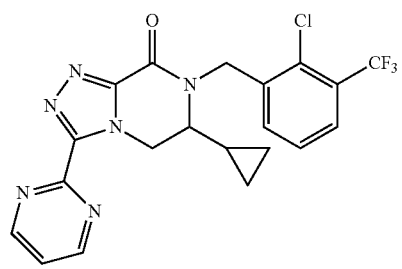 [SMILES: O=C1c2nnc(-c3ncccn3)n2CC(C2CC2)N1Cc1cccc(C(F)(F)F)c1Cl]

Example 64 was made in a manner analogous to Example 61 substituting pyrimidine-2-carbohydrazide for pyrazine-2-carbohydrazide in Step B to provide the desired compound as a white solid (123 mg, 45%). MS (ESI): mass calcd. for $C_{20}H_{16}ClF_3N_5O$, 448.1; m/z found, 449.1 [M+H]$^+$. $^1$H NMR (400 MHz, CDCl$_3$) δ 8.92 (t, J=4.3 Hz, 2H), 7.68-7.64 (m, 2H), 7.44 (t, J=4.9 Hz, 1H), 7.37 (t, J=7.8 Hz, 1H), 5.49 (d, J=16.0 Hz, 1H), 5.29 (dd, J=14.0, 3.4 Hz, 1H), 4.79 (d, J=16.0 Hz, 1H), 4.74-4.65 (m, 1H), 3.20-3.14 (m, 1H), 1.07-0.94 (m, 1H), 0.78-0.68 (m, 1H), 0.61-0.47 (m, 2H), 0.28-0.21 (m, 1H).

Example 65. (6R*)-7-[2-Chloro-3-(trifluoromethyl)benzyl]-6-cyclopropyl-3-pyrimidin-2-yl-6,7-dihydro[1,2,4]triazolo[4,3-a]pyrazin-8(5H)-one

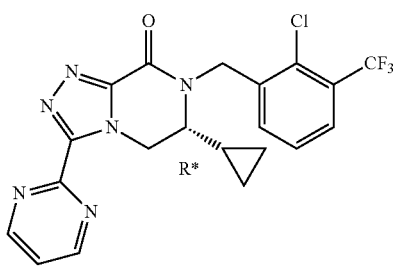 [SMILES: O=C1c2nnc(-c3ncccn3)n2C[C@@H](C2CC2)N1Cc1cccc(C(F)(F)F)c1Cl]

Chiral SFC separation of (±)-7-[2-Chloro-3-(trifluoromethyl)benzyl]-6-cyclopropyl-3-pyrimidin-2-yl-6,7-dihydro[1,2,4]triazolo[4,3-a]pyrazin-8(5H)-one on a CHIRALCEL OJ-H column (5 μM, 250×20 mm) using 85% $CO_2$/15% MeOH provided 76 mg of the title compound as the first eluting enantiomer. $R_t$=5.14 min. MS (ESI): mass calcd. for $C_{20}H_{16}ClF_3N_5O$, 448.1; m/z found, 449.2 [M+H]$^+$. $^1$H NMR (500 MHz, CDCl$_3$) δ 8.93 (d, J=4.8 Hz, 2H), 7.67 (d, J=7.8 Hz, 2H), 7.43 (t, J=4.9 Hz, 1H), 7.38 (t, J=7.8 Hz, 1H), 5.52 (d, J=15.8 Hz, 1H), 5.29 (dd, J=14.0, 3.1 Hz, 1H), 4.78 (d, J=15.8 Hz, 1H), 4.64 (dd, J=13.9, 4.5 Hz, 1H), 3.16-3.10 (m, 1H), 1.05-0.97 (m, 1H), 0.82-0.68 (m, 1H), 0.59-0.48 (m, 2H), 0.29-0.16 (m, 1H).

Example 66. (6S*)-7-[2-Chloro-3-(trifluoromethyl)benzyl]-6-cyclopropyl-3-pyrimidin-2-yl-6,7-dihydro[1,2,4]triazolo[4,3-a]pyrazin-8(5H)-one

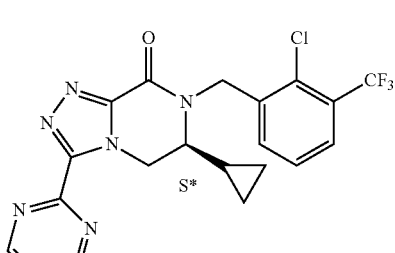

Chiral SFC separation of (±)-7-[2-Chloro-3-(trifluoromethyl)benzyl]-6-cyclopropyl-3-pyrimidin-2-yl-6,7-dihydro[1,2,4]triazolo[4,3-a]pyrazin-8(5H)-one on a CHIRALCEL OJ-H column (5 μM, 250×20 mm) using 85% $CO_2$/15% MeOH provided 19 mg of the title compound as the second eluting enantiomer. $R_t$=6.38 min. MS (ESI): mass calcd. for $C_{20}H_{16}ClF_3N_5O$, 448.1; m/z found, 449.2 [M+H]$^+$. $^1$H NMR (500 MHz, CDCl$_3$) δ 8.93 (d, J=4.8 Hz, 2H), 7.67 (d, J=7.8 Hz, 2H), 7.43 (t, J=4.9 Hz, 1H), 7.38 (t, J=7.8 Hz, 1H), 5.52 (d, J=15.8 Hz, 1H), 5.29 (dd, J=14.0, 3.1 Hz, 1H), 4.78 (d, J=15.8 Hz, 1H), 4.64 (dd, J=13.9, 4.5 Hz, 1H), 3.16-3.10 (m, 1H), 1.05-0.97 (m, 1H), 0.82-0.68 (m, 1H), 0.59-0.48 (m, 2H), 0.29-0.16 (m, 1H).

Example 67. (±)-7-[2-Chloro-3-(trifluoromethyl)benzyl]-6-cyclopropyl-3-pyridin-3-yl-6,7-dihydro[1,2,4]triazolo[4,3-a]pyrazin-8(5H)-one

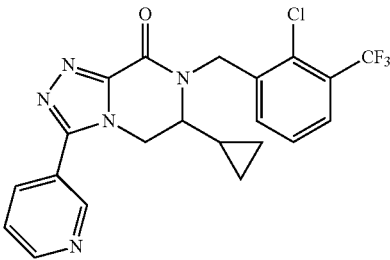 [SMILES: O=C1c2nnc(-c3cccnc3)n2CC(C2CC2)N1Cc1cccc(C(F)(F)F)c1Cl]

Step A. (±)-1-(2-chloro-3-(trifluoromethyl)benzyl)-6-cyclopropyl-3-thioxopiperazin-2-one To a heterogeneous mixture of Lawesson's reagent (289 mg, 0.69 mmol) in THF (13 mL) was added Intermediate 5 (480 mg, 1.4 mmol) in one portion. The mixture was heated at 55° C. for 20 minutes and then concentrated to remove solvent. Purification by chromatography (SiO₂; hexanes-100% EtOAc) afforded the desired product as a yellow solid (434 mg, 86%). MS (ESI): mass calcd. for $C_{15}H_{14}ClF_3N_2OS$, 362.1; m/z found, 363.1 [M+H]⁺. 1H NMR (500 MHz, CDCl₃) δ 9.40 (s, 1H), 7.63 (t, J=8.0 Hz, 2H), 7.36 (t, J=7.8 Hz, 1H), 5.23 (d, J=15.8 Hz, 1H), 4.74 (d, J=15.8 Hz, 1H), 3.73 (ddd, J=13.4, 4.0, 2.1 Hz, 1H), 3.57 (ddd, J=13.5, 5.2, 3.1 Hz, 1H), 2.81 (dd, J=8.5, 4.4 Hz, 1H), 1.24-1.11 (m, 1H), 0.79-0.67 (m, 1H), 0.63-0.55 (m, 1H), 0.51-0.45 (m, 1H), 0.21-0.08 (m, 1H).

Step B. (±)-7-[2-Chloro-3-(trifluoromethyl)benzyl]-6-cyclopropyl-3-pyridin-3-yl-6,7-dihydro[1,2,4]triazolo[4,3-a]pyrazin-8(5H)-one A solution of (±)-1-(2-chloro-3-(trifluoromethyl)benzyl)-6-cyclopropyl-3-thioxopiperazin-2-one (100 mg, 0.28 mmol) and nicotinohydrazide (38 mg, 0.28 mmol) in 1-butanol (3 mL) was heated at 130° C. for 16 h. After cooling to rt, the precipitate was filtered and washed with hexanes to afford the desired product as a white solid (68 mg, 55%). MS (ESI): mass calcd. for $C_{21}H_{17}ClF_3N_5O$, 447.1; m/z found, 448.1 [M+H]⁺. 1H NMR (400 MHz, CDCl₃) δ 8.93 (d, J=1.7 Hz, 1H), 8.79 (dd, J=4.8, 1.6 Hz, 1H), 8.21-8.16 (m, 1H), 7.74-7.61 (m, 2H), 7.52 (dd, J=7.9, 4.9 Hz, 1H), 7.38 (t, J=7.8 Hz, 1H), 5.47 (d, J=15.8 Hz, 1H), 4.76 (d, J=15.8 Hz, 1H), 4.52 (dd, J=12.7, 4.3 Hz, 1H), 4.41 (dd, J=12.7, 3.1 Hz, 1H), 3.18-3.11 (m, 1H), 1.08-0.90 (m, 1H), 0.84-0.69 (m, 1H), 0.59-0.47 (m, 2H), 0.20-0.14 (m, 1H).

Example 68. (±)-7-[2-Chloro-3-(trifluoromethyl)benzyl]-6-cyclopropyl-3-(1H-pyrazol-3-yl)-6,7-dihydro[1,2,4]triazolo[4,3-a]pyrazin-8(5H)-one

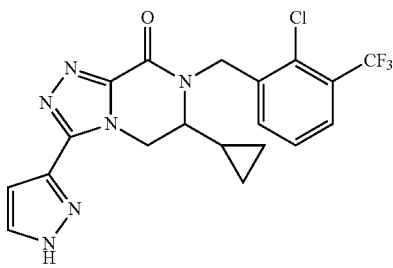 [SMILES: O=C1c2nnc(-c3cc[nH]n3)n2CC(C2CC2)N1Cc1cccc(C(F)(F)F)c1Cl]

Example 68 was made in a manner analogous to Example 67 substituting 1H-pyrazole-3-carbohydrazide for nicotinohydrazide in Step B to provide the desired compound as a white solid (57 mg, 47%). MS (ESI): mass calcd. for $C_{19}H_{16}ClF_3N_5O$, 436.1; m/z found, 437.1 [M+H]⁺. 1H NMR (400 MHz, DMSO-d₆) δ 13.53 (s, 1H), 8.02 (s, 1H), 7.90-7.67 (m, 2H), 7.53 (t, J=7.7 Hz, 1H), 6.94 (s, 1H), 5.21 (d, J=16.7 Hz, 1H), 5.08-4.90 (m, 1H), 4.76 (dd, J=20.7, 10.5 Hz, 2H), 3.51-3.40 (m, 1H), 0.95 (s, 1H), 0.60-0.33 (m, 3H), 0.30-0.17 (m, 1H).

Example 69. (±)-7-[2-Chloro-3-(trifluoromethyl)benzyl]-6-cyclopropyl-3-(5-fluoropyridin-2-yl)-6,7-dihydro[1,2,4]triazolo[4,3-a]pyrazin-8(5H)-one

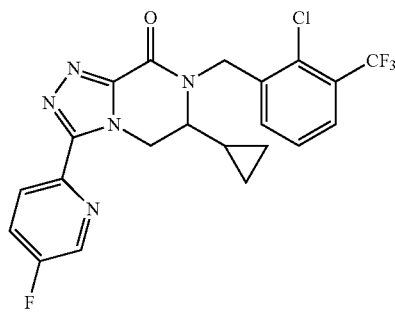 [SMILES: O=C1c2nnc(-c3ccc(F)cn3)n2CC(C2CC2)N1Cc1cccc(C(F)(F)F)c1Cl]

Example 69 was made in a manner analogous to Example 67 substituting 5-fluoropicolinohydrazide for nicotinohydrazide in Step B to provide the desired compound as a white solid (52 mg, 51%). MS (ESI): mass calcd. for $C_{21}H_{16}ClF_4N_5O$, 465.1; m/z found, 465.9 [M+H]⁺. 1H NMR (500 MHz, CDCl₃) δ 8.57-8.42 (m, 2H), 7.66 (d, J=7.8 Hz, 2H), 7.63-7.56 (m, 1H), 7.38 (t, J=7.8 Hz, 1H), 5.49 (d, J=15.9 Hz, 1H), 5.28 (dd, J=13.9, 3.3 Hz, 1H), 4.77 (d, J=15.9 Hz, 1H), 4.72-4.60 (m, 1H), 3.17-3.11 (m, 1H), 1.07-0.94 (m, 1H), 0.79-0.67 (m, 1H), 0.64-0.44 (m, 2H), 0.27-0.20 (m, 1H).

Example 70. (±)-7-[2-Chloro-3-(trifluoromethyl)benzyl]-6-cyclopropyl-3-(5-fluoropyrimidin-2-yl)-6,7-dihydro[1,2,4]triazolo[4,3-a]pyrazin-8(5H)-one

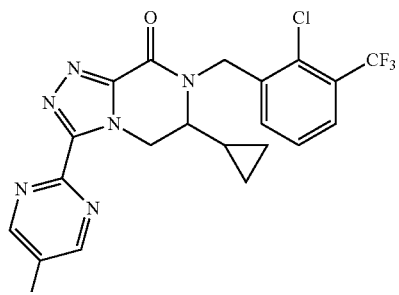

Example 70 was made in a manner analogous to Example 67 substituting 5-fluoropyrimidine-2-carbohydrazide for nicotinohydrazide in Step B to provide the desired compound as a white solid (38 mg, 37%). MS (ESI): mass calcd. for $C_{20}H_{15}ClF_4N_6O$, 466.1; m/z found, 466.9 [M+H]⁺. 1H NMR (500 MHz, CDCl₃) δ 8.79 (d, J=5.6 Hz, 2H), 7.69-

7.64 (m, 2H), 7.37 (t, J=7.8 Hz, 1H), 5.47 (d, J=15.9 Hz, 1H), 5.21 (dd, J=13.9, 3.4 Hz, 1H), 4.79 (d, J=15.9 Hz, 1H), 4.70 (dd, J=13.8, 3.9 Hz, 1H), 3.20-3.15 (m, 1H), 1.04-0.97 (m, 1H), 0.78-0.71 (m, 1H), 0.62-0.43 (m, 2H), 0.27-0.21 (m, 1H).

Example 71. (6S)-7-[2-Chloro-3-(trifluoromethyl) benzyl]-6-ethyl-3-pyrazin-2-yl-6,7-dihydro[1,2,4] triazolo[4,3-a]pyrazin-8(5H)-one

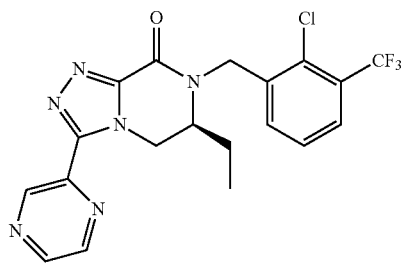 [SMILES: CC[C@H]1Cn2c(nnc2-c2cnccn2)C(=O)N1Cc1cccc(C(F)(F)F)c1Cl]

A solution of Intermediate 6 (100 mg, 0.29 mmol) and pyrazine-2-carbohydrazide (39 mg, 0.29 mmol) in 1-butanol (3 mL) was heated to 130° C. for 16 h. After cooling to rt, the reaction was concentrated to give a brown oil. Purification by chromatography (SiO$_2$; hexanes-100% EtOAc) afforded the desired product as a white solid (94 mg, 75%). MS (ESI): mass calcd. for $C_{19}H_{16}ClF_3N_5O$, 436.1; m/z found, 437.1 [M+H]$^+$. $^1$H NMR (500 MHz, CDCl$_3$) δ 9.62 (d, J=1.5 Hz, 1H), 8.69 (d, J=2.5 Hz, 1H), 8.62 (dd, J=2.5, 1.6 Hz, 1H), 7.77 (d, J=7.7 Hz, 1H), 7.69 (dd, J=7.8, 1.1 Hz, 1H), 7.42 (t, J=7.8 Hz, 1H), 5.56-5.42 (m, 2H), 4.54 (d, J=15.5 Hz, 1H), 4.46 (dd, J=14.1, 4.4 Hz, 1H), 3.77 (ddd, J=9.4, 4.6, 3.5 Hz, 1H), 1.87-1.78 (m, 1H), 1.63-1.53 (m, 1H), 0.97 (t, J=7.4 Hz, 3H).

Example 72. (6S)-7-[2-Chloro-3-(trifluoromethyl) benzyl]-6-ethyl-3-pyrimidin-2-yl-6,7-dihydro[1,2,4] triazolo[4,3-a]pyrazin-8(5H)-one

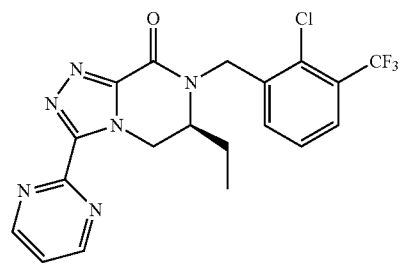 [SMILES: CC[C@H]1Cn2c(nnc2-c2ncccn2)C(=O)N1Cc1cccc(C(F)(F)F)c1Cl]

Example 72 was made in a manner analogous to Example 71 substituting pyrimidine-2-carbohydrazide for pyrazine-2-carbohydrazide to provide the desired compound as a white solid (104 mg, 84%). MS (ESI): mass calcd. for $C_{19}H_{16}ClF_3N_5O$, 436.1; m/z found, 437.1 [M+H]$^+$. $^1$H NMR (400 MHz, CDCl$_3$) δ 8.92 (d, J=4.7 Hz, 2H), 7.76 (d, J=7.7 Hz, 1H), 7.72-7.63 (m, 1H), 7.47-7.38 (m, 2H), 5.56 (dd, J=14.2, 1.2 Hz, 1H), 5.49 (d, J=15.5 Hz, 1H), 4.55 (d, J=15.5 Hz, 1H), 4.47 (dd, J=14.2, 4.4 Hz, 1H), 3.81-3.72 (m, 1H), 1.88-1.76 (m, 1H), 1.66-1.51 (m, 1H), 0.97 (t, J=7.4 Hz, 3H).

Example 73. (6S)-7-[2-Chloro-3-(trifluoromethyl) benzyl]-6-ethyl-3-pyridin-3-yl-6,7-dihydro[1,2,4] triazolo[4,3-a]pyrazin-8(5H)-one

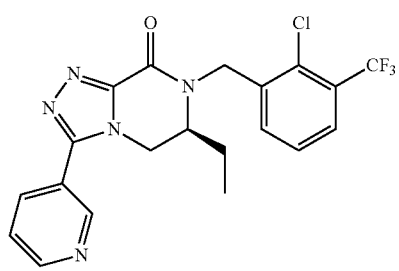 [SMILES: CC[C@H]1Cn2c(nnc2-c2cccnc2)C(=O)N1Cc1cccc(C(F)(F)F)c1Cl]

Example 73 was made in a manner analogous to Example 71 substituting picolinohydrazide for pyrazine-2-carbohydrazide to provide the desired compound as a white solid (96 mg, 77%). MS (ESI): mass calcd. for $C_{20}H_{17}ClF_3N_5O$, 435.1; m/z found, 436.1 [M+H]$^+$. $^1$H NMR (500 MHz, CDCl$_3$) δ 8.92 (s, 1H), 8.78 (s, 1H), 8.18-8.14 (m, 1H), 7.86-7.74 (m, 1H), 7.68 (dd, J=7.8, 1.6 Hz, 1H), 7.53-7.49 (m, 1H), 7.41 (t, J=7.8 Hz, 1H), 5.47 (d, J=15.3 Hz, 1H), 4.62-4.48 (m, 2H), 4.32 (dd, J=13.2, 1.5 Hz, 1H), 3.88-3.77 (m, 1H), 1.22-1.19 (m, 2H), 0.88 (t, J=7.5 Hz, 3H).

Example 74. (6S)-7-[2-Chloro-3-(trifluoromethyl) benzyl]-6-ethyl-3-(1H-pyrazol-3-yl)-6,7-dihydro[1, 2,4]triazolo[4,3-a]pyrazin-8(5H)-one

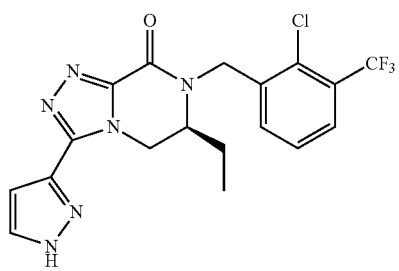 [SMILES: CC[C@H]1Cn2c(nnc2-c2cc[nH]n2)C(=O)N1Cc1cccc(C(F)(F)F)c1Cl]

Example 74 was made in a manner analogous to Example 71 substituting pyrazole-3-carbohydrazide for pyrazine-2-carbohydrazide to provide the desired compound as a white solid (91 mg, 75%). MS (ESI): mass calcd. for $C_{18}H_{16}ClF_3N_5O$, 424.1; m/z found, 425.1 [M+H]$^+$. $^1$H NMR (500 MHz, CDCl$_3$) δ 12.91 (s, 1H), 7.85 (d, J=2.4 Hz, 1H), 7.69-7.66 (m, 2H), 7.39 (t, J=7.8 Hz, 1H), 7.05 (d, J=2.4 Hz, 1H), 5.51 (d, J=15.6 Hz, 1H), 5.33 (t, J=12.8 Hz, 1H), 4.50 (d, J=15.6 Hz, 1H), 4.34 (dd, J=14.1, 4.5 Hz, 1H), 3.74-3.69 (m, 1H), 1.86-1.69 (m, 1H), 1.66-1.47 (m, 1H), 1.00-0.89 (m, 3H).

Example 75. (6S)-7-[2-Chloro-3-(trifluoromethyl)benzyl]-6-ethyl-3-(5-fluoropyrimidin-2-yl)-6,7-dihydro[1,2,4]triazolo[4,3-a]pyrazin-8(5H)-one

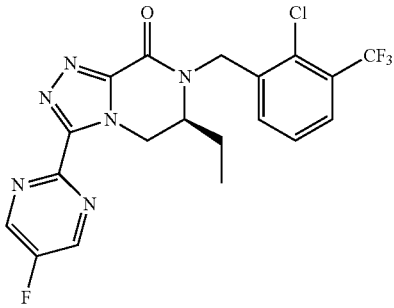 [SMILES: CC[C@H]1Cn2c(nnc2-c2ncc(F)cn2)C(=O)N1Cc1cccc(C(F)(F)F)c1Cl]

Example 75 was made in a manner analogous to Example 71 substituting 5-fluoropyrimidine-3-carbohydrazide for pyrazine-2-carbohydrazide to provide the desired compound as a white solid (14 mg, 22%). MS (ESI): mass calcd. for $C_{19}H_{15}ClF_4N_6O$, 454.1; m/z found, 454.9 [M+H]$^+$. $^1$H NMR (500 MHz, CDCl$_3$) δ 8.78 (s, 2H), 7.76 (d, J=7.7 Hz, 1H), 7.73-7.65 (m, 1H), 7.40 (t, J=7.8 Hz, 1H), 5.50 (d, J=15.4 Hz, 1H), 5.43 (dd, J=14.1, 1.3 Hz, 1H), 4.55 (d, J=15.4 Hz, 1H), 4.41 (dd, J=14.1, 4.3 Hz, 1H), 3.78-3.73 (m, 1H), 1.86-1.77 (m, 1H), 1.63-1.50 (m, 1H), 0.97 (dd, J=9.4, 5.5 Hz, 3H).

Example 76. (6S)-7-[2-Chloro-3-(trifluoromethyl)benzyl]-6-ethyl-3-(5-fluoropyridin-2-yl)-6,7-dihydro[1,2,4]triazolo[4,3-a]pyrazin-8(5H)-one

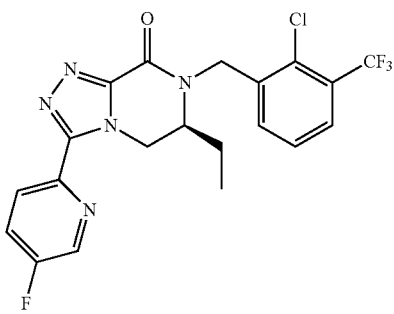

Example 76 was made in a manner analogous to Example 71 substituting 5-fluoropicolinohydrazide for pyrazine-2-carbohydrazide to provide the desired compound as a white solid (30 mg, 46%). MS (ESI): mass calcd. for $C_{20}H_{16}ClF_4N_5O$, 453.1; m/z found, 453.9 [M+H]$^+$. $^1$H NMR (500 MHz, CDCl$_3$) δ 8.55-8.43 (m, 2H), 7.74 (d, J=7.8 Hz, 1H), 7.69 (d, J=7.8 Hz, 1H), 7.63-7.58 (m, 1H), 7.40 (t, J=7.8 Hz, 1H), 5.58-5.44 (m, 2H), 4.53 (d, J=15.4 Hz, 1H), 4.37 (dd, J=14.2, 4.2 Hz, 1H), 3.75-3.70 (m, 1H), 1.84-1.76 (m, 1H), 1.63-1.53 (m, 1H), 1.03-0.94 (m, 3H).

Example 77. (6S)-6-Methyl-3-pyrazin-2-yl-6,7-dihydro[1,2,4]triazolo[4,3-a]pyrazin-8(5H)-one

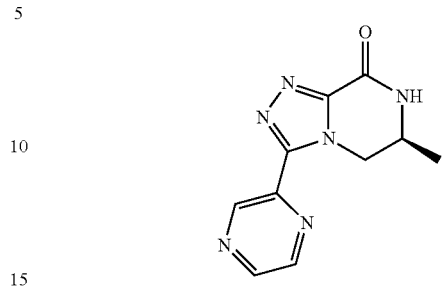

Step A. (S)-tert-butyl (1-(2-chloroacetamido)propan-2-yl)carbamate

To a solution of (S)-tert-butyl (1-aminopropan-2-yl)carbamate hydrochloride (10.0 g, 47.5 mmol) in DCM (300 mL) at −78° C. was added triethylamine (9.9 mL, 71.2 mmol) and chloroacetyl chloride (4.0 mL, 49.8 mmol) and the reaction mixture was warmed to 0° C. and stirred for 1 hour. Water was added and the reaction mixture was extracted with DCM. The organic layers were combined, washed with brine, dried with Na$_2$SO$_4$, filtered, concentrated and purified by flash column chromatography (0-100% EtOAc in hexanes) to provide the desired compound (11.0 g, 92%). $^1$H NMR (400 MHz, DMSO) δ 8.19 (s, 1H), 6.70 (d, J=8.1 Hz, 1H), 4.05 (s, 2H), 3.62-3.47 (m, 1H), 3.13-2.99 (m, 2H), 1.45 (s, 9H), 1.56 (d, J=6.7 Hz, 3H).

Step B. (S)-tert-butyl 2-methyl-5-oxopiperazine-1-carboxylate (S)-tert-butyl (1-(2-chloroacetamido)propan-2-yl)carbamate (7.5 g, 29.9 mmol) was dissolved in trifluoroacetic acid (30 mL) and stirred for 10 minutes. The reaction mixture was concentrated, dissolved in THF (321 mL) and potassium carbonate (20.7 g, 149.5 mmol) was added and the reaction mixture was refluxed for 12 hours. To the reaction mixture was added (Boc)$_2$O (7.7 mL, 35.9 mmol) and the reaction mixture was refluxed for an additional 5 hours. The reaction mixture was cooled to rt and water was added. The reaction mixture was extracted with EtOAc. The organic layers were combined, dried with Na$_2$SO$_4$, filtered, concentrated and purified by flash column chromatography (0-100% EtOAc in hexanes) to provide the desired compound (5 g, 78%). $^1$H NMR (600 MHz, DMSO) δ 8.00 (s, 1H), 4.17 (s, 1H) 3.94 (d, J=17.8 Hz, 1H), 3.58 (d, J=17.9 Hz, 1H), 3.43-3.34 (m, 1H), 3.98 (ddd, J=12.7, 4.9, 2.5 Hz, 1H), 1.43-1.38 (s, 9H), 1.10 (d, J=6.7 Hz, 3H).

Step C. (S)-tert-butyl 2-methyl-5-thioxopiperazine-1-carboxylate

To a suspension of (S)-tert-butyl 2-methyl-5-oxopiperazine-1-carboxylate (7.0 g, 32.7 mmol) was added Lawesson's reagent (6.9 g, 16.7 mmol) and the reaction mixture was heated to 80° C. for 2 hours. The reaction mixture was cooled to room temperature, concentrated onto silica gel and purified by flash column chromatography (0-100% 10% 4M NH$_3$ in MeOH in DCM) to provide the desired compound (5.7 g, 76%). $^1$H NMR (400 MHz, DMSO) δ 10.64 (s, 1H), 4.48 (d, J=18.9 Hz, 1H), 4.31-4.14 (m, 1H), 4.06 (d, J=18.9 Hz, 1H), 3.49-3.41 (m, 1H), 3.13 (ddd, J=13.7, 4.8, 2.9 Hz, 1H), 1.43 (s, 9H), 1.07 (d, J=6.6 Hz, 3H).

Step D. (S)-tert-butyl 6-methyl-3-(pyrazin-2-yl)-5,6-dihydro-[1,2,4]triazolo[4,3-a]pyrazine-7(8H)-carboxylate To a suspension of (S)-tert-butyl 2-methyl-5-thioxopiperazine-1-carboxylate (2.5 g, 10.9 mmol) in n-butanol (10 mL) was added pyrazine-2-carbohydrazide (1.6 g, 11.9 mmol) and the reaction mixture was heated to 120° C. for 12 hours. The reaction mixture as cooled to room temperature, concentrated onto silica gel and purified by flash column chromatography (0-20% MeOH in EtOAc) to provide the desired compound (1.5 g, 43%). $^1$H NMR (400 MHz, DMSO) δ 9.36 (d, J=1.4 Hz, 1H), 8.78-8.74 (m, 2H), 5.02 (d, J=17.4 Hz, 1H), 4.72 (d, J=12.6 Hz, 2H), 4.53 (d, J=17.4 Hz, 1H), 4.36-4.28 (m, 1H), 1.48 (s, 9H), 1.10 (d, J=6.9 Hz, 3H).

Step E. (S)-tert-butyl 6-methyl-8-oxo-3-(pyrazin-2-yl)-5,6-dihydro-[1,2,4]triazolo[4,3-a]pyrazine-7(8H)-carboxylate To a solution of (S)-tert-butyl 6-methyl-3-(pyrazin-2-yl)-5,6-dihydro-[1,2,4]triazolo[4,3-a]pyrazine-7(8H)-carboxylate (1.0 g, 3.2 mmol) in chloroform (12 mL) was added acetonitrile (12 mL), water (30 mL), sodium metaperiodate (3.2 g, 14.9 mmol) and ruthenium (IV) oxide hydrate (62 mg, 0.4 mmol) and the reaction mixture was vigorously stirred for 30 minutes. The reaction mixture was filtered through celite, extracted with DCM, the organic layers were washed with brine, dried with Na$_2$SO$_4$, filtered, concentrated and purified by flash column chromatography (0-100% EtOAc in hexanes) to provide the desired compound (0.50 g, 48%). $^1$H NMR (400 MHz, DMSO) δ 9.47 (s, 1H), 8.83 (s, 2H), 5.01-4.92 (m, 1H), 4.89-4.79 (m, 1H), 4.73-4.66 (m, 1H), 1.52 (s, 9H), 1.21 (d, J=6.8 Hz, 3H).

Step F. (S)-6-methyl-3-(pyrazin-2-yl)-6,7-dihydro-[1,2,4]triazolo[4,3-a]pyrazin-8(5H)-one To a solution of (S)-tert-butyl 6-methyl-8-oxo-3-(pyrazin-2-yl)-5,6-dihydro-[1,2,4]triazolo[4,3-a]pyrazine-7(8H)-carboxylate (0.4 g, 1.2 mmol) in DCM (12 mL) was added trifluoroacetic acid (2.5 mL, 31.7 mmol) and the reaction mixture was stirred for 1 hour at room temperature. The reaction mixture was concentrated and EtOAc (10 mL) was added. The resulting precipitate was collected via filtration and dried to provide the desired compound (267 mg, 64%). MS (ESI): mass calcd. for C$_{10}$H$_{10}$N$_6$O, 230.2; m/z found, 231.1 [M+H]$^+$. $^1$H NMR (400 MHz, DMSO) δ 9.44 (d, J=1.4 Hz, 1H), 8.85-8.81 (m, 2H), 8.69 (s, 1H), 4.92 (m, 1H), 4.31-4.23 (m, 1H), 4.10-3.96 (m, 1H), 1.24 (d, J=6.6 Hz, 3H).

Example 78. (6S)-7-(2-Chloro-4-fluorobenzyl)-6-methyl-3-pyrazin-2-yl-6,7-dihydro[1,2,4]triazolo[4,3-a]pyrazin-8(5H)-one

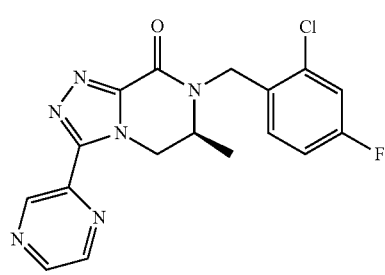 [SMILES: C[C@H]1Cn2c(nnc2-c2cnccn2)C(=O)N1Cc1ccc(F)cc1Cl]

To a solution of Example 77 (40 mg, 0.17 mmol) in DMF (1.7 mL) was added cesium carbonate (226 mg, 0.70 mmol) and 2-chloro-4-fluorobenzyl bromide (58 mg, 0.26 mmol) and the reaction mixture was stirred for 18 hours. The reaction mixture was diluted with water and extracted with EtOAc. The organic layers were combined, washed with brine, dried with Na$_2$SO$_4$, filtered, concentrated and purified by flash column chromatography (0-20% iPrOH in EtOAc) to provide the desired compound (41 mg, 65%). MS (ESI): mass calcd. for C$_{17}$H$_{14}$ClFN$_6$O, 372.8; m/z found, 373.1 [M+H]$^+$. $^1$H NMR (400 MHz, DMSO) δ 9.47 (d, J=1.3 Hz, 1H), 8.84-8.80 (m, 2H), 7.61-7.55 (m, 1H), 7.55-7.50 (m, 1H), 7.26-7.19 (m, 1H), 5.10 (d, J=15.9 Hz, 1H), 5.01-4.89 (m, 1H), 4.70 (dd, J=13.9, 4.6 Hz, 1H), 4.48 (d, J=16.0 Hz, 1H), 4.13-4.03 (m, 1H), 1.18 (d, J=6.7 Hz, 3H).

Example 79. (6S)-7-Benzyl-6-methyl-3-pyrazin-2-yl-6,7-dihydro[1,2,4]triazolo[4,3-a]pyrazin-8(5H)-one

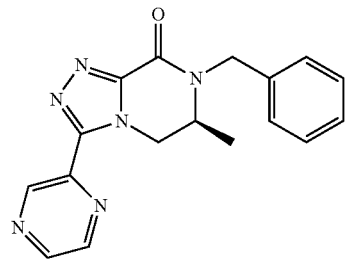

Example 79 was made in a manner analogous to Example 78 substituting benzyl bromide for chloro-4-fluorobenzyl bromide to provide the desired compound (15 mg, 26%). MS (ESI): mass calcd. for C$_{17}$H$_{16}$N$_6$O, 320.4; m/z found, 321.2 [M+H]$^+$. $^1$H NMR (400 MHz, DMSO) δ 9.48-9.44 (m, 1H), 8.84-8.78 (m, 2H), 7.44-7.27 (m, 5H), 5.12 (d, J=15.4 Hz, 1H), 4.96-4.89 (m, 1H), 4.65-4.57 (m, 1H), 4.45 (d, J=15.3 Hz, 1H), 4.09-3.99 (m, 1H), 1.13 (d, J=6.7 Hz, 3H).

Example 80. (6S)-7-(2-Chlorobenzyl)-6-methyl-3-pyrazin-2-yl-6,7-dihydro[1,2,4]triazolo[4,3-a]pyrazin-8(5H)-one

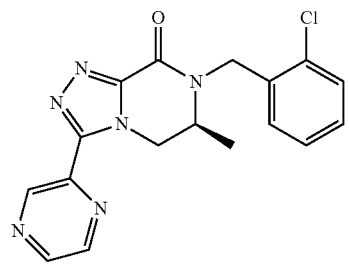

Example 80 was made in a manner analogous to Example 78 substituting 2-chlorobenzyl chloride for chloro-4-fluorobenzyl bromide to provide the desired compound (47 mg, 76%). MS (ESI): mass calcd. for C$_{17}$H$_{15}$ClN$_6$O, 354.8; m/z found, 355.1 [M+H]$^+$. $^1$H NMR (400 MHz, DMSO) δ 9.47 (d, J=1.2 Hz, 1H), 8.83 (m, 2H), 7.52 (m, 2H), 7.36 (m, 2H), 5.15 (d, J=16.1 Hz, 1H), 5.01-4.92 (m, 1H), 4.78-4.68 (m, 1H), 4.48 (d, J=16.1 Hz, 1H), 4.13-4.04 (m, 1H), 1.19 (d, J=6.7 Hz, 3H).

Example 81. (6S)-7-[2-Chloro-4-(methylsulfonyl)benzyl]-6-methyl-3-pyrazin-2-yl-6,7-dihydro[1,2,4]triazolo[4,3-a]pyrazin-8(5H)-one

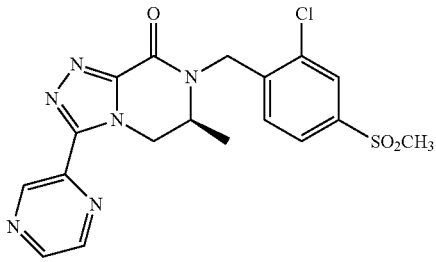 [SMILES: C[C@H]1Cn2c(nnc2-c2cnccn2)C(=O)N1Cc1ccc(S(C)(=O)=O)cc1Cl]

Example 81 was made in a manner analogous to Example 78 substituting 1-(bromomethyl)-2-chloro-4-(methylsulfonyl)benzene for chloro-4-fluorobenzyl bromide for chloro-4-fluorobenzyl bromide to provide the desired compound (36 mg, 57%). MS (ESI): mass calcd. for $C_{18}H_{17}ClN_6O_3S$, 432.9; m/z found, 433.1 [M+H]$^+$. $^1$H NMR (400 MHz, DMSO) δ 9.49 (d, J=1.0 Hz, 1H), 8.87-8.79 (m, 2H), 8.04 (d, J=1.7 Hz, 1H), 7.89-7.76 (m, 2H), 5.19 (d, J=16.9 Hz, 1H), 5.04-4.93 (m, 1H), 4.88-4.76 (m, 1H), 4.56 (d, J=16.8 Hz, 1H), 4.21 (s, 1H), 3.30 (s, 3H), 1.24 (d, J=6.6 Hz, 3H).

Example 82. (6S)-7-[4-Chloro-2-(methylsulfonyl)benzyl]-6-methyl-3-pyrazin-2-yl-6,7-dihydro[1,2,4]triazolo[4,3-a]pyrazin-8(5H)-one

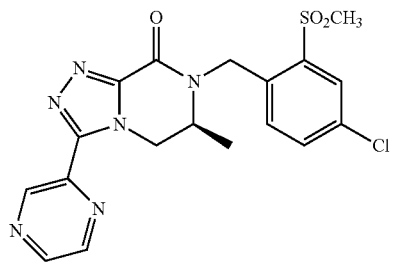 [SMILES: C[C@H]1Cn2c(nnc2-c2cnccn2)C(=O)N1Cc1ccc(Cl)cc1S(C)(=O)=O]

Example 82 was made in a manner analogous to Example 78 substituting 1-(bromomethyl)-4-chloro-2-(methylsulfonyl)benzene for chloro-4-fluorobenzyl bromide for chloro-4-fluorobenzyl bromide to provide the desired compound (35 mg, 56%). MS (ESI): mass calcd. for $C_{18}H_{17}ClN_6O_3S$, 432.9; m/z found, 433.1 [M+H]$^+$. $^1$H NMR (400 MHz, DMSO) δ 9.48 (d, J=0.9 Hz, 1H), 8.84 (s, 2H), 7.95 (d, J=2.1 Hz, 1H), 7.79-7.69 (m, 2H), 5.44 (d, J=16.8 Hz, 1H), 5.00-4.91 (m, 1H), 4.88-4.76 (m, 2H), 4.21-4.12 (m, 1H), 3.45 (s, 3H), 1.21 (d, J=6.7 Hz, 3H).

Example 83. (6S)-6-Methyl-3-pyrazin-2-yl-7-[2-(trifluoromethoxy)benzyl]-6,7-dihydro[1,2,4]triazolo[4,3-a]pyrazin-8(5H)-one

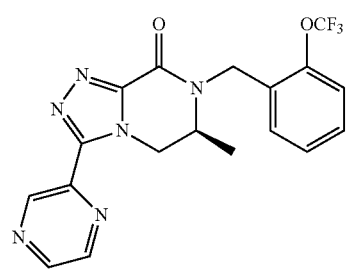

Example 83 was made in a manner analogous to Example 78 substituting 1-(bromomethyl)-2-(trifluoromethoxy)benzene for chloro-4-fluorobenzyl bromide to provide the desired compound (41 mg, 53%). MS (ESI): mass calcd. for $C_{18}H_{15}F_3N_6O_2$, 404.4; m/z found, 405.2 [M+H]$^+$. $^1$H NMR (400 MHz, DMSO) δ 9.47 (d, J=1.3 Hz, 1H), 8.85-8.79 (m, 2H), 7.65-7.36 (m, 4H), 5.16 (d, J=16.0 Hz, 1H), 5.00-4.88 (m, 1H), 4.74-4.62 (m, 1H), 4.49 (d, J=16.0 Hz, 1H), 4.14-3.98 (m, 1H), 1.17 (d, J=6.7 Hz, 3H).

Example 84. (6S)-7-[(6-Chloro-1,3-benzodioxol-5-yl)methyl]-6-methyl-3-pyrazin-2-yl-6,7-dihydro[1,2,4]triazolo[4,3-a]pyrazin-8(5H)-one

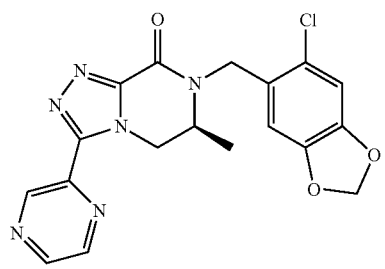 [SMILES: C[C@H]1Cn2c(nnc2-c2cnccn2)C(=O)N1Cc1cc2c(cc1Cl)OCO2]

Example 84 was made in a manner analogous to Example 78 substituting 6-chloropiperonyl chloride for chloro-4-fluorobenzyl bromide to provide the desired compound (27 mg, 51%). MS (ESI): mass calcd. for $C_{18}H_{15}ClN_6O_3$, 398.8; m/z found, 399.1 [M+H]$^+$. $^1$H NMR (400 MHz, DMSO) δ 9.47 (d, J=0.9 Hz, 1H), 8.90-8.77 (m, 2H), 7.13 (d, J=11.4 Hz, 2H), 6.0 (s, 2H), 5.4 (d, J=15.8 Hz, 1H), 4.99-4.87 (m, 1H), 4.72-4.62 (m, 1H), 4.38 (d, J=15.8 Hz, 1H), 4.09-3.99 (m, 1H), 1.18 (d, J=6.7 Hz, 3H).

Example 85. (6S)-6-Methyl-7-[2-methyl-3-(trifluoromethyl)benzyl]-3-pyrazin-2-yl-6,7-dihydro[1,2,4]triazolo[4,3-a]pyrazin-8(5H)-one

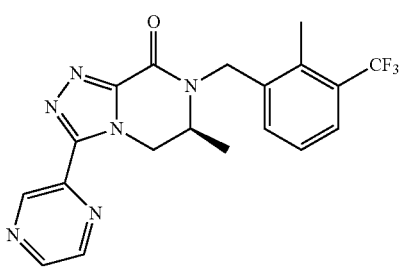

Example 85 was made in a manner analogous to Example 78 substituting 2-methyl-3-(trifluoromethyl)benzyl bromide for chloro-4-fluorobenzyl bromide to provide the desired compound (45 mg, 29%). MS (ESI): mass calcd. for $C_{19}H_{17}F_3N_6O$, 402.4; m/z found, 403.2 [M+H]$^+$. $^1$H NMR (400 MHz, DMSO) δ 9.48 (d, J=1.3 Hz, 1H), 8.86-8.79 (m, 2H), 7.70-7.63 (m, 2H), 7.43-7.37 (m, 1H), 5.22 (d, J=16.1 Hz, 1H), 5.02-4.91 (m, 1H), 4.79-4.69 (m, 1H), 4.53 (d, J=16.2 Hz, 1H), 4.05-3.93 (m, 1H), 2.42 (s, 3H), 1.22 (d, J=6.7 Hz, 3H).

Example 86. (6S)-7-(2,6-Dichlorobenzyl)-6-methyl-3-pyrazin-2-yl-6,7-dihydro[1,2,4]triazolo[4,3-a]pyrazin-8(5H)-one

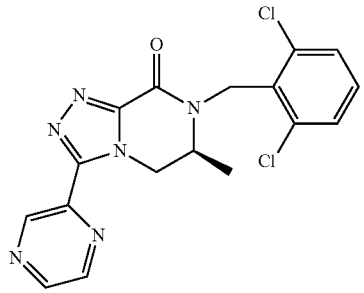 [SMILES: C[C@H]1Cn2c(nnc2-c2cnccn2)C(=O)N1Cc1c(Cl)cccc1Cl]

Example 86 was made in a manner analogous to Example 78 substituting 2,6-dichlorobenzyl bromide for chloro-4-fluorobenzyl bromide to provide the desired compound (65 mg, 42%). MS (ESI): mass calcd. for $C_{17}H_{14}Cl_2N_6O$, 389.3; m/z found, 390.1 [M+H]$^+$. $^1$H NMR (400 MHz, DMSO) δ 9.43 (d, J=1.5 Hz, 1H), 8.80 (d, J=2.6 Hz, 1H), 8.78-8.75 (m, 1H), 7.62-7.55 (m, 2H), 7.48-7.41 (m, 1H), 5.40 (d, J=14.6 Hz, 1H), 5.00-4.90 (m, 1H), 4.60 (d, J=14.6 Hz, 1H), 4.42-4.28 (m, 1H), 3.87-3.70 (m, 1H), 1.19 (d, J=6.7 Hz, 3H).

Example 87. (6S)-7-(2,6-Dimethylbenzyl)-6-methyl-3-pyrazin-2-yl-6,7-dihydro[1,2,4]triazolo[4,3-a]pyrazin-8(5H)-one

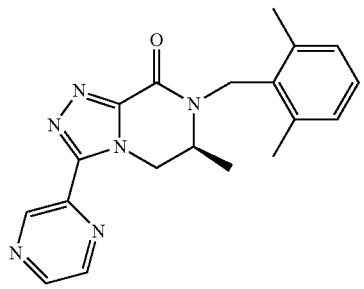 [SMILES: Cc1cccc(C)c1CN1C(=O)c2nnc(-c3cnccn3)n2C[C@@H]1C]

Example 87 was made in a manner analogous to Example 78 substituting 2,6-dimethylbenzyl bromide for chloro-4-fluorobenzyl bromide to provide the desired compound (71 mg, 52%). MS (ESI): mass calcd. for $C_{19}H_{20}N_6O$, 348.4; m/z found, 349.2 [M+H]$^+$. $^1$H NMR (400 MHz, DMSO) δ 9.44 (d, J=1.5 Hz, 1H), 8.79 (d, J=2.6 Hz, 1H), 8.77-8.74 (m, 1H), 7.20-7.04 (m, 3H), 5.20 (d, J=14.9 Hz, 1H), 4.96-4.82 (m, 1H), 4.51-4.42 (d, J=14.8 Hz, 1H), 4.38-4.25 (m, 1H), 3.69-3.58 (m, 1H), 2.34 (s, 6H), 1.10 (d, J=6.7 Hz, 3H).

Example 88. (6S)-6-Methyl-3-pyrazin-2-yl-7-[3-(trifluoromethyl)benzyl]-6,7-dihydro[1,2,4]triazolo[4,3-a]pyrazin-8(5H)-one

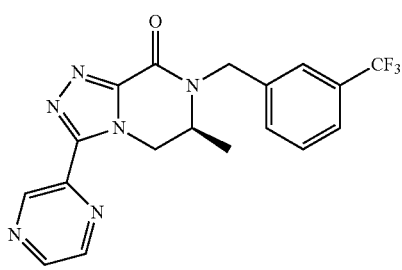 [SMILES: C[C@H]1Cn2c(nnc2-c2cnccn2)C(=O)N1Cc1cccc(C(F)(F)F)c1]

Example 88 was made in a manner analogous to Example 78 substituting 3-(trifluoromethyl)benzyl bromide for chloro-4-fluorobenzyl bromide to provide the desired compound (66 mg, 43%). MS (ESI): mass calcd. for $C_{18}H_{15}F_3N_6O$, 388.4; m/z found, 389.2 [M+H]$^+$. $^1$H NMR (400 MHz, DMSO) δ 9.47 (d, J=1.3 Hz, 1H), 8.84-8.79 (m, 2H), 7.82-7.56 (m, 4H), 5.20 (d, J=15.7 Hz, 1H), 4.98-4.90 (m, 1H), 4.69-4.61 (m, 1H), 4.54 (d, J=15.7 Hz, 1H), 4.17-4.02 (m, 1H), 1.17 (d, J=6.7 Hz, 3H).

Example 89. (6S)-6-Methyl-7-(2-nitrobenzyl)-3-pyrazin-2-yl-6,7-dihydro[1,2,4]triazolo[4,3-a]pyrazin-8(5H)-one

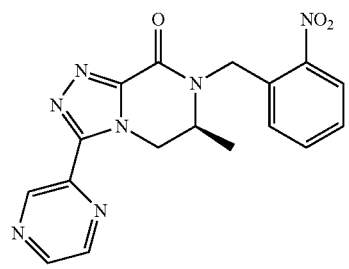 [SMILES: C[C@H]1Cn2c(nnc2-c2cnccn2)C(=O)N1Cc1ccccc1[N+](=O)[O-]]

Example 89 was made in a manner analogous to Example 78 substituting 2-nitrobenzyl chloride for chloro-4-fluorobenzyl bromide to provide the desired compound (82 mg, 57%). MS (ESI): mass calcd. for $C_{17}H_{15}N_7O_3$, 365.4; m/z found, 366.1 [M+H]$^+$. $^1$H NMR (400 MHz, DMSO) δ 9.59 (d, J=1.2 Hz, 1H), 8.85-8.81 (m, 2H), 8.12 (d, J=7.8 Hz, 1H), 7.79-7.68 (m, 2H), 7.65-7.55 (m, 1H), 5.43 (d, J=17.2 Hz, 1H), 5.02-4.93 (m, 1H), 4.82-4.76 (m, 1H), 4.71 (d, J=17.2 Hz, 1H), 4.13-4.01 (m, 1H), 1.20 (d, J=6.7 Hz, 3H).

Example 90. (6S)-7-(2-Chloro-5-nitrobenzyl)-6-methyl-3-pyrazin-2-yl-6,7-dihydro[1,2,4]triazolo[4,3-a]pyrazin-8(5H)-one

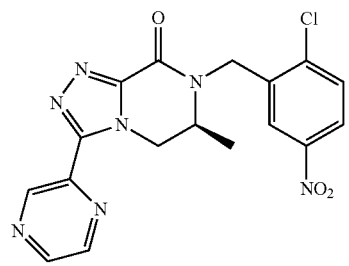 [SMILES: C[C@H]1Cn2c(nnc2-c2cnccn2)C(=O)N1Cc1cc([N+](=O)[O-])ccc1Cl]

Example 90 was made in a manner analogous to Example 78 substituting 2-(bromomethyl)-1-chloro-4-nitrobenzene for chloro-4-fluorobenzyl bromide to provide the desired compound (25 mg, 35%). MS (ESI): mass calcd. for $C_{17}H_{14}ClN_7O_3$, 399.8; m/z found, 400.1 [M+H]$^+$. $^1$H NMR (400 MHz, DMSO) δ 9.48 (d, J=1.3 Hz, 1H), 8.87-8.78 (m, 2H), 8.29 (d, J=2.7 Hz, 1H), 8.19 (dd, J=8.8, 2.8 Hz, 1H), 7.84 (d, J=8.7 Hz, 1H), 5.20 (d, J=16.1 Hz, 1H), 5.00-4.92 (m, 1H), 4.69 (dd, J=13.9, 4.6 Hz, 1H), 4.60 (d, J=16.2 Hz, 1H), 4.27 (s, 1H), 1.21 (d, J=6.7 Hz, 3H).

Example 91. (6S)-7-(5-Amino-2-chlorobenzyl)-6-methyl-3-pyrazin-2-yl-6,7-dihydro[1,2,4]triazolo[4,3-a]pyrazin-8(5H)-one

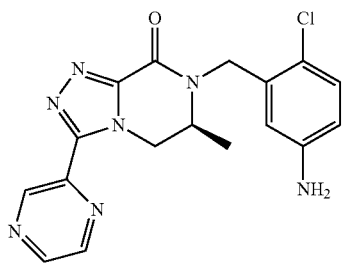

To a solution of Example 90 (20 mg, 0.05 mmol) in acetone (0.4 mL) and water (0.1 ml) was added zinc dust (33 mg, 0.5 mmol) followed by ammonium chloride (27 mg, 0.5 mmol) and the reaction mixture was stirred for 10 minutes. The reaction mixture was filtered through a pad of celite, extracted with DCM and the organic layers were collected. The organic layers were washed with brine, dried with $Na_2SO_4$, filtered, concentrated and purified by reverse-phase HPLC to provide the desired compound (5 mg, 27%). MS (ESI): mass calcd. for $C_{17}H_{16}ClN_7O$, 369.8; m/z found, 370.2 [M+H]$^+$. $^1$H NMR (400 MHz, DMSO) δ 9.48 (d, J=1.2 Hz, 1H), 8.87-8.79 (m, 2H), 7.15 (d, J=8.5 Hz, 1H), 6.74 (s, 1H), 6.59 (d, J=8.4 Hz, 1H), 5.06 (d, J=16.3 Hz, 1H), 4.96 (d, J=11.9 Hz, 1H), 4.81-4.68 (m, 1H), 4.34 (d, J=16.1 Hz, 1H), 4.06 (s, 1H), 1.17 (d, J=6.7 Hz, 3H).

Example 92. (6S)-6-Methyl-7-(1-phenylethyl)-3-pyrazin-2-yl-6,7-dihydro[1,2,4]triazolo[4,3-a]pyrazin-8(5H)-one

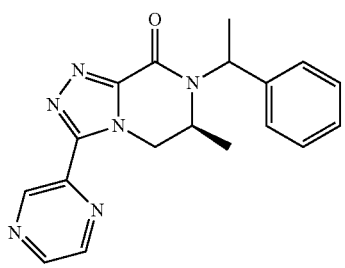 [SMILES: CC(c1ccccc1)N1C(=O)c2nnc(-c3cnccn3)n2C[C@@H]1C]

Example 92 was made in a manner analogous to Example 78 substituting (1-bromoethyl)benzene for chloro-4-fluorobenzyl bromide to provide the desired compound (32 mg, 44%). MS (ESI): mass calcd. for $C_{18}H_{18}N_6O$, 334.4; m/z found, 335.2 [M+H]$^+$. $^1$H NMR (400 MHz, DMSO) δ 9.44 (d, J=1.6 Hz, 1H), 8.84-8.73 (m, 2H), 7.53-7.29 (m, 5H), 6.08-5.69 (m, 1H), 4.94-4.74 (m, 1H), 4.65-4.46 (m, 0.4H), 4.28-4.11 (m, 1H), 4.02-3.78 (m, 0.6H), 1.75-1.55 (m, 3H), 1.19 (d, J=6.7 Hz, 2H), 0.49 (d, J=6.7 Hz, 1H).

Example 93. (6S)-6-Methyl-7-[(1R/S)-1-phenylethyl]-3-pyrazin-2-yl-6,7-dihydro[1,2,4]triazolo[4,3-a]pyrazin-8(5H)-one

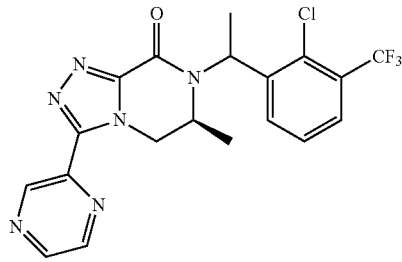 [SMILES: CC(c1cccc(C(F)(F)F)c1Cl)N1C(=O)c2nnc(-c3cnccn3)n2C[C@@H]1C]

Example 93 was made in a manner analogous to Example 78 substituting 1-(2-chloro-3-(trifluoromethyl)phenyl)ethyl methanesulfonate-for chloro-4-fluorobenzyl bromide to provide the desired compound (15 mg, 7.9%). MS (ESI): mass calcd. for $C_{19}H_{16}ClF_3N_5O$, 436.8; m/z found, 437.2 [M+H]$^+$. $^1$H NMR (400 MHz, DMSO) δ 9.47-9.41 (m, 1H), 8.83-8.76 (m, 2H), 8.13-7.56 (m, 3H), 6.09-3.47 (m, 4H), 1.79-1.64 (m, 3H), 1.29-0.54 (m, 3H).

The diastereomers in Example 93 were separated via supercritical fluid chromatography (stationary phase: Chiralpak AD-H 5 µm 250×21 mm: mobile phase 30% ethanol, 70% $CO_2$) to provide example 94 and 95 as pure diastereomers.

Example 94. (6S)-6-Methyl-7-[(1R*)-1-phenylethyl]-3-pyrazin-2-yl-6,7-dihydro[1,2,4]triazolo[4,3-a]pyrazin-8(5H)-one

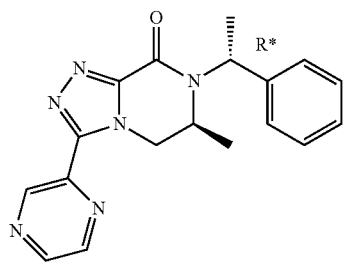 [SMILES: C[C@H](c1ccccc1)N1C(=O)c2nnc(-c3cnccn3)n2C[C@@H]1C]

MS (ESI): mass calcd. for $C_{18}H_{18}N_6O$, 334.4; m/z found, 335.2 [M+H]$^+$. $^1$H NMR (500 MHz, DMSO) δ 9.44 (d, J=1.4 Hz, 1H), 8.79 (d, J=2.6 Hz, 1H), 8.77-8.75 (m, 1H), 7.49-7.43 (m, 2H), 7.42-7.37 (m, 2H), 7.36-7.30 (m, 1H), 5.88-5.80 (m, 1H), 4.88-4.79 (m, 1H), 4.26-4.15 (m, 1H), 3.92-3.80 (m, 1H), 1.67 (d, J=7.2 Hz, 3H), 1.19 (d, J=6.7 Hz, 3H).

Example 95. (6S)-6-Methyl-7-[(1S*)-1-phenylethyl]-3-pyrazin-2-yl-6,7-dihydro[1,2,4]triazolo[4,3-a]pyrazin-8(5H)-one

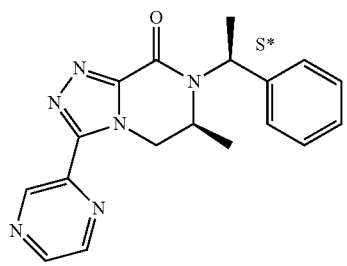 [SMILES: C[C@H]1Cn2c(nnc2-c2cnccn2)C(=O)N1[C@@H](C)c1ccccc1]

MS (ESI): mass calcd. for $C_{18}H_{18}N_6O$, 334.4; m/z found, 335.2 [M+H]$^+$. $^1$H NMR (500 MHz, DMSO) δ 9.44 (d, J=1.1 Hz, 1H), 8.84-8.75 (m, 2H), 7.54-7.46 (m, 1H), 7.45-7.37 (m, 1H), 7.37-7.30 (m, 1H), 5.96-5.87 (m, 1H), 4.91-4.83 (d, J=13.6 Hz, 1H), 4.60-4.51 (m, 1H), 4.26-4.14 (m, 1H), 1.64 (d, J=7.1 Hz, 3H), 0.59 (d, J=6.7 Hz, 3H)

Example 96. (S)-7-(2-chloro-3-(trifluoromethyl)benzyl)-3-cyclopentyl-6-methyl-6,7-dihydro-[0,2,4]triazolo[4,3-a]pyrazin-8(5H)-one

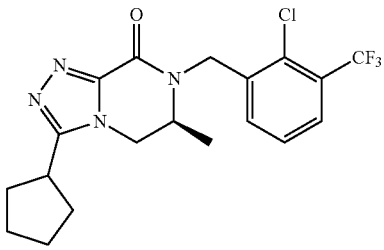 [SMILES: C[C@H]1Cn2c(nnc2C2CCCC2)C(=O)N1Cc1cccc(C(F)(F)F)c1Cl]

Example 97. (S)-7-(2-chloro-3-(trifluoromethyl)benzyl)-3-cycloheptyl-6-methyl-6,7-dihydro-[1,2,4]triazolo[4,3-a]pyrazin-8(5H)-one

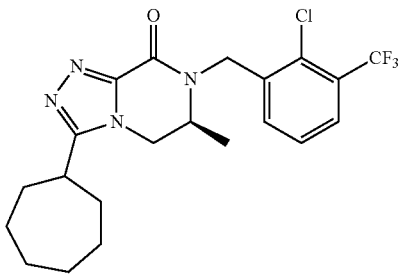 [SMILES: C[C@H]1Cn2c(nnc2C2CCCCCC2)C(=O)N1Cc1cccc(C(F)(F)F)c1Cl]

Example 98. 7-(2-chloro-3-(trifluoromethyl)benzyl)-6-cyclobutyl-3-(pyrazin-2-yl)-6,7-dihydro-[1,2,4]triazolo[4,3-a]pyrazin-8(5H)-one

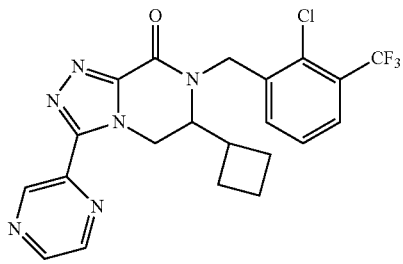 [SMILES: O=C1c2nnc(-c3cnccn3)n2CC(C2CCC2)N1Cc1cccc(C(F)(F)F)c1Cl]

Pharmacological Examples

P2X7 Antagonism in Human Peripheral Blood Mononuclear Cells (PBMCs) and Mouse/Human Whole Blood.

Human blood was collected using a blood donor program. PBMCs were isolated from blood using a Ficoll density gradient technique. Briefly, blood was laid on Ficoll solution and centrifuged at RT for 20 minutes at 2000 rpm. The buffy layer (between red blood cells and plasma) was carefully collected by aspiration, washed with PBS and centrifuged again at 1500 rpm for 15 minutes. The resulting cell pellet was washed and plated on 96 well-plates for experiments. For the Mouse/Human Whole Blood experiments, 150 µl of either mouse or human blood was platted on 96 well-plates. Lipopolysaccharide (LPS) (30 ng/ml) was added to each well and incubated for 1 hour. Test compounds were then added and incubated for 30 minutes. The P2X7 agonist, 2'(3')-O-(4-benzoylbenzoyl) adenosine 5'-triphosphate (Bz-ATP) was then added at a final concentration of 0.5 mM (PBMC) or 1 mM (blood). Cells were incubated for an additional 1.5 hours. At that point, supernatant was collected and stored for IL-1β assay using manufacturer's protocol for enzyme-linked immunosorbent assay (ELISA). Data was expressed as percent control, where control is defined as the difference in IL-1β release in LPS+Bz-ATP samples and LPS only samples. Data was plotted as response (% control) versus concentration to generate $IC_{50}$ values. In Table 2, this data is represented by PBMC P2X7 and blood P2X7 $IC_{50}$. In Table 2, when the data cell has been left blank, it is intended to mean that the compound was not tested in that assay.

P2X7 Antagonism in Recombinant hP2X7 Cells: (a) $Ca^{2+}$ Flux (b) Radioligand Binding (A) $Ca^{2+}$ flux: 1321N1 cells expressing the recombinant human, rat or mouse P2X7 channel was cultured in HyQ DME/(HyClone/Dulbecco's Modified Eagle Medium) high glucose supplemented with 10% Fetal Bovine Serum (FBS) and appropriate selection marker. Cells were seeded at a density of 25000 cells/well (96-well clear bottom black walled plates) in 100 µl volume/well. On the day of the experiment, cell plates were washed with assay buffer, containing (in mM): 130 NaCl, 2 KCl, 1 $CaCl_2$, 1 $MgCl_2$, 10 HEPES, 5 glucose; pH 7.40 and 300 mOs. After the wash, cells were loaded with the Calcium-4 dye (Molecular Device) and incubated in the dark for 60 minutes. Test compounds were prepared at 250× the test concentration in neat DMSO. Intermediate 96-well compound plates were prepared by transferring 1.2 µL of the compound into 300 µL of assay buffer. A further 3× dilution occurred when transferring 50 µL/well of the compound plate to 100 µL/well in the cell plate. Cells were incubated with test compounds and dye for 30 minutes. Calcium dye fluorescence was monitored in FLIPR as the cells were challenged by adding 50 µL/well of BzATP (final concentration is 250 µM BzATP (human and rat) or 600 µM (mouse)). The fluorescence change was measured 180 seconds after adding the agonist. Peak fluorescence was plotted as a function of test concentration and the resultant $IC_{50}$ is shown in Table 2

(B) Radioligand binding: human or rat P2X7-1321N1 cells were collected and frozen @ −80° C. On the day of the experiment, cell membrane preparations were made according to standard published methods. The total assay volume was 100 µl: 10 µl compound (10×)+(b) 40 µl tracer (2.5×)+50 µl membrane (2×). The tracer used for the assay was tritiated A-804598. The compound can be prepared as described in the literature. (Donnelly-Roberts, D. *Neuropharmacology* 2009, 56 (1), 223-229.) Compounds, tracer and membranes were incubated for 1 hour @ 4° C. The assay was terminated by filtration (GF/B filters pre-soaked with 0.3% PEI) and washed with washing buffer (Tris-HCl 50 mM). The $IC_{50}$ generated in the binding assay was corrected for tracer concentration and affinity of the tracer to derive at the affinity ($K_i$) of the test compounds.

TABLE 2

P2X7 activity of the compounds of Formula (I) in a panel of in-vitro assays

| Example # | PBMC 1 µM (% control) | PBMC 10 µM (% control) | P2X7 human $K_i$ (µM) | P2X7 rat $K_i$ (µM) | FLIPR (human) $IC_{50}$ (µM) | FLIPR (rat) $IC_{50}$ (µM) | Human whole blood $IC_{50}$ (µM) |
|---|---|---|---|---|---|---|---|
| 1 |  | 25.4 | 0.0631 |  | 0.1476 | 28.3792 |  |
| 2 | 50.6 |  | 0.0288 |  | 0.4385 | 8.6696 |  |
| 3 | −0.6 |  | 0.0063 | 0.0126 | 0.0442 | 9.3111 |  |
| 4 |  | 46.0 |  |  | 2.6853 | >10 |  |
| 5 |  | 8.8 |  |  | 0.9419 | 2.5645 |  |
| 6 |  | 23.7 |  |  | 3.4514 | >10 |  |
| 7 |  | 8.8 |  |  | 3.4041 | >10 |  |
| 8 |  | −10.6 | 0.0200 |  | 0.1466 | >10 | 10 |
| 9 |  | −3.1 | 0.0100 |  | 0.0502 | >10 | >10 |
| 10 |  | 59.3 |  |  |  |  |  |
| 11 |  | −0.4 | 0.0025 |  | 0.0018 | 0.3006 |  |
| 12 |  | 20.6 | 1.5849 |  | 0.9311 | >1 |  |
| 13 |  | 8.2, 15.4 | 0.0014 |  | 0.0010 | 0.1026 |  |
| 14 |  | 2.5 | 0.0040 |  | 0.0021 | 0.0495 |  |
| 15 |  | 4.1 | 0.9120 |  | 9.2470 | >10 |  |
| 16 |  | 8.4, 13.4 | 0.0016 | 0.0011 | 0.0007 | 0.0646 | 0.0009 |
| 17 |  | 2.0 | 0.0079 | 0.0050 | <0.001 | 1.6501 |  |
| 18 |  | −6.2 | 0.0050 | 0.0020 | <0.001 | 0.3162 |  |
| 19 |  | −9.5 | 0.0032 | 0.0063 | 0.0200 | 3.1623 |  |
| 20 |  | 4.7 | 0.0040 | 0.0050 | 0.0032 | 1.9953 |  |
| 21 |  | −3.4 | 0.0014 | 0.0035 | <0.001 | 1.5849 |  |
| 22 |  | −3.9 | 0.0063 | 0.0251 | 0.0398 | 3.1623 |  |
| 23 |  | −7.0 | 0.0032 | 0.0032 | 0.0025 | 1.2204 |  |
| 24 |  | −0.7 | 0.0251 |  | 0.1432 | >10 |  |
| 25 |  | 2.8 | 0.0251 |  | 0.0966 | 3.1477 |  |
| 26 |  | −3.7 | 0.0032 | 0.0010 | 0.0012 | 0.3750 |  |
| 27 |  | −0.7 | 0.0020 | 0.0004 | 0.0004 | 0.0361 |  |
| 28 |  | −11.7 | 0.0032 | 0.0020 | 0.0010 | 0.0069 |  |
| 29 |  | −3.4 | 0.0040 | 0.0056 | 0.0010 | 0.1222 |  |
| 30 |  | 3.3 | 0.0025 | 0.0050 | 0.0009 | 0.1879 |  |
| 31 |  | 3.0 | 0.0040 |  | 0.0012 | 0.1346 |  |
| 32 |  | 3.8 | 0.0020 | 0.0004 | 0.0002 | 0.0160 |  |
| 33 |  | 0.9 | 0.0050 |  | 0.0043 | 14.3219 |  |
| 34 |  | 0.8 | 0.0025 | 0.0028 | 0.0010 | 0.1746 |  |
| 35 |  | −3.1 | 0.0020 |  | 0.0007 | 0.0106 |  |
| 36 |  | 2.8 | 0.0251 |  | 0.0082 | 1.0641 |  |
| 37 |  | 9.0 | 0.0020 |  | 0.0069 | 1.2134 |  |
| 38 |  | 19.8 |  |  | 0.9772 | 2.6062 |  |
| 39 |  | 20.3 | 0.0275 |  | 0.0224 | 8.6696 |  |
| 40 |  | 22.3 | 0.0200 |  | 0.0104 | 1.3032 |  |
| 41 |  | 35.0 | 0.0126 |  | 0.0264 | 2.7797 |  |
| 42 |  | 37.4 | 0.0079 |  | 0.0175 | >10 |  |
| 43 |  |  |  |  |  |  |  |
| 44 |  | 26.0 |  |  | 0.1766 | 19.8609 |  |
| 45 |  | 20.1 | 0.0063 | 0.0050 | 0.1000 | 12.5893 |  |
| 46 |  | 2.7 | 0.0126 |  | 0.0033 | 0.1545 |  |
| 47 |  | −1.3 | 0.0158 |  | 0.0093 | 14.3549 |  |
| 48 |  | 0.0 | 0.0126 |  | 0.0132 | 0.5433 |  |
| 49 |  | −3.1 |  |  | 0.3864 | 13.2434 |  |
| 50 |  | 8.7 |  |  | 0.3707 | >10 |  |
| 51 |  | 22.4 |  |  | 0.7656 | >10 |  |
| 52 |  | 13.8 | 0.0079 |  | 0.0052 | 9.0991 |  |
| 53 |  | 33.2 |  |  | 3.8726 | >10 |  |
| 54 |  | 4.2 | 0.0100 |  | 0.0017 | 0.0176 |  |
| 55 |  | 8.5 | 0.5012 |  | 0.3148 | 0.7430 |  |
| 56 |  | 11.2 | 0.0063 |  | 0.0659 | 0.8241 |  |
| 57 |  | 0.1 | 0.0501 |  | 0.2188 | >10 |  |
| 58 |  | 24.6 | 0.3981 |  | 12.2180 | 24.6604 |  |
| 59 |  | 10.9 |  |  | 1.7906 | 1.1429 |  |
| 60 |  | 17.1 | 0.6310 |  | >10 | >10 |  |
| 61 |  | −1.0 | 0.0079 |  | 0.0040 | 0.0160 |  |
| 62 |  | 14.1 |  |  | 0.2495 | 9.8855 |  |
| 63 |  | 27.3 | 0.0032 |  | 0.0008 | 0.0096 |  |
| 64 |  | −0.4 | 0.0063 |  | 0.0014 | 0.0046 |  |
| 65 |  | 15.9 | 0.1000 |  | 0.0181 | 0.3963 |  |
| 66 |  | 20.7 | 0.0050 |  | 0.0010 | 0.0082 |  |
| 67 |  | 6.9 | 0.0079 |  | 0.0043 | 0.2825 |  |
| 68 |  | 1.6 | 0.0040 |  | 0.0011 | 0.0118 |  |
| 69 |  | 20.8 | 0.0316 |  | 0.0200 | 0.3981 |  |
| 70 |  | 9.1 | 0.0079 |  | 0.0079 | 0.7943 |  |
| 71 |  | 1.2 | 0.0013 |  | 0.0003 | 0.0103 |  |
| 72 |  | 1.9 | 0.0025 |  | 0.0009 | 0.0056 |  |
| 73 |  | 6.2 | 0.0126 |  | 0.0014 | 0.1327 |  |
| 74 |  | 0.3 | 0.0100 |  | 0.0015 | 0.0051 |  |

TABLE 2-continued

P2X7 activity of the compounds of Formula (I) in a panel of in-vitro assays

| Example # | PBMC 1 μM (% control) | PBMC 10 μM (% control) | P2X7 human Ki (μM) | P2X7 rat Ki (μM) | FLIPR (human) IC$_{50}$ (μM) | FLIPR (rat) IC$_{50}$ (μM) | Human whole blood IC$_{50}$ (μM) |
|---|---|---|---|---|---|---|---|
| 75 |  | 22.6 | 0.0032 | 0.0018 | <0.001 | 0.1259 |  |
| 76 |  | 16.9 | 0.0025 | 0.0016 | <0.001 | 0.1585 |  |
| 77 |  | 105.2 |  |  |  |  |  |
| 78 |  | 8.3 | 0.0158 |  | 0.0425 | 3.2659 |  |
| 79 |  | 15.6 |  |  | 9.6161 | >10 |  |
| 80 |  | 8.4 | 0.0316 |  | 0.2483 | 41.4000 |  |
| 81 |  | 170.3 |  |  |  |  |  |
| 82 |  | 22.2 | 0.0631 |  | 0.1321 | >10 |  |
| 83 |  | 15.6 |  |  | 0.8222 | 11.0918 |  |
| 84 |  | 25.9 |  |  | 0.3404 | >10 |  |
| 85 |  | 16.6 | 0.0050 |  | 0.0016 | 0.7079 |  |
| 86 |  | 28.3 | 0.0631 |  | 0.0971 | 1.3709 |  |
| 87 |  | 27.0 | 0.0316 |  | 0.0425 | 1.5560 |  |
| 88 |  | 29.9 | 0.0050 |  | 0.0040 | 6.0395 |  |
| 89 |  | 30.7 |  |  | 0.0264 | 7.2778 |  |
| 90 |  | 24.4 |  |  | 1.0000 | 19.9526 |  |
| 91 |  | 11.6 |  |  | 1.2190 | 18.8799 |  |
| 92 |  | -1.0 | 0.0316 | 0.0164 | 0.1094 | 10.0000 |  |
| 93 |  | 4.5 | 0.1585 | 0.0316 | 0.0881 | 3.0479 |  |
| 94 |  | -1.3 | 0.0141 | 0.1230 | 0.0865 | >10 |  |
| 95 |  | 3.1 |  |  | 8.2414 | 3.8994 |  |

What is claimed is:

1. A method for modulating P2X7 receptor activity in a subject, comprising administering to a subject in need thereof a therapeutically effective amount of at least one compound of Formula (I):

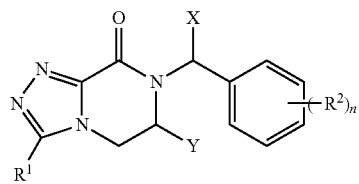

Formula (I)

wherein:

$R^2$ is H, halo, $SO_2CH_3$, $C_{1-3}$ alkyl, $NO_2$, $NH_2$, perhaloalkyl or perhaloalkoxy; or two $R^2$ substituents are taken together to form:

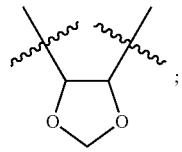 [SMILES: *C1OCOC1*]

;

n is 0, 1, 2, or 3;
X is H or $C_1$-$C_3$ alkyl;
Y is H, $C_1$-$C_3$ alkyl or $C_3$-$C_4$ cycloalkyl;
$R^1$ is selected from the group consisting of:

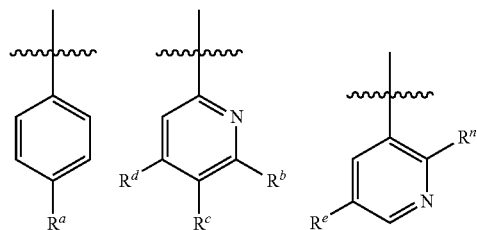

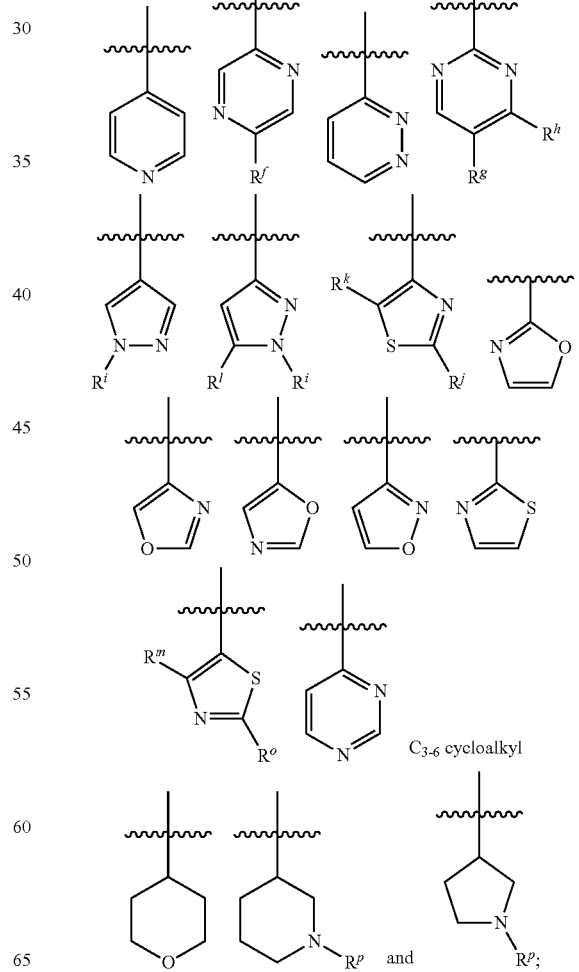

$C_{3-6}$ cycloalkyl and $R^d$ is H or alkoxy;

$R^a$, $R^c$ and $R^g$ are independently H or halo;

$R^e$ is H, $C_1$-$C_3$ alkyl or halo;

$R^b$, $R^f$, $R^h$, $R^i$, $R^j$, $R^k$, $R^l$, $R^m$, $R^n$ and $R^o$ are independently H, $C_1$-$C_3$ alkyl or perhaloalkyl;

$R^p$ is H or $CO_2C(CH_3)_3$; and pharmaceutically acceptable salts of compounds of Formula (I).

2. The method according to claim 1, wherein the subject suffers from a disease, disorder or medical condition selected from the group consisting of rheumatoid arthritis, osteoarthritis, psoriasis, septic shock, allergic dermatitis, allergic rhinitis, asthma, idiopathic pulmonary fibrosis, airway hyper-responsiveness, chemotherapy-induced neuropathic pain, inflammatory pain, spontaneous pain, low back pain, postherpetic neuralgia, diabetic neuropathy, fibromyalgia, major depression, major depressive disorder, treatment resistant depression, bipolar disorder, anxious depression, anxiety, cognition, multiple sclerosis, schizophrenia, autism, spinal cord injury, traumatic brain injury, diabetes, diabetes mellitus, thrombosis, ischemia, hypertension, myocardial infarction, incontinence, lower urinary tract syndrome, glomerulonephritis, osteoporosis, osteopetrosis, glaucoma, interstitial cystitis, cough, ureteric obstruction, sepsis, amyotrophic lateral sclerosis, chlamydia, neuroblastoma, tuberculosis, migraine, an epileptic seizure, irritable bowel syndrome, irritable bowel disease, ischemic heart disease, chronic obstructive pulmonary disease, Parkinson's disease, Alzheimer's disease, Huntington's disease, Crohn's disease, Chaga's disease, cardiovascular disease, polycystic kidney disease, a disease involved with and without neuroinflammation of the central nervous system, a disease of the nervous and neuro-immune system, an acute pain state of neuropathic pain, a chronic pain state of neuropathic pain, a skeletal disorder, a sleep disorder, a mood disorder and a stress-related disorder.

3. The method according to claim 2, wherein the subject suffers from a disease, disorder or medical condition selected from the group consisting of a mood disorder, treatment resistant depression, major depression, major depressive disorder, bipolar disorder, anxious depression and anxiety.

4. The method according to claim 2, wherein the subject suffers from a disease, disorder or medical condition selected from the group consisting of irritable bowel syndrome, irritable bowel disease and Crohn's disease.

5. The method according to claim 2, wherein the subject suffers from a mood disorder.

6. The method according to claim 2, wherein the subject suffers from anxiety.

7. The method according to claim 2, wherein the subject suffers from bipolar disorder.

8. The method according to claim 2, wherein the subject suffers from major depression.

9. The method according to claim 2, wherein the subject suffers from anxious depression.

10. The method according to claim 2, wherein the subject suffers from treatment resistant depression.

11. The method according to claim 2, wherein the subject suffers from Alzheimer's disease.

* * * * *